(12) United States Patent
Srimathveeravalli et al.

(10) Patent No.: US 11,723,709 B2
(45) Date of Patent: *Aug. 15, 2023

(54) SYSTEM, METHOD AND COMPUTER-ACCESSIBLE MEDIUM FOR IN-VIVO TISSUE ABLATION AND/OR DAMAGE

(71) Applicant: MEMORIAL SLOAN KETTERING CANCER CENTER, New York, NY (US)

(72) Inventors: Govindarajan Srimathveeravalli, Amherst, MA (US); Stephen Barnett Solomon, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 308 days.

This patent is subject to a terminal disclaimer.

(21) Appl. No.: 16/927,261

(22) Filed: Jul. 13, 2020

(65) Prior Publication Data
US 2021/0000527 A1 Jan. 7, 2021

Related U.S. Application Data

(63) Continuation of application No. 14/910,600, filed as application No. PCT/US2014/049880 on Aug. 6, 2014, now Pat. No. 10,709,491.
(Continued)

(51) Int. Cl.
*A61B 18/12* (2006.01)
*A61B 6/03* (2006.01)
(Continued)

(52) U.S. Cl.
CPC .............. *A61B 18/12* (2013.01); *A61B 6/037* (2013.01); *A61B 18/1206* (2013.01);
(Continued)

(58) Field of Classification Search
CPC ......... A61B 18/18; A61B 18/04; A61B 18/12; A61B 18/1206; A61B 2018/00577; A61B 2018/1475; A61B 2018/00613
See application file for complete search history.

(56) References Cited

U.S. PATENT DOCUMENTS 5,718,246 A * 2/1998 Vona ..................... A61N 1/327
607/2
5,873,849 A * 2/1999 Bernard ................ A61N 1/327
607/148

(Continued)

FOREIGN PATENT DOCUMENTS

EP 1207797 5/2002
WO 2012071526 5/2012

OTHER PUBLICATIONS

Communication Under Rule 71(3) EPC dated May 27, 2022 for European Patent Application No. 14833703.3.
(Continued)

*Primary Examiner* — Joanne M Rodden
*Assistant Examiner* — Sean W Collins
(74) *Attorney, Agent, or Firm* — Hunton Andrews Kurth LLP

(57) ABSTRACT

Systems, methods and computer-accessible mediums can be provided that can establish particular parameters for electric pulses based on a characteristic(s) of the tissue(s), and control an application of the electric pulses to tissue(s) for a plurality of automatically controlled and separated time periods to ablate the tissue(s) through mediation of membrane potential and through inducing the cells through a plurality of charge-discharge cycles such that an electroporation of a majority of the tissue(s) is prevented or reduced.

30 Claims, 43 Drawing Sheets

Related U.S. Application Data

(60) Provisional application No. 61/862,580, filed on Aug. 6, 2013.

(51) Int. Cl.

| | |
|---|---|
| A61B 18/00 | (2006.01) |
| A61B 90/00 | (2016.01) |
| A61B 18/18 | (2006.01) |
| A61B 18/14 | (2006.01) |
| A61B 34/20 | (2016.01) |
| A61B 17/00 | (2006.01) |

(52) U.S. Cl.
CPC ...... *A61B 18/1233* (2013.01); *A61B 18/1492* (2013.01); *A61B 18/1815* (2013.01); *A61B 2017/00194* (2013.01); *A61B 2018/00577* (2013.01); *A61B 2018/00613* (2013.01); *A61B 2018/00642* (2013.01); *A61B 2018/00648* (2013.01); *A61B 2018/00666* (2013.01); *A61B 2018/00726* (2013.01); *A61B 2018/00761* (2013.01); *A61B 2018/00767* (2013.01); *A61B 2018/00791* (2013.01); *A61B 2018/00827* (2013.01); *A61B 2018/00839* (2013.01); *A61B 2018/00875* (2013.01); *A61B 2018/143* (2013.01); *A61B 2018/1475* (2013.01); *A61B 2034/2057* (2016.02); *A61B 2090/373* (2016.02); *A61B 2090/374* (2016.02); *A61B 2090/378* (2016.02); *A61B 2090/3762* (2016.02)

(56) References Cited

U.S. PATENT DOCUMENTS

| | | | |
|---|---|---|---|
| 6,326,177 B1 * | 12/2001 | Schoenbach | A61B 18/1206 600/12 |
| 7,680,543 B2 | 3/2010 | Azure et al. | |
| 7,722,606 B2 | 5/2010 | Azure et al. | |
| 8,048,067 B2 | 11/2011 | Davalos et al. | |
| 8,114,072 B2 | 2/2012 | Long et al. | |
| 8,282,631 B2 | 10/2012 | Davalos et al. | |
| 10,709,491 B2 * | 7/2020 | Srimathveeravalli | A61B 18/1233 |
| 2003/0078490 A1 | 4/2003 | Damasco et al. | |
| 2005/0070896 A1 | 3/2005 | Daniel | |
| 2006/0293731 A1 | 12/2006 | Rubinsky et al. | |
| 2008/0015571 A1 | 1/2008 | Rubinsky et al. | |
| 2009/0076502 A1 | 3/2009 | Azure et al. | |
| 2009/0326436 A1 | 12/2009 | Rubinsky et al. | |
| 2010/0030211 A1 | 2/2010 | Davalos et al. | |
| 2010/0261994 A1 * | 10/2010 | Davalos | A61B 18/1477 600/407 |
| 2011/0040170 A1 | 2/2011 | Geva et al. | |
| 2011/0060393 A1 | 3/2011 | Azure et al. | |
| 2011/0118732 A1 | 5/2011 | Rubinsky et al. | |
| 2012/0027741 A1 | 2/2012 | Coqueron et al. | |
| 2012/0109122 A1 | 5/2012 | Arena et al. | |
| 2012/0123411 A1 | 5/2012 | Ibrahim et al. | |
| 2012/0220998 A1 | 8/2012 | Long et al. | |
| 2012/0221002 A1 | 8/2012 | Long et al. | |
| 2012/0277741 A1 | 11/2012 | Rubinsky et al. | |
| 2013/0218157 A1 | 8/2013 | Callas | |
| 2015/0065946 A1 | 3/2015 | Gehl | |

OTHER PUBLICATIONS

Tadej Kotnik and Damijan Miklavöiö "Analytical Description of Transmembrane Voltage Induced by Electric Fields on Spheroidal Cells" Biophysical Journal, vol. 79, Aug. 2000, pp. 670-679.

G. Pucihar, T. Kotnik, B. Valic, and D. Miklavcic "Numerical Determination of Transmembrane Voltage Induced on Irregularly Shaped Cells" A1111als of Biomedical Engineering, vol. 34, No. 4, Apr. 2006, pp. 642-652.

Holder, Appendix A: Brief introduction to bioimpedance. Electrical Impedance Tomography Methods, History and Applications. Taylor & Francis; 2004 pp. 411-422.

Dallaporta et al, Plasma Membrane Potential in Thymocyte Apoptosis. The Journal of 19 Immunology, Jun. 1, 1999, vol. 162, No. 11, pp. 6534-6542.

Extended European Search Report for European Patent Application No. 14833703.3 dated Jan. 25, 2017.

Communication pursuant to Article 94(3) EPC dated Aug. 20, 2018 for European Patent Application No. 14833703.3.

International Search Report for International Patent Application No. PCT/US2014/049880 dated Nov. 21, 2014.

International Written Opinion for International Patent Application No. PCT/US2014/049880 dated Nov. 21, 2014.

Communication under Rule 71(3) EPC dated Nov. 21, 2022 for European Patent Application No. 14833703.3.

* cited by examiner

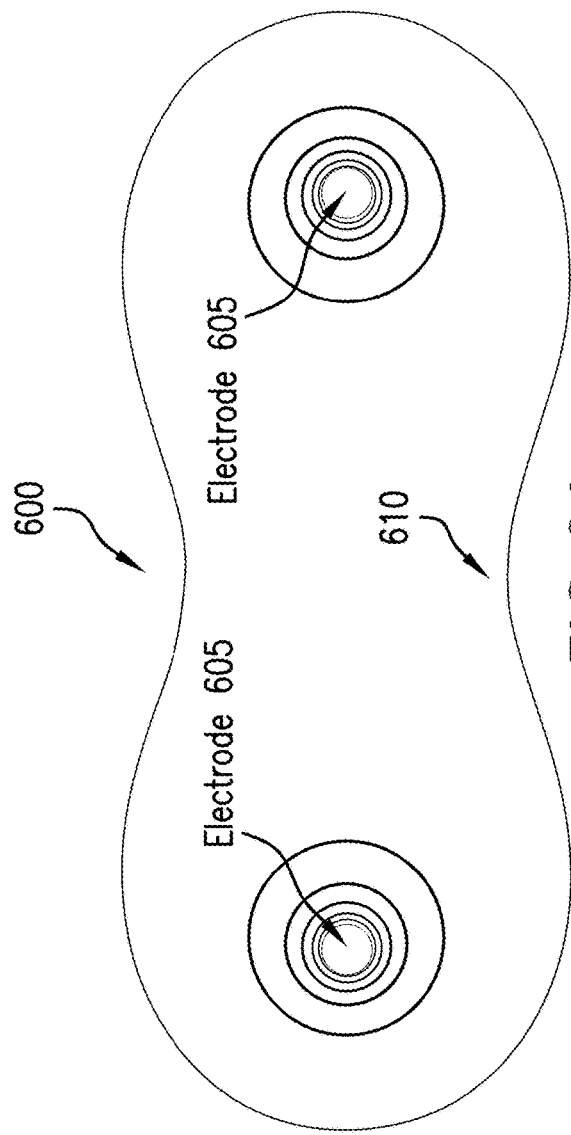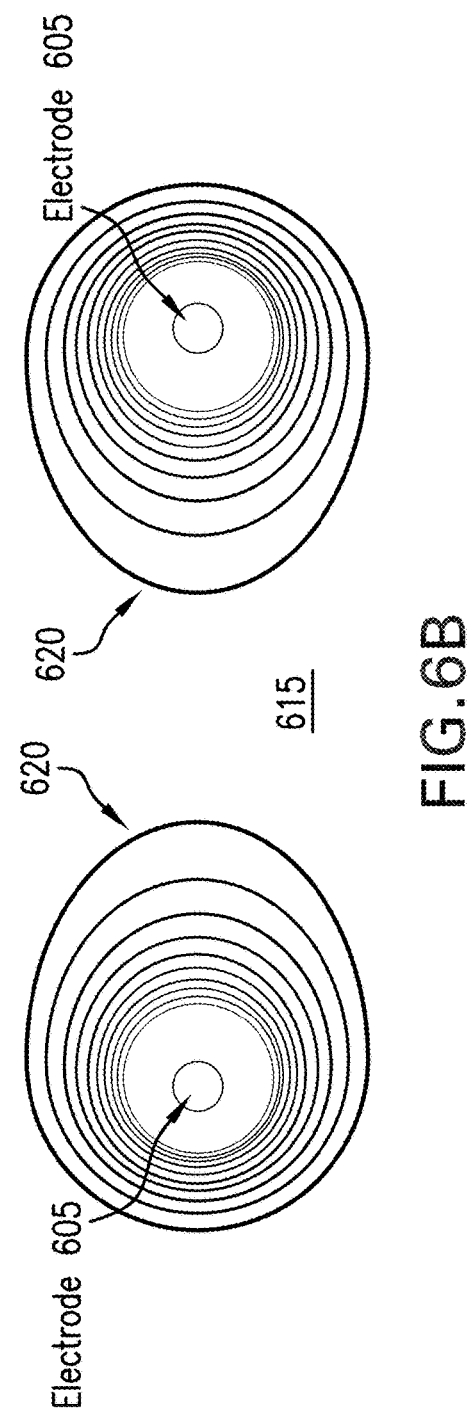

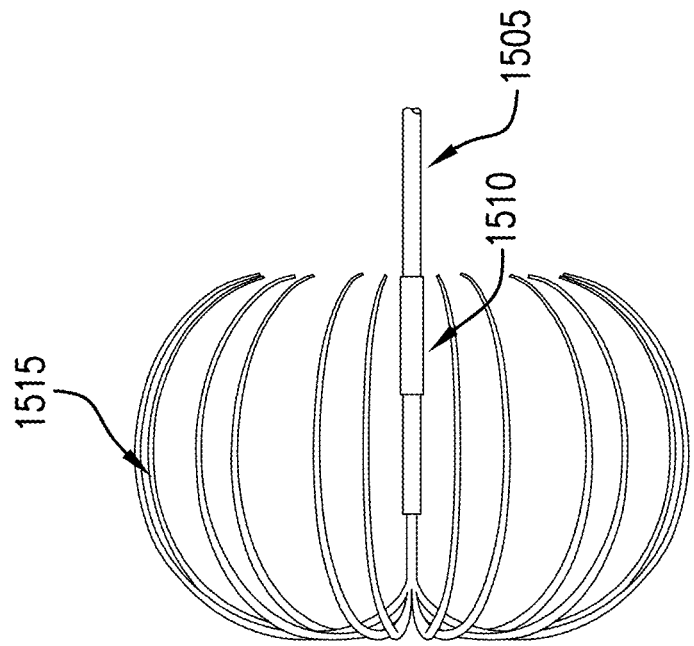
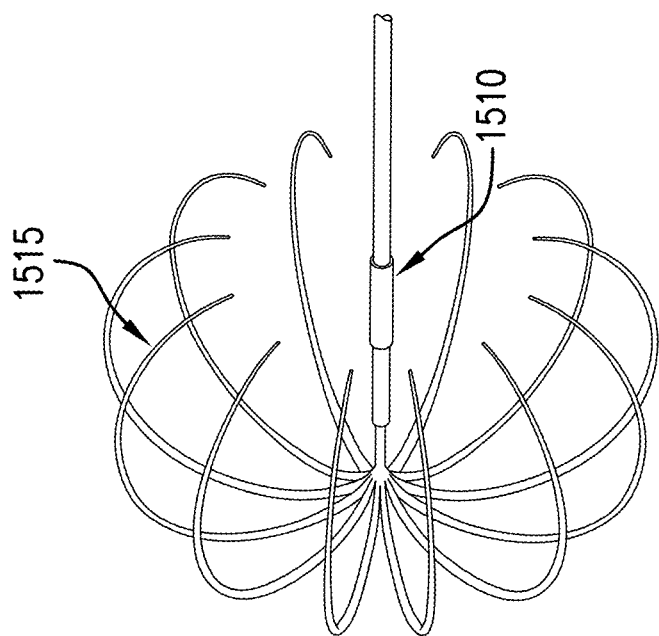
FIG.15

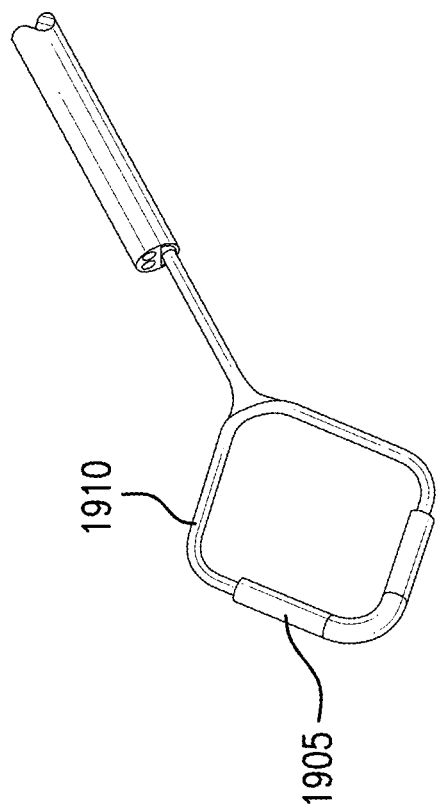
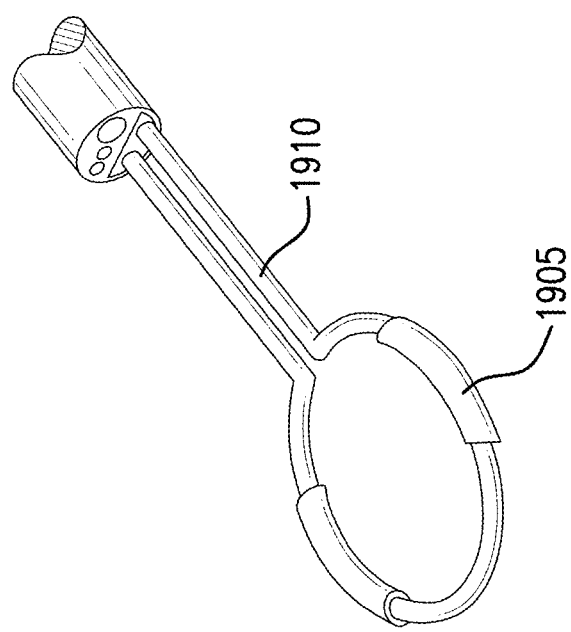

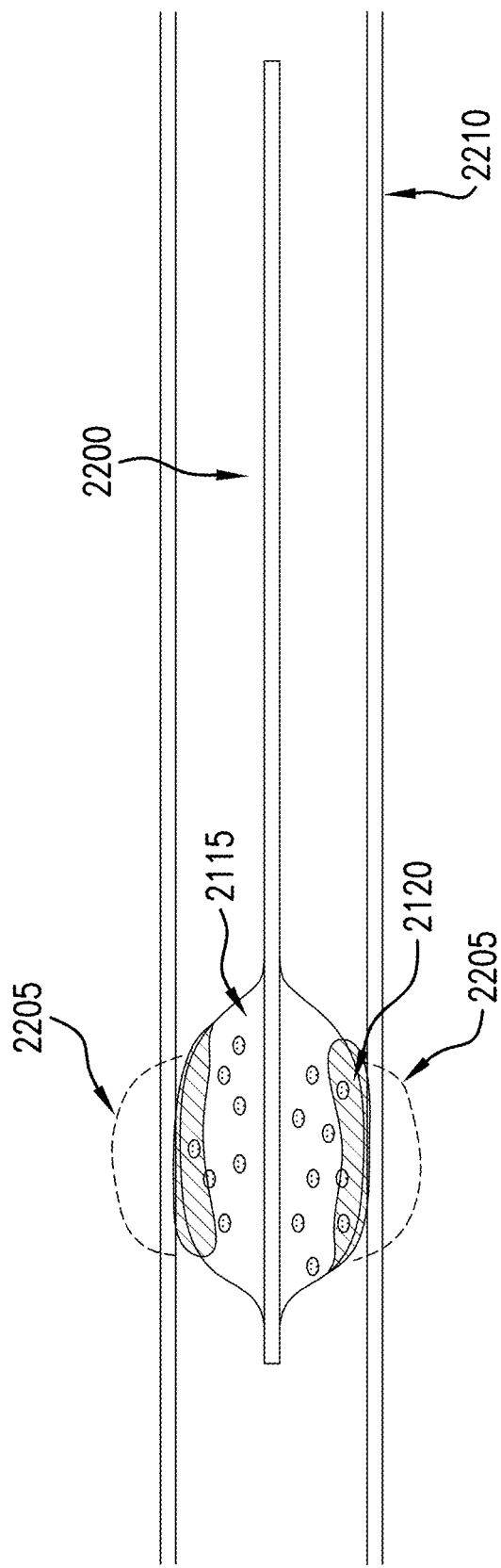

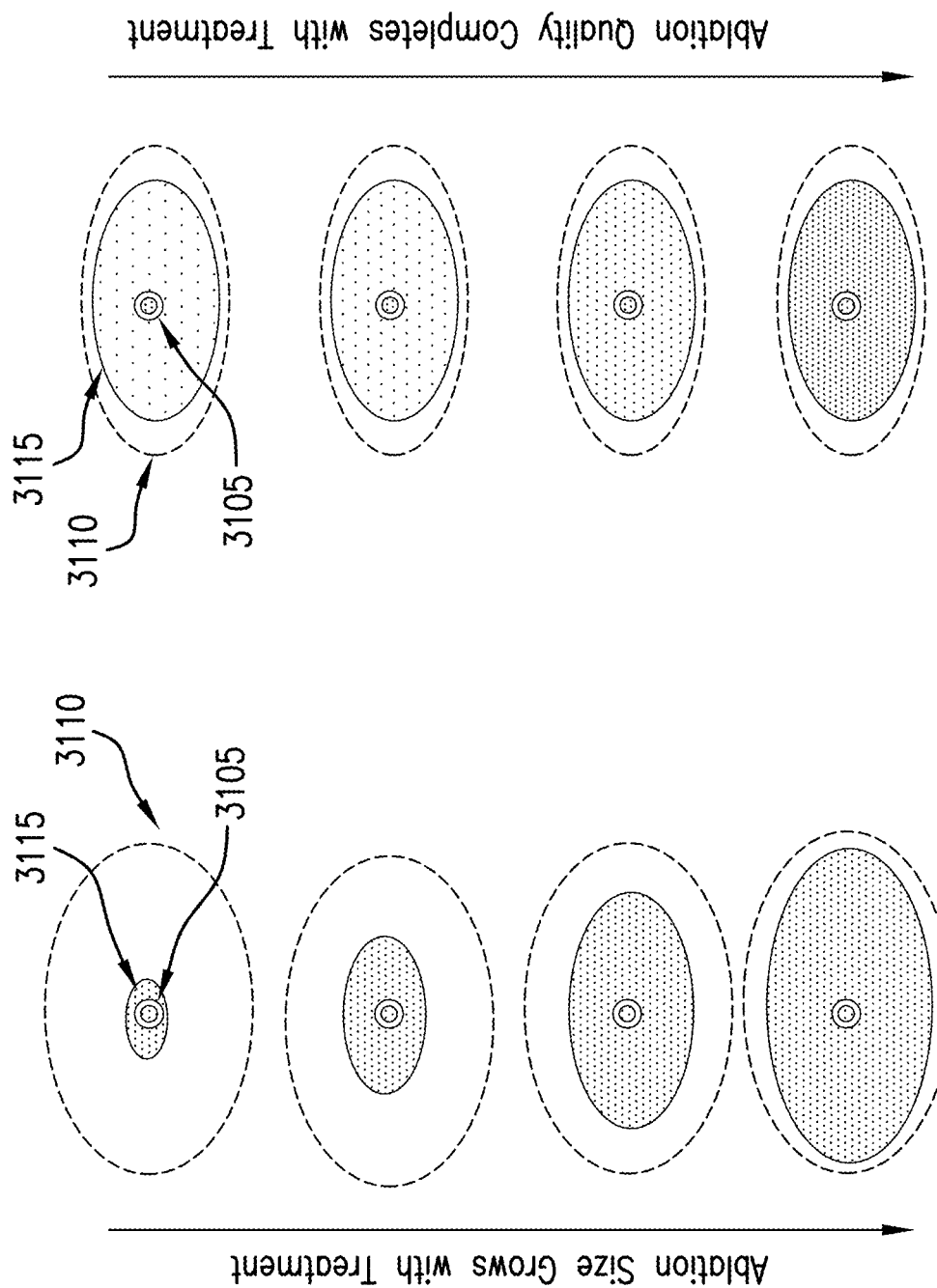

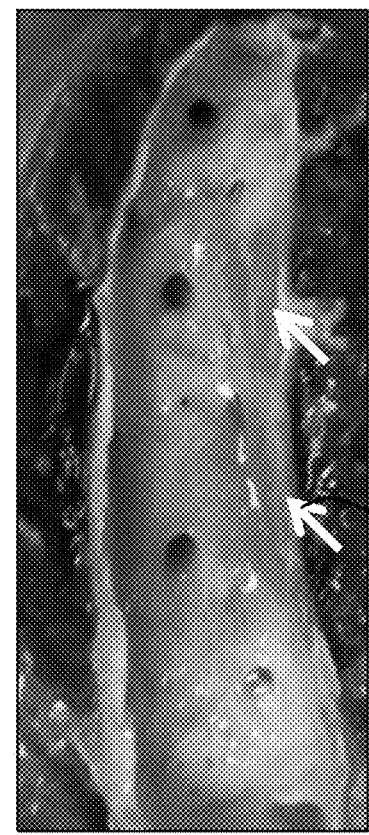
FIG.36A
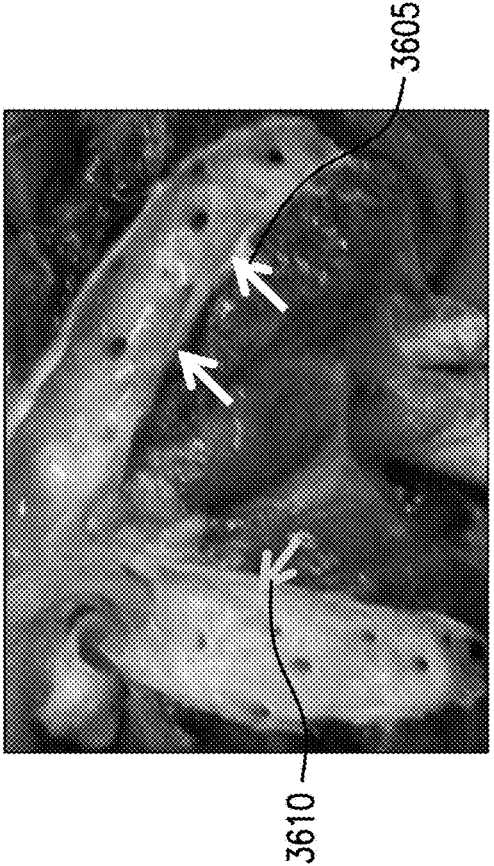
FIG.36B
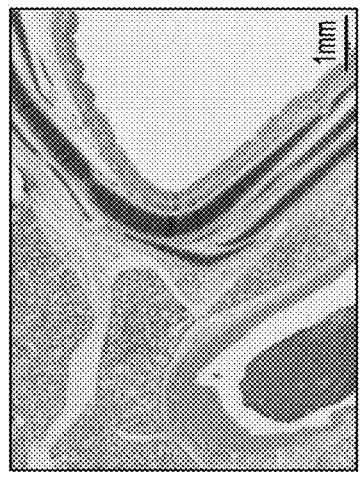
Treated (transverse, hi mag)
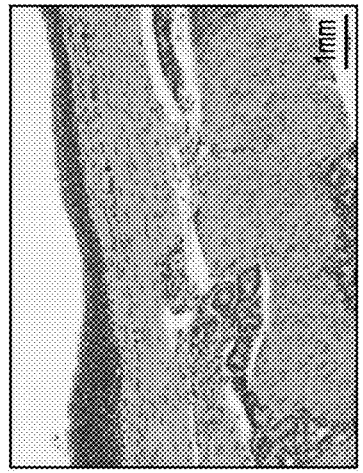
Adjacent Untreated (transverse, hi mag)
Treated (Full section, lo mag)
FIG.36C ＃ SYSTEM, METHOD AND COMPUTER-ACCESSIBLE MEDIUM FOR IN-VIVO TISSUE ABLATION AND/OR DAMAGE

CROSS-REFERENCE TO RELATED APPLICATIONS

The present application is a continuation of U.S. National phase patent application Ser. No. 14/910,600, filed on Feb. 5, 2016, issuing as U.S. patent Ser. No. 10/709,491, on Jul. 14, 2020, which relates to and claims the benefit and priority from International Patent Application No. PCT/US2014/049880 filed Aug. 6, 2014, which claims the benefit and priority from U.S. Provisional Patent Application No. 61/862,580 filed on Aug. 6, 2013, the entire disclosures of which are incorporated herein by reference.

FIELD OF THE DISCLOSURE

The present disclosure relates generally to exemplary system, method and computer-accessible medium for in-vivo tissue ablation, and more specifically, to exemplary embodiments of the exemplary system method and computer-accessible medium that can damage or kill tissue and/or one or more cells using bioelectric pulses and/or cellular processes through in-vivo tissue ablation.

BACKGROUND INFORMATION

Cells can have a transmembrane voltage that can be used to facilitate electro-chemical transport of molecules and ions across its membrane. At resting values and measured across the membrane, this voltage can be negative, and can have a small magnitude in the order of a few 10's of mV. As shown in FIGS. 1A, 1B and 2, the transmembrane voltage can vary based on the cell type, function and cellular activity. The transmembrane voltage can also vary in response to a voltage imposed from an external source. The membrane potential 205 can rise or fall by few 10's of mV during normal cellular processes. The membrane potential can also be altered or returned to resting values by the cell through the coordinated action of enzymes such as $Na^+/K^+$-ATPase ("ATP"), ion pumps and voltage activated channels. It is previously known that the physiological failure of the enzyme or ion pumps can lead to ionic imbalance and changes in osmolarity, which in extreme cases can lead to cell death. (See, e.g., FIGS. 1A-1D, 2, 3 and 4). The exemplary voltage (e.g., an external voltage 210) imposed upon the cell generated from an external source can be considered an external voltage, and can be used to manipulate or affect the cell in some way.

FIGS. 1A-1C illustrate the change in ionic balance with respect to the change in polarization (e.g., the polarization illustrated in FIG. 1D). As illustrated in FIG. 1A, the cell is at resting potential, which can be established through the balance of $K^+$ and $Na^+$ ions in the intracellular and extracellular space. As illustrated in FIG. 1B, the cell adjusts the resting membrane potential through exchange of ions through specialized gates and channels (arrows 105) to achieve a different membrane potential to perform cellular functions. This can also occur in response to an externally imposed electric field. As illustrated in FIG. 1C, the cell is shown redistributing ions in the intra and extra cellular space to return to its resting potential.

When a small external electric field (e.g., less than about 500 mV) can be imposed on a cell, contingent on the magnitude of the field and positive or negative nature of the field, the cell can undergo hyperpolarization or depolarization. During the hyperpolarization, the transmembrane voltage can decrease to a larger negative value, and during depolarization the transmembrane voltage can increase to a positive value. When the external field can be removed, the cell can use ATP, ion pumps and voltage activated channels to return the cell back to its resting potential value. ATP can be consumed during this process, and energy consumed in the process of returning the cell to resting values can amount to up to about 25-30% of a cell's total metabolic energy consumption during this process. Additionally, it is previously known that the external field can cause the activation of electrically sensitive structures in the cell, such as the plasma membrane, and the voltage gated ion channels and pumps. These structures are also known to undergo mechanical deformation, but can rapidly return to normal shape when the external field can be removed. Finally, the external electric field can cause generation and flow of inward or outward currents. (See, e.g., FIG. 2). The flow of currents can be dictated by the sign of the external fields. These bio-electric phenomena are well documented in the literature, and can form the basis of experimental techniques (e.g., patch clamp studies) and clinical methods (e.g., neuromuscular activation). Such electrical stimulation of cells can be known to be safe and regularly used for therapeutic purposes.

It is previously known that deliberate application of an electric field in the form of discrete unipolar pulses, with a square or an exponential shape, can result in creation of nano-sized pores in the plasma membrane. This phenomenon is called electroporation or electro-permeabilization, and can be contingent on the selection of pulse parameters; the pores created in the plasma membrane can be enduring or transient. The former technique can be called irreversible electroporation ("IRE"), and the latter can be called reversible electroporation. Reversible electroporation can be used for the introduction of molecules or genetic material into the cells. The pulse parameters for reversible electroporation can be carefully chosen to cause the cell to survive, or remain viable, following the permeabilization process. In the case of irreversible electroporation, pulse parameters can be deliberately chosen that can result in creation of pores in cell membranes that can be permanent. Thus, the cells can be unable to recover from this process, and as a result, can undergo necrosis due to acute injury. A dramatic increase in electric impedance of the treated tissue can be observed, or can be considered as evidence of both reversible and irreversible forms of electroporation taking place in the targeted cells.

The application of irreversible electroporation can be enhanced by identifying square pulse parameters such as pulse width, applied voltage, number of pulses and pulse repetition time that can facilitate delivery of IRE while minimizing the collateral rise in tissue temperature due to the passage of electrical current. This enhanced technique has been termed non-thermal IRE. Non-thermal IRE can be achieved through application of pulse parameters such that a rise in transmembrane voltage of 0.7-1.0V can be achieved leading to permanent electroporation of the tissue without cell injury due to thermal mechanisms. While the field of IRE has been reviewed, its application can be enhanced by modifications that can minimize temperature related effects of the pulse application. Imaging techniques can be used, such as electrical impedance tomography that can specifically exploit the decrease in tissue impedance following non-thermal IRE to map ablated tissue in-vivo. Broadly, the electric field strengths of about 500-2500 V/cm or about 800-1000 V/cm can be used (e.g., such that a minimum sustained threshold of about 637V/cm) is sustained to achieve IRE in tissue. In addition, to achieve non-thermal IRE, the pulse width has to be multiple times longer than that of the membrane charging time of the cell types in the target tissue, the applied voltage and its derivative, and the electric field strength can be significantly larger than what can be used in reversible electroporation. The number of pulses used to achieve IRE can be larger than what can be used for reversible electroporation, and can be such that the inter pulse spacing or duration allows for the buildup of transmembrane voltage to the desired IRE threshold. (See, e.g., References 1-4).

Additional enhancements to IRE have been explored to exploit the temperature dependent properties of change in the transmembrane potential to achieve IRE at thresholds that can be lower than what has been reported by (see, e.g., References 1-4). This can be achieved by using a train of two different pulses, such that the first sequence can be used to heat the target tissue but can be insufficient to ablate the tissue by itself, and which can be followed by a second pulse sequence that can induce IRE in the targeted region. The heating caused by the first pulse sequence can be used to reduce the transmembrane voltage threshold of IRE from about 0.7-1.0V to about 0.5V. To achieve this effect, the first pulse sequence can be applied rapidly, with low external electric field strength and the second pulse sequence can be applied with pulse considerations such as a pulse length longer than membrane charging time. Inter-pulse spacing can be used to facilitate the building of transmembrane potential and voltage thresholds that can be sufficiently large to induce IRE. While this technique can reduce the threshold potential requirements for achieving IRE, it can no longer be considered a non-thermal ablation technique. The increase in temperature, while insufficient to ablate cells, can otherwise be sufficient to destroy heat sensitive structures such as bile ducts and nerves that can be in vicinity of the treatment regions. This reduces some of the benefits of non-thermal IRE. (See, e.g., References 1-7).

Another technique can use very high voltage pulsed electric fields to directly permeabilize the nuclear membrane of cells without affecting the plasma membrane. (See, e.g., Reference 8). This technique has been described as nanoporation or supraporation. In this technique, pulses of nanosecond width and spacing can be used in conjunction with field strengths larger than about 10,000 V/cm. The pulses can have a width much shorter than the membrane charging time of most cells, and therefore, can bypass charging the plasma membrane instead of directly affecting membrane of intra-cellular organelles such as the nucleus and the mitochondria. At the end of the treatment application, the cells have been reported to undergo apoptosis due to disrupted nuclear architecture, but the plasma or cell membrane itself may not be permeabilized. Therefore, concomitant electrical conductivity changes seen in IRE can be absent here. Nanoporation is also believed to kill cells without large temperature changes and can be considered a non-thermal ablation technique that can otherwise be benign to non-cellular structures in the treated area.

Further enhancements to both non-thermal IRE and nanoporation can be achieved with a derivative technique called high frequency irreversible electroporation ("HI-FIRE"). The use of a pulsed waveform has been researched such that the pulses can be shorter than the membrane charging time of either the nuclear or the plasma membrane. (See, e.g., References 9-13). A multitude of such pulses, or significantly larger number than what can typically be used for either IRE or nanoporation, can be applied with a very short inter-pulse spacing. This arrangement can facilitate the spatial or temporal summation of the effect of these pulses, and effectively facilitates them to increase the transmembrane potential to achieve either nanoporation or IRE contingent on the applied field strength. A benefit of this technique can be that it can facilitate direction of ablation through layers such as epithelial cells or other cells with tight gap junctions that would otherwise get charged and ablated, therefore impeding the satisfactory ablation of an underlying target tissue. While the pulse parameters can be different from other techniques (see, e.g., References 1-7), this technique can use a similar range of field strengths and membrane potentials (e.g., about 0.7-1.0V) to achieve cell injury and death. (See, e.g., References 9-13). The high energy electrical fields used to induce IRE, the inability to selectively target cells, the concomitant tissue edema, the impact on electrical sensitive structures, and the effect of tissue heterogeneity on ablation outcomes can limit the application of IRE and associated techniques in the clinical setting.

A number of energy sources and associated ablation techniques can be clinically used for the therapy of patients. Exemplary ablation methods can be categorized on basis of the energy source used for causing injury to the cell. Ablation that predominantly uses temperature differences to cause cell injury can be called thermal ablation techniques which can include radiofrequency ablation, microwave ablation, cryoablation, some forms of electrocautery and laser therapy. Another category of ablation techniques can predominantly rely on application of strong external electric fields to cause pore formation in cell membranes. These techniques can be broadly termed electroporation. Electroporation may not be intended to cause permanent injury to the cell. Techniques such as irreversible electroporation, nano or supraporation, high frequency electroporation and enhanced electroporation can be derivative methods which can be meant for inducing cell death through permanent injury. These techniques can typically be called non-thermal techniques, as the primary cause of cell death may not be due to variations in tissue temperature. There can be other non-thermal ablation techniques, which include photodynamic therapy, argon-plasma coagulation, electrochemical-therapy, electrochemotherapy and different forms of radiation therapy. In addition to these, many of these ablation techniques can be performed in combination with each other.

Thermal ablation techniques can use an applicator to provide an energy source or sink in proximity to the targeted region. Depending on the technique, the temperature gradient can be established through electromagnetic wave induced molecular friction or heating and/or cooling through adiabatic expansion of gases, joule heating processes or the application of energy through light sources. While there can be slight variations in the exact mechanism of cell death, generally cell necrosis can be induced through heat induced coagulation of proteins and direct thermal injury of cell components. In the case of cryoablation, cell death can be induced through creation of intra and extra-cellular ice crystals that can cause cell rupture and damage to interstitial tissue. Due to their working mechanism, there can be two fundamental shortcomings of these thermal ablation techniques. First, the technique can be non-targeted, destroying all forms of tissue, extra cellular matrix and other components that can fall within the region of altered temperature values. Because of this, scarring can be a common outcome following ablation and also otherwise healthy tissue, vasculature and critical structures such as nerves can also be permanently injured during treatment. Elevated temperatures can increase risk of perforation of lumen structures, and therefore can limit application of these ablation techniques in proximity to lumen such as the ureter, bile duct or the esophagus.

While some of these techniques have been adopted for mucosal ablation within lumen, their use can be limited to sub-millimeter depths. These techniques may be unable to treat tissue deeper than this depth without significant risk of perforating the tissue or inducing strictures in the long term. Some of these techniques have also been adopted for targeting nerves that can surround lumen, for example nerves surrounding the renal arteries or the bronchus. However, these ablations can be non-targeted in that they cannot selectively ablate the nerve without permanently injuring or destroying tissue that lies in the path of energy delivery. Therefore in these cases, thermal ablation can damage the muscularis and adventitia of the lumen supporting the nerves. The second significant shortcoming of thermal ablation techniques can be that they can be affected by heat sinks within the body. Perfusion and vascular flow can significantly affect the completeness and success with which these techniques can ablate cells within a target area. It may not be uncommon for failure of these techniques in ablating tissue adjacent to large blood vessels, which in fact can be a contra-indication for the use these techniques. (See, e.g., FIGS. 26A and 26B).

Thus, it may be beneficial to provide an exemplary embodiment of a system, method and computer-accessible medium for cell targeted in-vivo tissue ablation, without damaging surrounding non-targeted tissues, and which can overcome at least some of the deficiencies described herein above.

SUMMARY OF EXEMPLARY EMBODIMENTS

Systems, methods and computer-accessible mediums can be provided that can establish particular parameters for electric pulses based on a characteristic(s) of the tissue(s), and control an application of the electric pulses to tissue(s) for a plurality of automatically controlled and separated time periods to ablate the tissue(s) such that an electroporation of a majority of the tissue(s) is prevented or reduced. The electric pulses can include a waveform(s). The waveform can be based on a (i) an applied voltage of the electric pulses, (ii) a sign of the electric pulses, (iii) a length of exposure of the tissue(s) to the electric pulses, (iv) a relative field strength of the electric pulses, (v) a current density of the electric pulses, or (vi) a duty cycle of the electric pulses. The waveform(s) can have a shape of (i) a square, (ii) a sawtooth, (iii) a triangle, (iv) a trapezoid or (v) an exponential sinusoidal pulse. The waveform can be applied as (i) monopolar, (ii) bipolar, or (iii) direct current shifted. An approximately stable impedance level of the tissue(s) can be substantially maintained while the electric pulses are applied. The impedance level can be increased while the electric impulses are applied.

In some exemplary embodiments of the present disclosure, a time between at least two of the separated time periods can be controlled based on a further time period for the duration of which a particular cell(s) of the tissue(s) can substantially regain a resting value(s) before being hyperpolarized or depolarized. The cell(s) can be (i) injured, (ii) killed, (iii) have its metabolic rate increased, (iv) have a vulnerability to immune processes increased based on the electric pulses, cause heating or energy transfer through a cell membrane of the cell(s), (vi) deplete an energy or an ATP reserve of the cell(s), (vii) cause at least one of an osmotic imbalance or an ionic imbalance of the at least one cell, (viii) disrupt normal cellular processes dependent on a membrane potential of the cell(s), or (ix) deform and modify electrically sensitive proteins and structures on the cell membrane of the cell(s). A bioelectric response or at a cellular process(es) of the cell(s) can be disrupted on the electric pulses. Exemplary heating of the cell membrane can take place. Energy reserves of the cells can get depleted during course of pulsation.

A specific function of the cell(s) can be impaired based on a sign of at least one of the electric pulses. A creation of reactive oxygen species in intra-cellular or inter-cellular spaces of the cell(s) can be induced to degrade a cellular structure of the cell(s). The electric pulses can be applied using an electrode(s). A location to place the electrode(s) can be determined using (i) computed tomography, (ii) magnetic resonance imaging or (iii) ultrasound. The electrode(s) can include a plurality of electrodes which can be configured to be placed substantially near and away from the tissue(s). In some exemplary embodiments of the present disclosure, the electroporation of the majority of the tissue(s) can be prevented or reduced due to an effect of the electric pulses which have the particular parameters on the tissue(s). In certain exemplary embodiments of the present disclosure, the parameters can be based on a shape, a size, a biology or a morphology of the tissue(s). In some exemplary embodiments of the present disclosure, the tissue(s) can be ablated through mediation of a cell(s) membrane potential of the tissue(s) without crossing a threshold that can induce electroporation. The mediation of the cell(s) membrane can be induced using a plurality of charge discharge cycles. The tissue(s) can include a particular type of tissue. The tissue(s) can include a particular type of cells.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 6A is an exemplary map illustrating current density according to an exemplary embodiment of the present disclosure;

FIG. 6B is an exemplary map illustrating an electric field;

FIG. 15 is a set of exemplary images of exemplary electrodes according to an exemplary embodiment of the present disclosure;

FIGS. 19A and 19B are exemplary images of further exemplary electrodes according to a further exemplary embodiment of the present disclosure;

FIG. 22 is an exemplary electrode introduced through an exemplary catheter according to an exemplary embodiment of the present disclosure;

FIGS. 31A and 31B is an exemplary diagram illustrating exemplary ablation size and quality according to an exemplary embodiment of the present disclosure;

FIGS. 36A-36C are exemplary images of exemplary treatment areas according to an exemplary embodiment of the present disclosure;

Figure 1A:
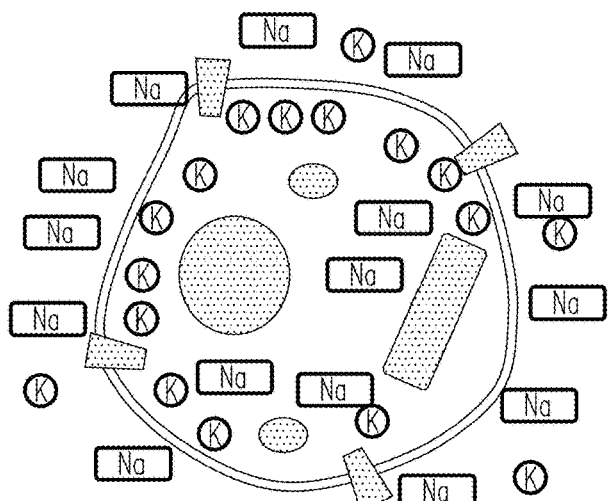
FIGS. 1A-1C is a set of exemplary diagrams of exemplary cells with characteristics that can be effected by the system, method and computer-accessible medium for in-vivo tissue ablation according to an exemplary embodiment of the present disclosure.
Figure 1B:
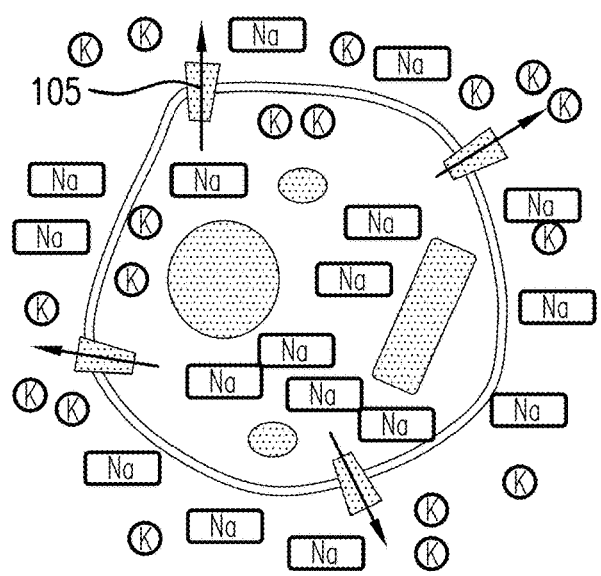
Figure 1C:
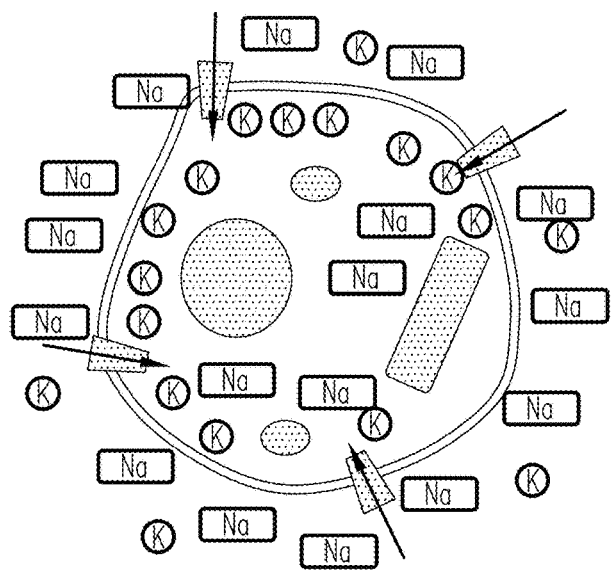
Figure 1D:
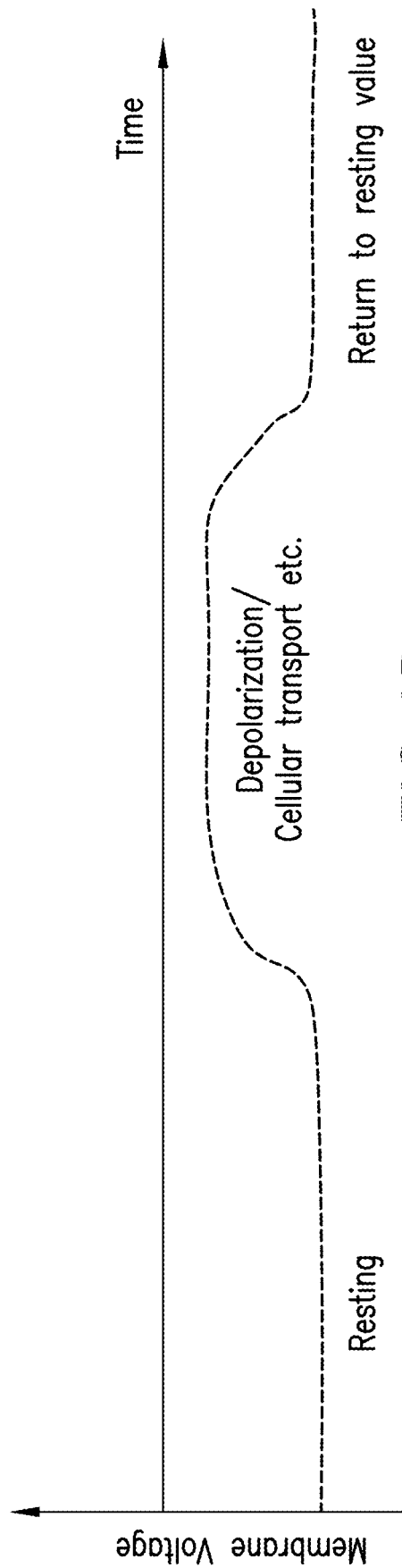
FIG. 1D is an exemplary graph illustrating the resting and return to resting value state of an exemplary cell.
Figure 2:
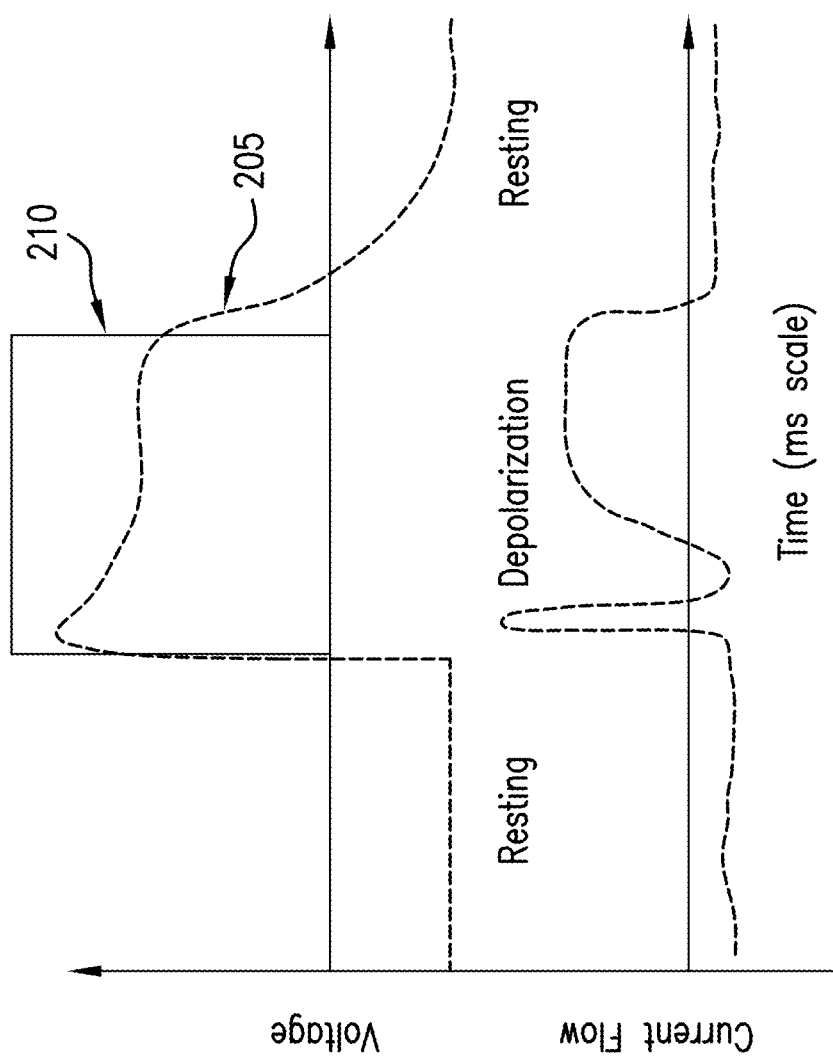
FIG. 2 is a set of exemplary graphs illustrating voltage and current flow of an exemplary electric field.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and described in appended claims.

DETAILED DESCRIPTION OF EXEMPLARY EMBODIMENTS

The exemplary system, method and computer-accessible medium, according to an exemplary embodiment of the present disclosure, can utilize bioelectric responses and cellular processes to perform a controlled injury, or to kill the cells. According to one exemplary embodiment, the ATP exhaustion can be induced in the cell if the external electric field can be applied for carefully pre-determined periods of time with timing such that the time between the waveform alterations can be sufficient to facilitate the cell to regain resting values before being hyper or depolarized again. Based on the sign of the electric field, the exemplary system, method and computer-accessible medium, according to an exemplary embodiment of the present disclosure, can be used to impair the functioning of specific ion channels. This can lead to loss of osmotic and ionic balance. Furthermore, the combination of ATP exhaustion and ionic imbalance can reduce the cell's ability to maintain membrane potential, and therefore, can disrupt basic cellular processes. This repeatedly induced external electric field can also cause mechanical damage to the membrane and other electro-sensitive structures. The generation of current flow through the cell can induce creation of reactive oxygen species ("ROS") in the intra and inter cellular spaces which can degrade cellular structures. The repeated passage of current through the cell can also be used to cause highly localized heating. This cascade of events, following exposure to an electric field, can cumulatively or separately cause the cell to lose viability and die. (See, e.g., FIG. 3).

Figure 3:
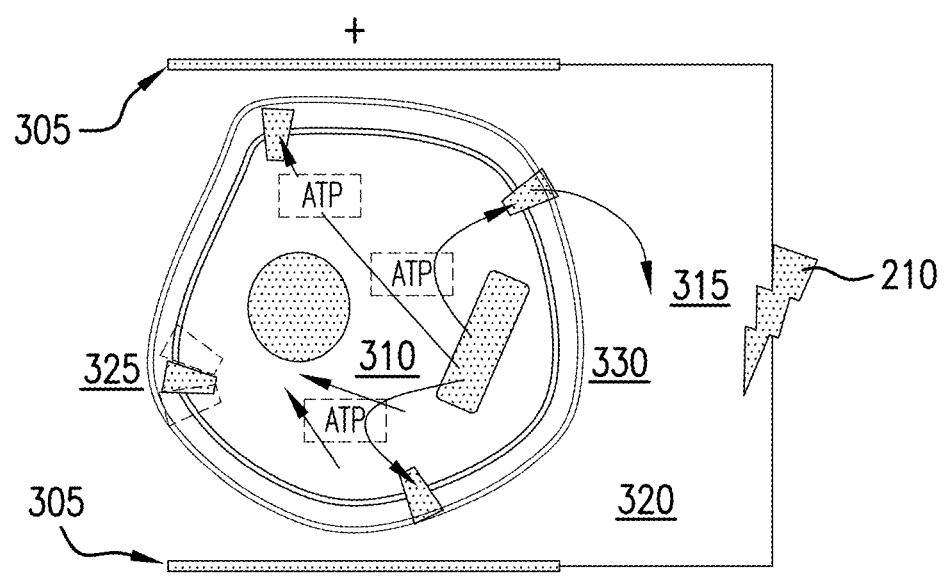
FIG. 3 is an exemplary diagram of an exemplary cell being ablated according to an exemplary embodiment of the present disclosure.

As illustrated in FIG. 3, a cell exposed to an external voltage 210 imposed upon it for a short duration of time using electrodes 305 in order to depolarize or hyperpolarize the cell can elicit a variety of reactions, which can include, for example i) ATP Exhaustion 310: where the ATP within the cell can be consumed in order to maintain osmotic balance and to regain the cell's normal resting membrane potential; ii) Ion Flow and Imbalance 315: the polarization can also lead to ion influx into the cell (e.g., $Na^{2+}$ or $Ca^{2+}$) and the loss of certain ions (e.g., $K^+$); iii) Reactive Oxygen Species ("ROS") Damage and Infiltration 320: the flow of current can induce an electrolysis and/or an ROS formation near the membranes; iv) Electro-Confirmational Protein/Gate/Channel Change 325: electrically sensitive membrane proteins, including cells having an abundance ion channels and gates, can undergo electric field induced deformation and damage; and v) Osmotic Swelling 330: the disruption of membrane potential can also lead to loss of homeostasis, which can lead to osmotic swelling.

Figure 4:
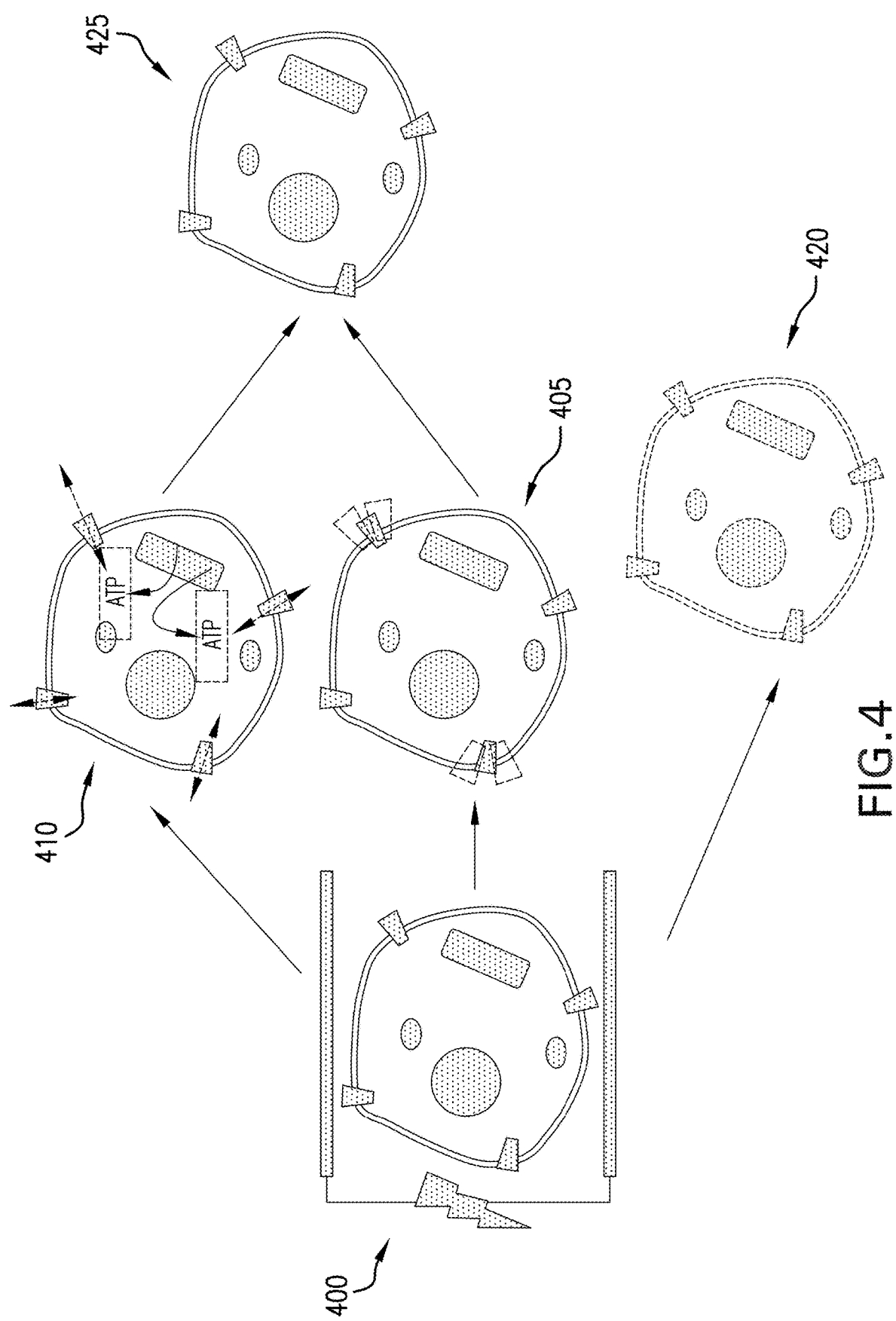
FIG. 4 is an exemplary diagram illustrating various exemplary stages of the exemplary ablation procedure according to an exemplary embodiment of the present disclosure.
Figure 5:
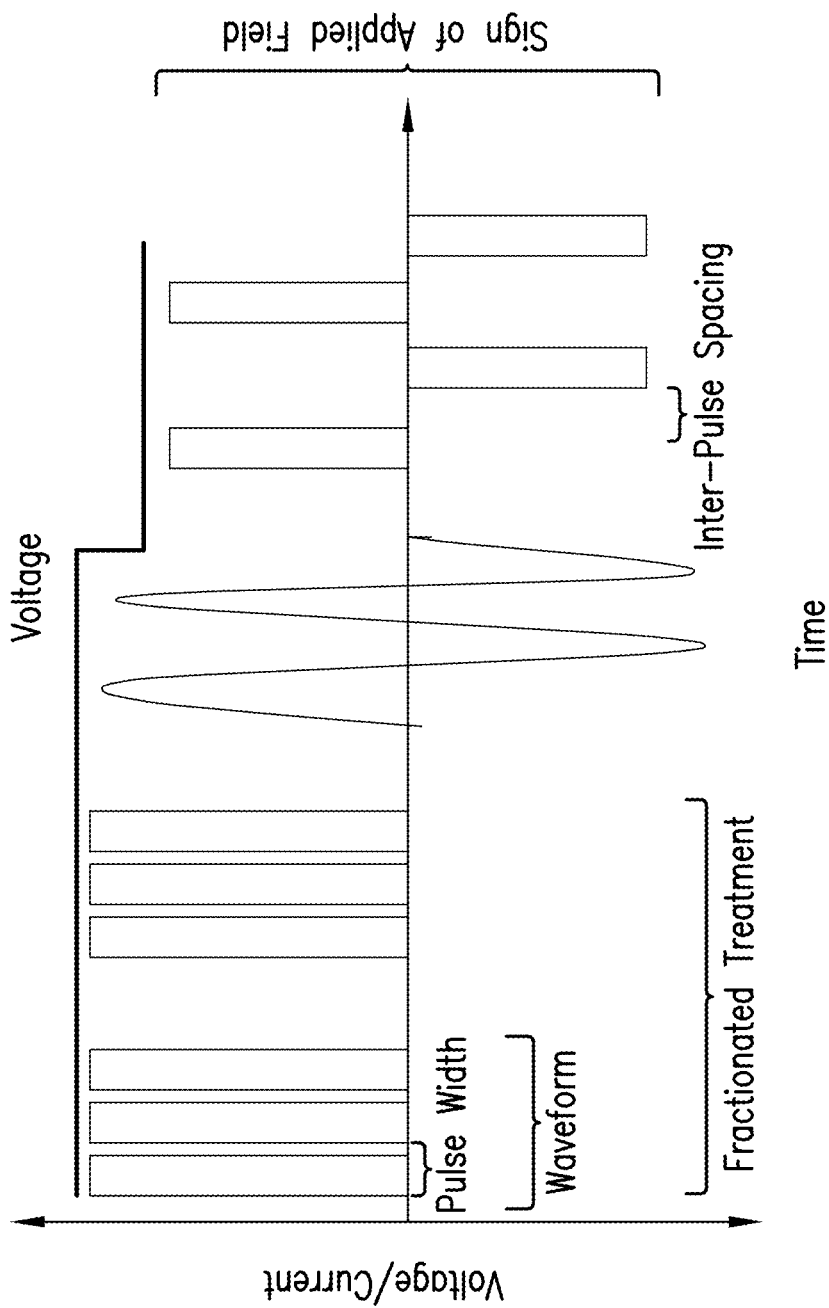
FIG. 5 is an exemplary graph illustrating an exemplary waveform according to an exemplary embodiment of the present disclosure.

This process can be defined to be electrically induced stress or EStress for short. EStress can operate as an in-vivo tissue (e.g., tissue type or cell type) ablation technique. Through the working principle of EStress (element 400), the waveform of the external electric field can induce one of several biological effects on cells in vivo including transient cellular injury (element 405), increased metabolic rates (element 410), increased vulnerability to immune processes and can also cause immediate and complete cell death (element 420). (See, e.g., FIG. 4). Cells from element 410 or 425 that can be exposed, e.g., to only a limited cycle polarization can typically survive and continue to function normally. The EStress waveform used to cause any of these effects can be carefully attuned to attain a specific outcome. The EStress waveform can be defined by several parameters including applied voltage, sign of the electric field, type of waveform, length of each exposures, relative field strengths and current density, duty cycle, and intermittent or repeat exposures. (See, e.g., FIG. 5). While similar waveforms can be in use for experimental techniques and other physiological processes, the selection of waveforms to induce EStress can be non-trivial. Incorrect choice of even one parameter can lead to undesirable or unexpected outcomes.

Exemplary Parameters for Estress

The voltage to be applied to achieve EStress can be based on the configuration of electrodes used, and the biology of the target cells. The size, shape and morphology of the cells can determine the threshold membrane potential induced on the cell. The exemplary transmembrane potential induced on exposure to an external electric field can be determined using the Schwann equation, where cell shape and size can be key determinant factors. The exemplary voltage applied upon the cells can be high enough to cause transient rise in membrane potential but can be lower than the electroporation threshold for the cell. While this can be based on cell type, representative values for mammalian cells can be the voltage that can cause increase in transmembrane potential in the range of about 100-300 mV. These values can likely be lower for larger skeletal muscle cells, and higher for smaller cells. Various exemplary statistical methods can be used to determine values for a population of cells where processes such as neoplasia or dysplasia can cause variations in the cell size and general morphology. For example, FIG. 6A illustrates a current density map 600 including electrodes 605 and an exemplary boundary of the effect of the Exemplary EStress 610. FIG. 6B illustrates an Electric Field Map 615 having electrodes 605 and a boundary of electroporation 620.

Figure 7:
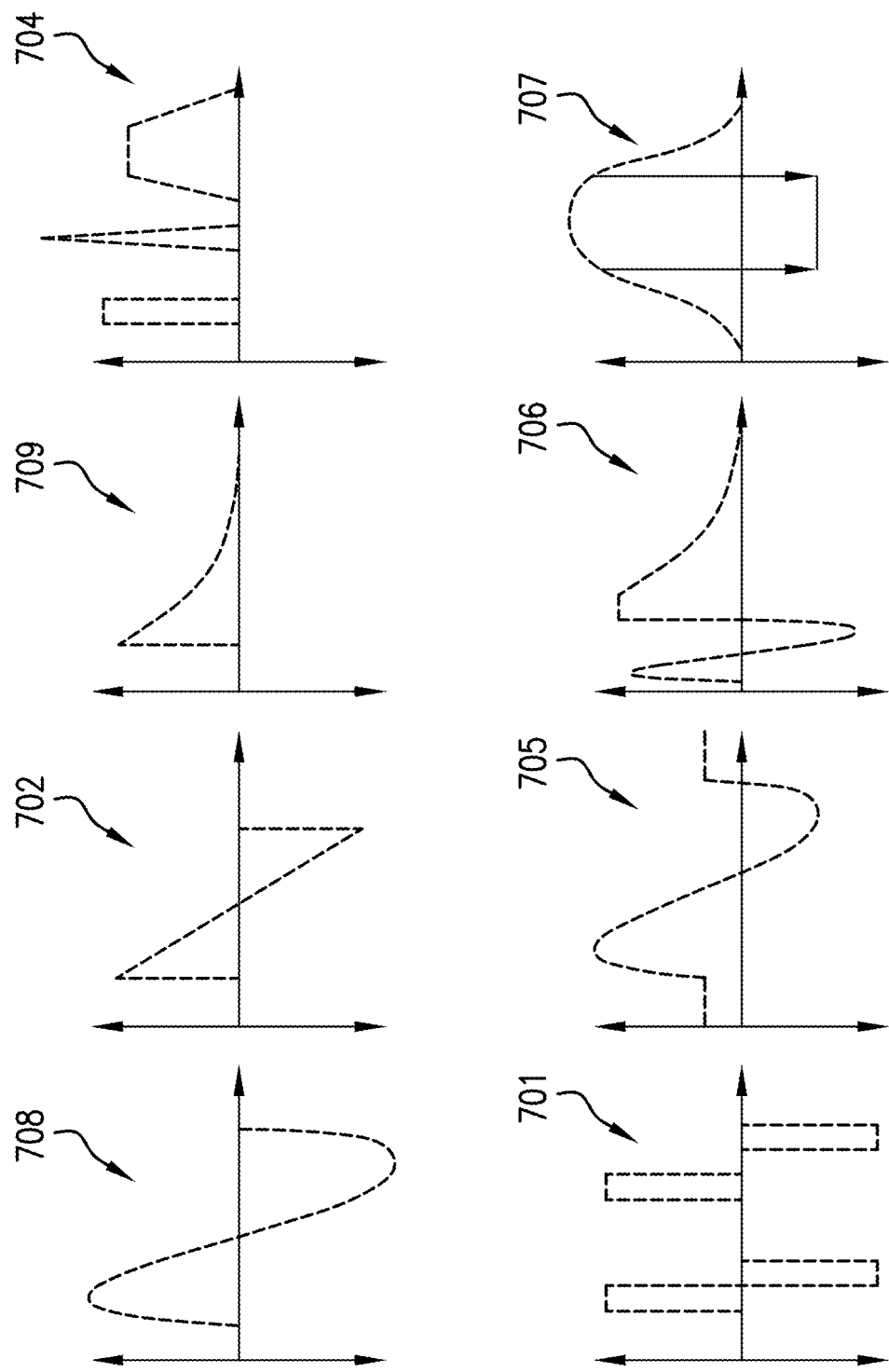
FIG. 7 is a set of exemplary waveform shapes according to an exemplary embodiment of the present disclosure.

The treatment voltage can be applied to the cell in a variety of waveforms, including square 701, sawtooth or triangle 703, trapezoidal 704, exponential or sinusoidal pulses 705-709. (See, e.g., FIG. 7). These waveforms can be applied to the cell in monopolar, DC shifted or bipolar fashions. In case of sinusoidal or similar waveforms, the frequency of application can be limited by root mean squared ("RMS") voltage value, which can be larger than the cell charging time. In case of monopolar application, the sign of the waveform can determine the predominant current channel affected by it, for example either inward or outward current, and also the type of ion depletion caused. (See, e.g., $Na^+$ or $K^+$). The exemplary waveform can be shifted from a positive to a negative direction, or vice versa, to maximize stress induced on the cell. The bipolar waveform can offer additional advantages such as reducing stimulation of non-targeted cells, which can lead to effects such as minimal to no nerve or muscle activation, for example. The DC shifted waveform can provide the benefit of low level heating and generation of reactive oxygen species that can increase the stress on the cell, making it more vulnerable to death or other extra-cellular processes. Transient localized hyperthermia can also provide the added benefit of reducing the voltage used to induce desired transmembrane potential. Other waveforms, such as exponential waves, can also be used to provide a gradient for driving ROS species towards the cell, and interfering with cell's ability to return to resting potential.

Figure 9:
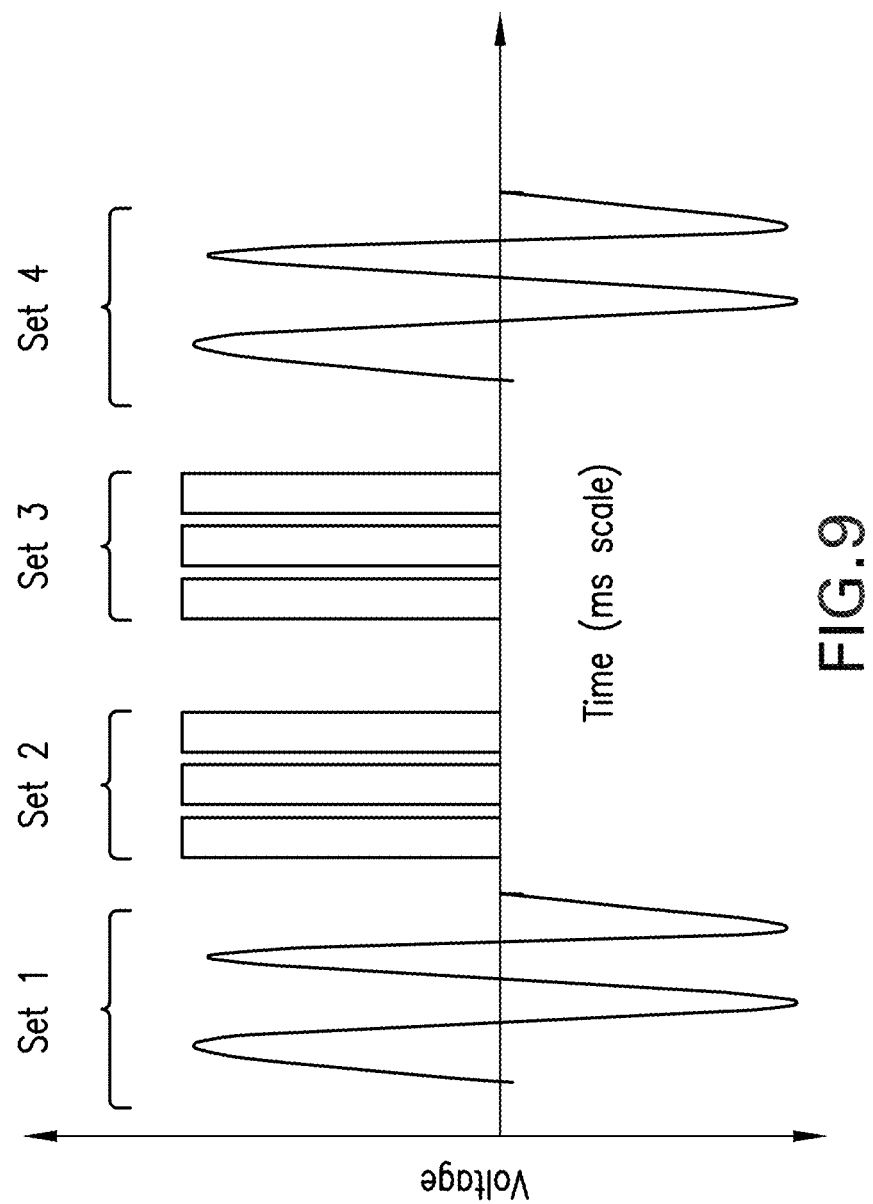
FIG. 9 is an exemplary graph illustrating an exemplary waveform according to an exemplary embodiment of the present disclosure.

A single exposure can be defined by the exemplary waveform that can induce increase of transmembrane potential to a desired value, and the period which can facilitate the cell to return to its natural resting state. The number of exposures that the cell goes through can be the primary determinant of the nature of injury to the cell. At optimal voltage values and without considering other expedient factors, it can be estimated that the cell can undergo at least 500-1000 exposures to cause permanent injury that can lead to eventual cell death. The number of exposures to achieve cell death can be based on the biology of the cell (e.g., ion channels present on the cell membrane), and/or its relative age and metabolism. Given a known cell type and optimal voltage value, empirical data can be used to construct a statistical model, like a Peleg-Fermi formulation, to determine the number of exposures that can be used to cause 99% or more cell death in a given population. (See, e.g., FIG. 9).

Figure 8:
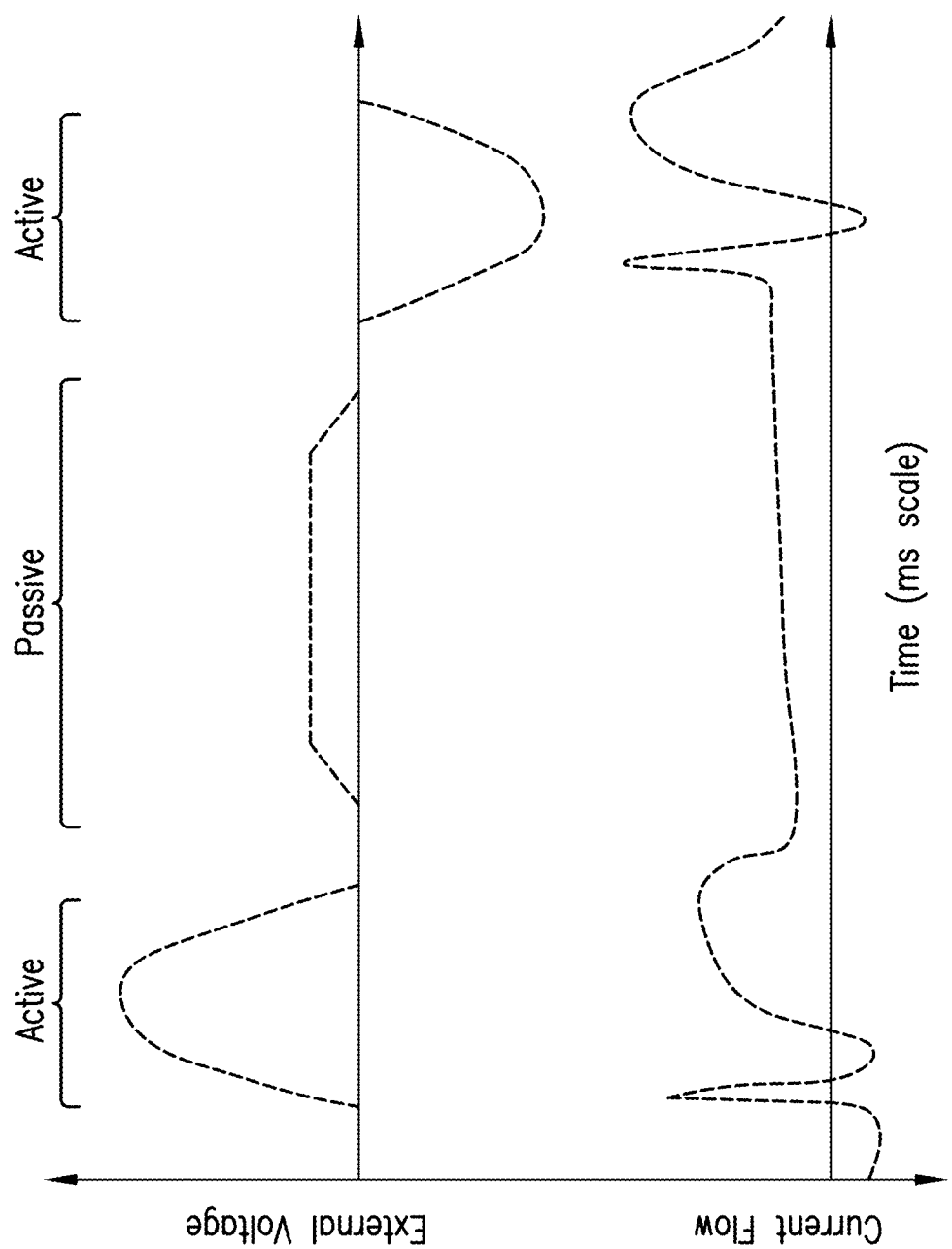
FIG. 8 is a set of exemplary graphs illustrating an exemplary waveform according to an exemplary embodiment of the present disclosure.

The exemplary waveform used to induce EStress in cells can be resolved into two functional components. At least one portion of the exemplary waveform, where the voltage can be applied to elevate the transmembrane voltage, can be called the "active" portion of the exemplary waveform, and the portion of the exemplary waveform where the external voltage can be turned off to facilitate the cell to return to resting values can be called the "passive" portion of the exemplary waveform. (See, e.g., FIG. 8). The active portion of the exemplary waveform can be longer than the membrane charging time of the cell, which can typically be between about 1000 ns to about 100 µs in length. In case of sinusoidal or similar waveforms, the half or quarter cycle/wavelength of the exemplary waveform can fall within this range. The actual active portion can be a smaller portion of about 100 µs, with the remaining portion of the exemplary waveform used to induce mild hyperthermia, generate ROS, cause electrophoretic or other effects. Conversely, the active portion can be optimized to provide a narrow range of temperature increase in the targeted area. The passive portion of the exemplary waveform can correspond to the time used by the cell to return to resting potential values from the elevated values due to exposure to the active portion of the waveform. The length of the passive portion can be dictated by the cell biology, and electrochemical transport processes. For example, this value can range from a lower range of about 10 µs for cells with rapid response time to about 100 ms for cells that can have slower processes. The passive portion can extend to many seconds for certain other cell types. The passive portion may not be constant, but can increase as the exposure progresses because of cell fatigue, and accelerating stress on the cell. The passive portion can also be monitored and altered to stop the buildup of membrane potential which can eventually lead to undesired electroporation of the cell.

The waveform can be applied to a target area continuously or as fractionated treatment. The fractionation can serve two purposes. (See, e.g., FIG. 9). First, fractionation can facilitate for the recovery of non-target cells which can undergo transient EStress because of proximity to treatment zone. Second, fractionation can facilitate pre-stressing of cells, where cells can be stressed by a first set of treatments, facilitating completion by following sets of treatment which can now be delivered at a lower energy setting. This fractionation can also be performed between sets of electrodes (e.g., spatially or temporally). During spatial fractionation, a set of electrodes can be used to surround a target that can be embedded well within non-target tissue that can be spared. In this case, each pair or set of electrodes can deliver a portion of the total desired energy. While the energy passes through non-target tissue, it can spare it from injury as it may only be a fraction of what can be used to cause cell death or permanent injury. However, in combination from all the electrodes, the target tissue can receive a larger and more complete portion of the energy leading to the desired treatment effect in this location only. The same effect can also be achieved by temporally fractionating the treatment, by either delivering treatment from a different pair of electrodes at different time points, or by a single set of electrodes but over different time points. (See, e.g., FIG. 10).

Figure 10:
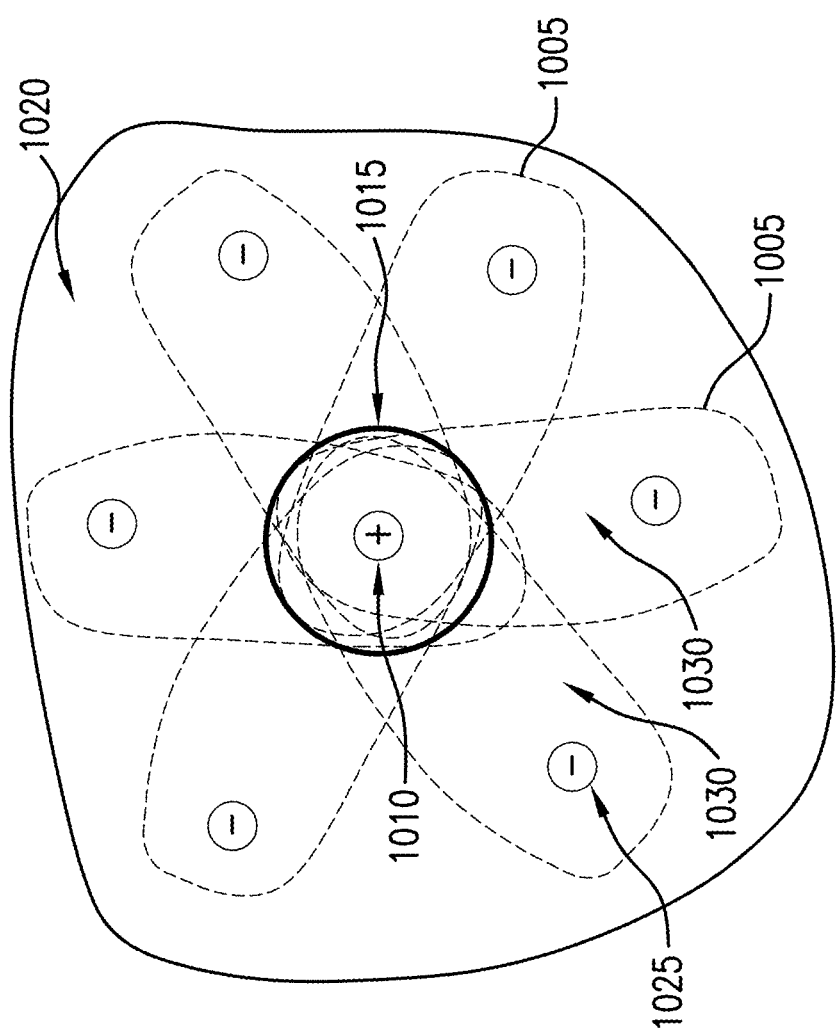
FIG. 10 is an exemplary diagram illustrating an exemplary ablation procedure according to an exemplary embodiment of the present disclosure.

The current density and field strength generated in a tissue experiencing EStress can be dependent on the applied voltage and the configuration of electrodes used. Globally, current density and field strength can be inter-related parameters, calculated by the applied voltage and electrical impedance of the target tissue. Unlike electroporation and related techniques like irreversible electroporation and supraporation which can be driven by target field strength, EStress can be mediated by current density imposed on the cells. The impact of EStress on a target tissue can in turn be determined by the total charge that can be moved through the cell, which in turn can be computed as the temporal integration of current density in the tissue over the course of treatment. The field strength and current density can be numerically computed by solving the Laplace equation of the voltage distribution over the domain of the target tissue. (See, e.g., FIG. 10). The exemplary EStress can utilize the exposing of a cell to a pre-determined sequence of exposures to electric fields. Cells in regions receiving fewer exposures that can be insufficient to induce cell death can be expected to survive (e.g., lines 1005). As shown in FIG. 10, EStress can be delivered using electrode pairs, where tissue 1010 surrounding the common current source 1010 can experience maximum exposure to electric fields, which can lead to tissue ablation 1015. The target tissue 1020 surrounding each current sink 1025 can experience only a fraction of the total exposures provided from the current source (see e.g., fractional Estress Zone 1030). Through this exemplary approach, maximum effect of EStress can be limited to a single region while sparing tissue in the surrounding areas.

Different types of waveforms can be combined to either enhance the effects of EStress or to achieve adjuvant effects. For example, radiofrequency waves can be combined prior to delivering the exemplary EStress waveform to use hyperthermia to increase the sensitivity of the cell to the effects of EStress. Alternately, the same effect can be achieved by a monopolar or bipolar square waveform. Waveforms or pulses typically used for causing electroporation can also be combined with EStress. For example, EStress can be used to alter the metabolic activity of the cell, following which electroporation can be used to introduce agents into the cell that can exploit the altered state of the cell. Additionally, exponential waveforms can be used to induce a combination of hyperthermia and ROS molecules that can further weaken the cell.

Exemplary Electrodes and Other Equipment

EStress can be induced, or treatment can be delivered to tissue or cells, through the delivery of electrical energy. This exemplary procedure, system, device, etc., according to an exemplary embodiment of the present disclosure, can use at least two electrodes, for example, one positive and the other for return pathway of the electrical current. Beyond this basic condition, the actual delivery of EStress to cells or tissue can be achieved through many different exemplary electrode arrangements. For in-vivo applications, this can be broadly classified into five exemplary approaches. The first exemplary approach can be a percutaneous approach where needles or long thin probes can be introduced into a target region through skin punctures. The second exemplary approach can be a catheter directed approach where long tubular probes with integrated electrodes can be delivered through bodily vascular other natural lumen to the target region. The third exemplary approach can be an endoscopic or laparoscopic approach, where natural or clinically created orifices or lumen used to direct specifically designed probes for therapy to a target region. The fourth exemplary approach can be a cutaneous approach where surface electrodes can be used to target regions that can be in proximity or at a superficial depth to the skin surface. The fifth exemplary approach can be one where a ring of electrodes can be deployed on the skin, in a non-invasive fashion, such that they surround a deeper target for therapy. Each of these exemplary approaches is described in further detail below.

Common to all exemplary approaches, therapy can be achieved by embedding or placing multiple electrodes in proximity of or surrounding a target, where at least one electrode can be positive and one other can provide a return path to the current. Alternately, the electrodes can also be paired, where each positive electrode can be paired with a corresponding return electrode. In this exemplary configuration, permutations of pairs can also be chosen ad-hoc to deliver EStress. The polarity of the electrodes can be alternated as treatment can progress to reduce electrochemical buildup. The alteration of polarity of the electrodes can also facilitate a reduced activation of electrically sensitive tissue such as nerves or muscles. Another exemplary configuration can be utilized when a multitude of current sources can be paired with a single grounding pad, or where the return path which can be attached on the skin surface distal to the treatment region. (See, e.g., FIGS. 11 and 13).

Figure 11:
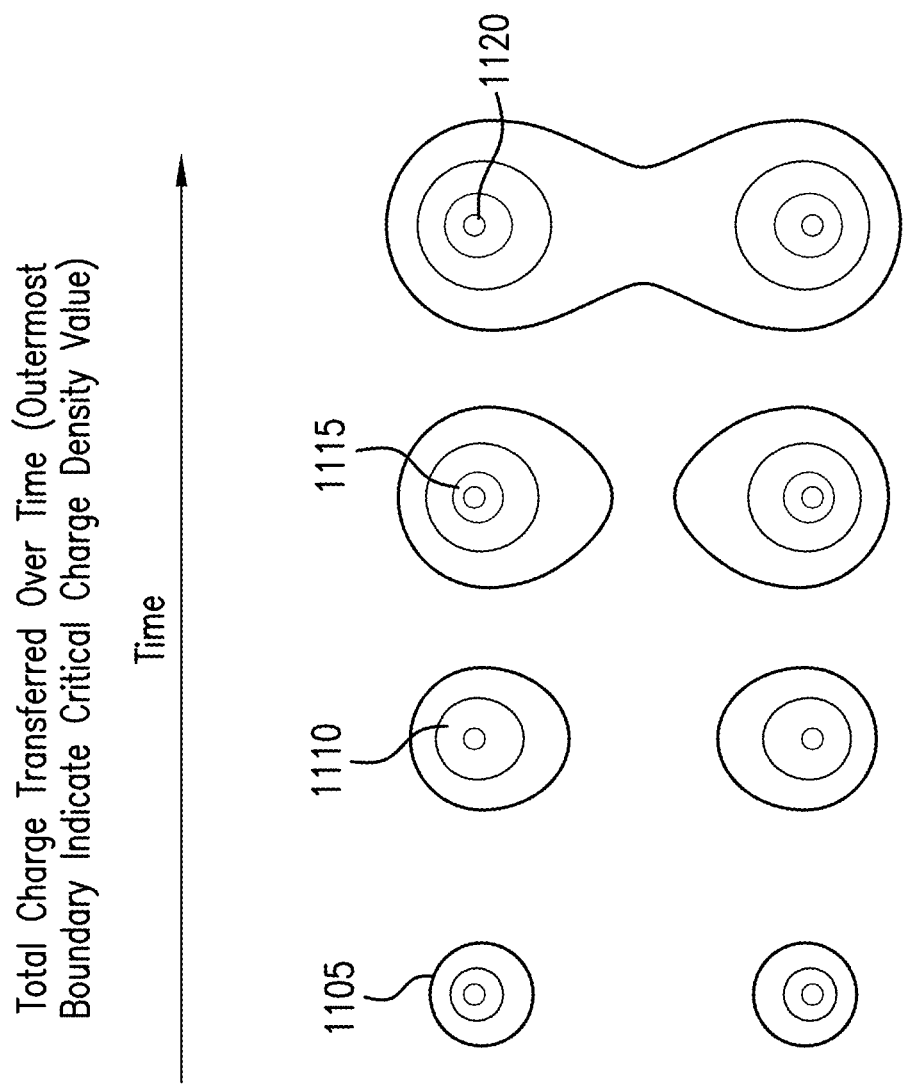
FIG. 11 is an exemplary diagram illustrating a total exemplary charge over time according to an exemplary embodiment of the present disclosure.

FIG. 11 illustrates that the total exemplary electric charge transferred through the target tissue can also be used to track the effectiveness of EStress for ablation. Element 1120 is the surface of the electrode from which the electric field can be deposited into the tissue. Element 1105 represents the boundary where the charge can pass through cells and where the number of exposures can be sufficient to ablate the cells. Elements 1110 and 1115 represent isolines of constant current density. The exemplary charge density of FIG. 11 can be expected to be highest in proximity to the electrodes, and therefore, cells at that location can be expected to undergo damage even with few exposures to the electric field. Repeated cycles can grow the boundary of injured/uninjured tissue, and can be used to achieve the desired volume of ablation.

Figure 12:
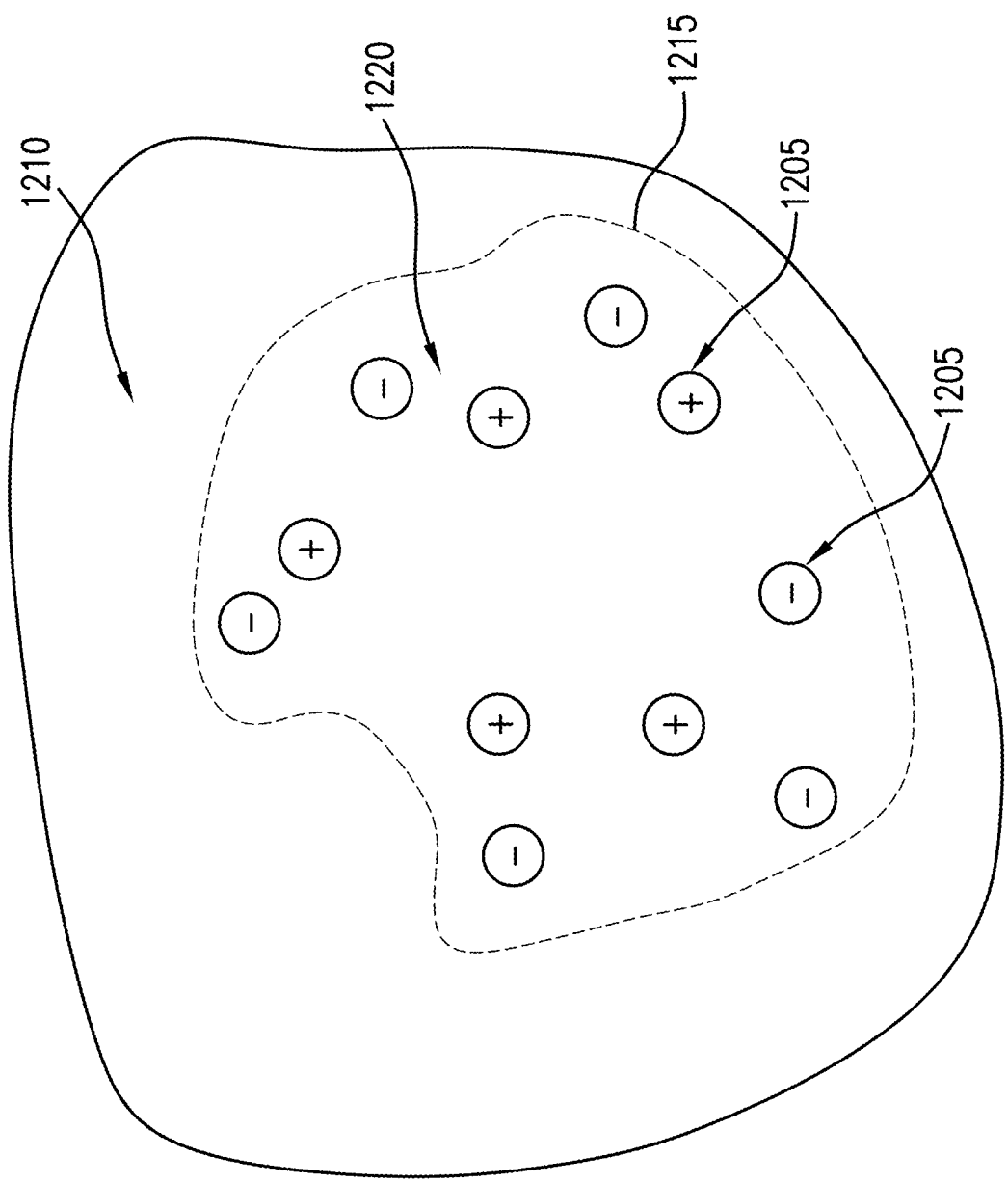
FIG. 12 is an exemplary diagram illustrating a further ablation procedure according to an exemplary embodiment of the present disclosure.
Figure 13:
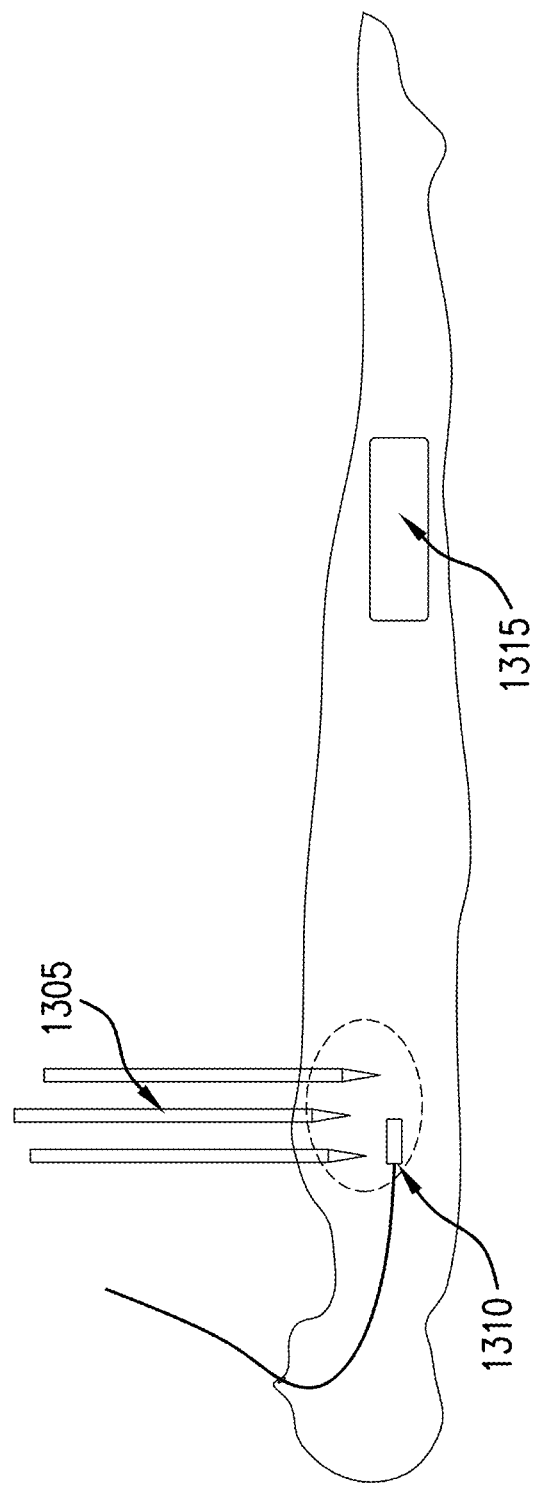
FIG. 13 is an exemplary diagram of an exemplary ablation procedure on a patient according to an exemplary embodiment of the present disclosure.

As illustrated in FIG. 12, the exemplary can be conducted using a multitude of electrode pairs 1205, where the current source and sink can be, but do not have to be equal in number. When an exemplary therapeutic waveform can be delivered with one pair of electrodes at a given time, the combination(s) of electrodes use for treatment delivery to untreated tissue 1210 can be varied to achieve any shape/volume of ablation (e.g., element 1215) in the exemplary treated tissue 1220. FIG. 13 illustrates a further exemplary configuration of the exemplary EStress. A varying number of needle electrodes 1305 can act as a current source 1310 (e.g., a catheter-directed electrode), and can be used in combination with a single distally placed ground pad 1315 to provide a return circuit.

Figure 14:
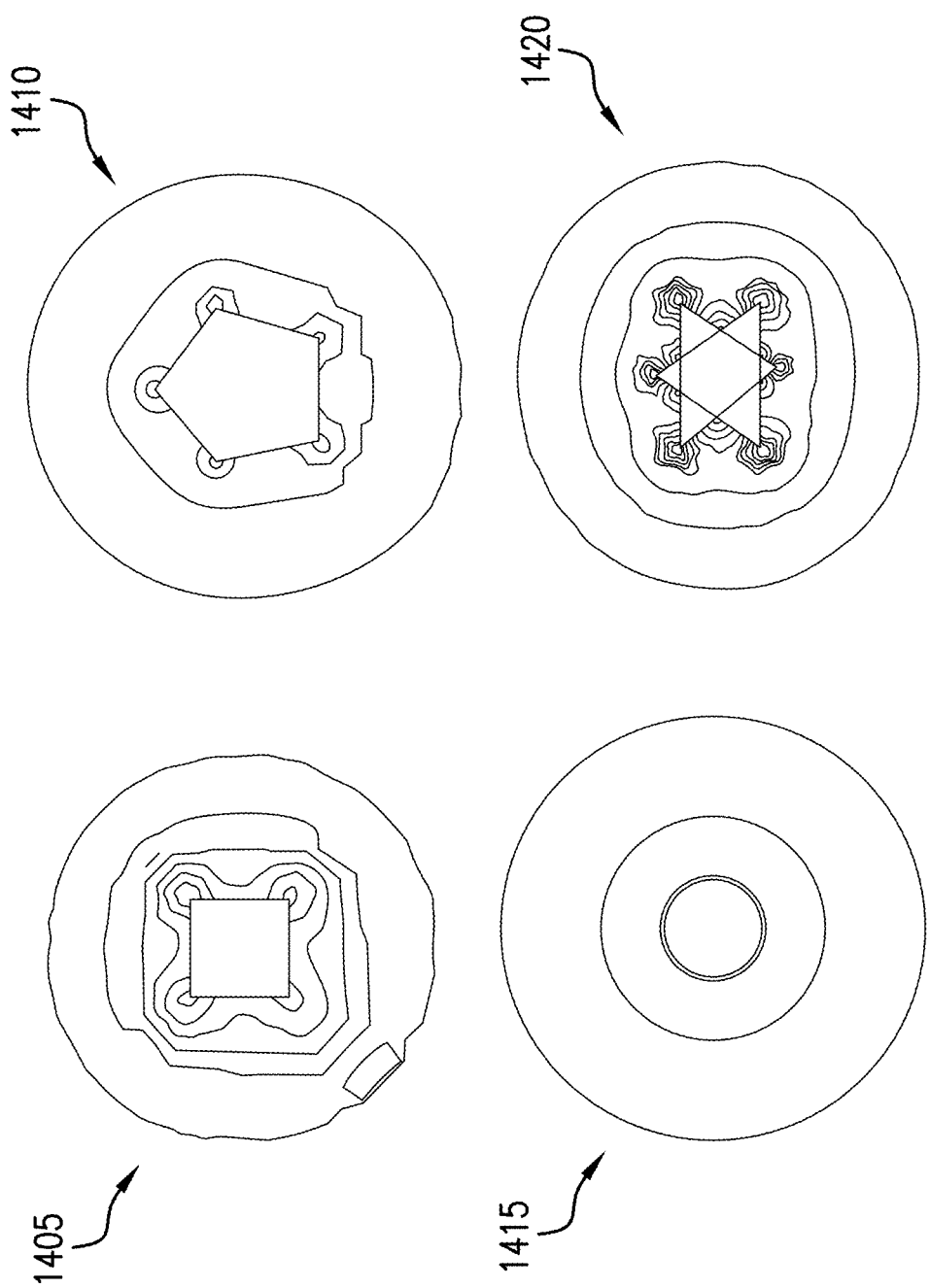
FIG. 14 is a set of exemplary diagrams of exemplary electrode cross-sections according to an exemplary embodiment of the present disclosure.

The distribution of current density, and the period over which the exemplary waveform can be delivered, can determine success of EStress. For a given set of electrical properties for a target tissue, the current density can be determined by the distribution of electrodes in the tissue, the cross sectional shape and geometry of the electrode, the relative position of the electrodes with respect to each other, and the distance between each source-ground pair. The current density at any point in the tissue can be numerically calculated solving the Laplace equation. (See, e.g., FIG. 14). The cumulative charge moved through a given cell, a factor of induced current density and the period over which the waveform can be applied can be used to determine magnitude of injury to the cell. This can be minor, transient or permanent.

Referencing the exemplary percutaneous approach, the probes can be designed as thin long needles with different prismatic cross sections which can be used to facilitate current density distribution in the surrounding regions (e.g., square 1405, pentagonal 1410, circular 1415 and/or star 1420). As illustrated in FIG. 15, percutaneous probes (e.g., insulated probe 1505) can also be tined, with the tines being used to enhance current distribution from current source 1510, create a faraday cage effect (e.g., through current return 1515) or to inject fluid media that can alter local conductivity properties to enhance the effects of EStress. (See, e.g., FIG. 15). Percutaneous probes can also be fashioned such that they can perform a core biopsy of tissue immediately followed by delivery of EStress treatment. (See, e.g., FIG. 16). The exemplary probes can be arranged in pairs with mathematical models used to determine treatment coverage, or they can also be arranged in a fashion such that a central source can be enclosed by a ring of ground or return electrodes. This latter exemplary configuration can facilitate the protection of electrically sensitive tissue just beyond the target zone from unnecessary stimulation. An integrated bipolar configuration can also be created for the percutaneous probe where both the source and return can be designed into a single probe device. This exemplary device can also follow a tined configuration where the tines can act as a ground, enclosing the target region with a homogenous dosage of EStress.

Electrodes can also be structured and/or configured for vascular or non-vascular endoluminal access. In either case, the exemplary electrodes can be distributed over a catheter like device, with at least one source and one return electrode. Alternately, the return electrode can also be a grounding pad that can be placed distal to the target or treatment region. (See, e.g., FIG. 17). The electrode on the catheter-like device can be provided using conductive wires in forms such as coils, baskets or tines. (See, e.g., FIG. 18). In these exemplary cases, the exemplary configuration of the electrodes can be fashioned to provide ablations with radial depth, or along a helical or longitudinal cross section of the lumen. In addition to these exemplary configurations, the electrode can be or can include a conductive substrate running the length of the catheter, or can be placed on a balloon that can be used to increase contact with the surface of the lumen. Alternately or in addition, the source and ground electrodes can be placed on two separate catheters that can be introduced to the target region separately. The endoluminal devices can be configured to achieve focal, spot, or circumferential lesions by altering the electrode placement on the catheter.

Figure 16:
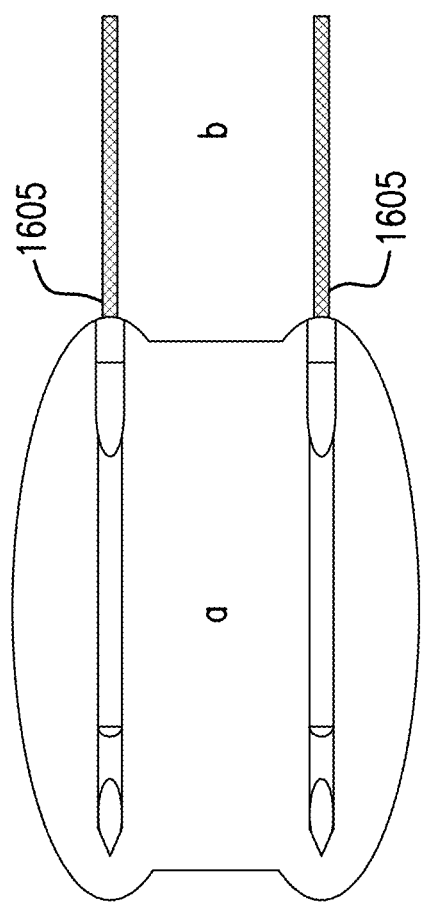
FIG. 16 is an exemplary diagram of a set of exemplary electrodes according to an exemplary embodiment of the present disclosure.
Figure 17:
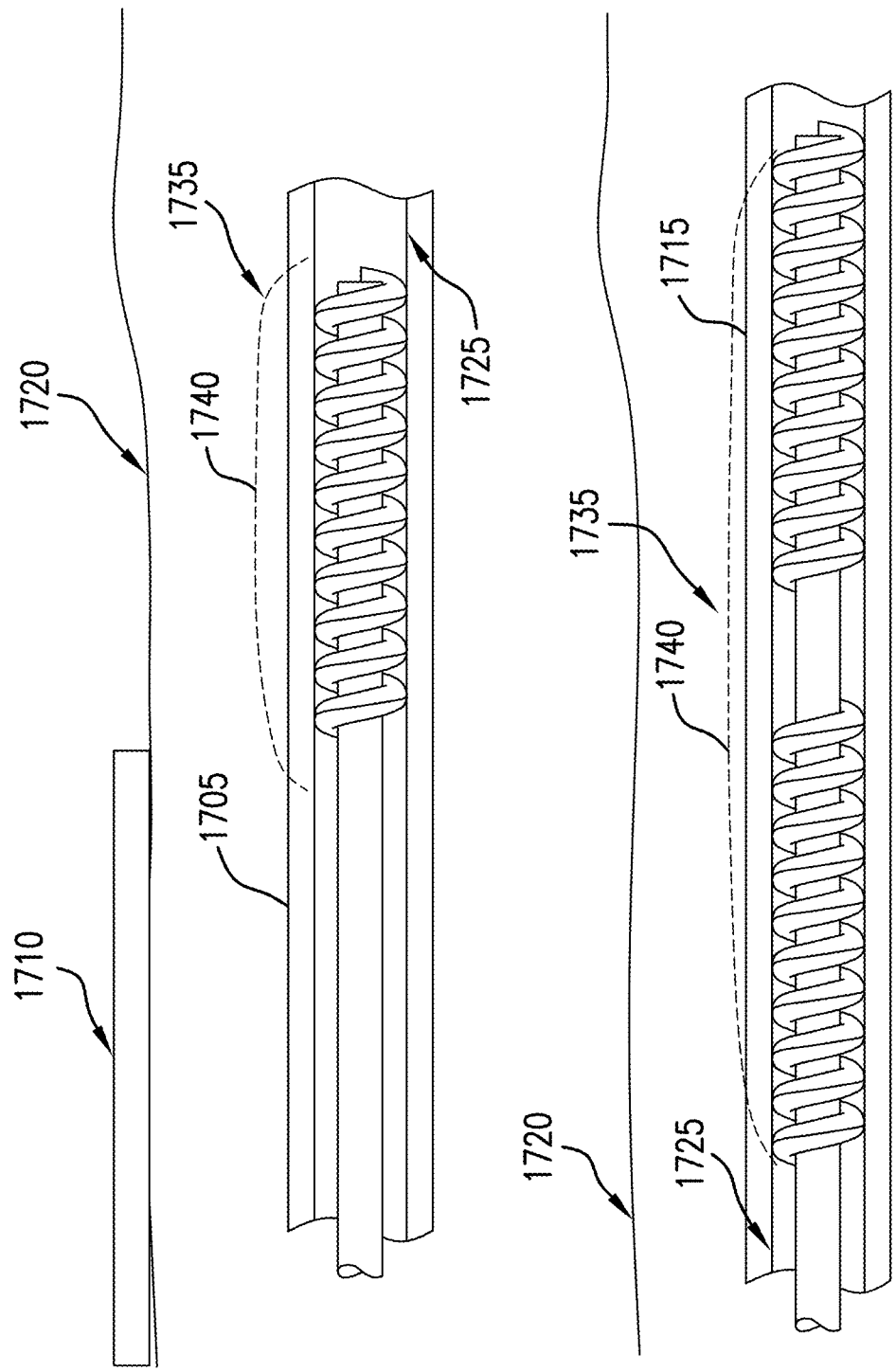
FIG. 17 is a set of exemplary diagrams of exemplary treatment areas according to an exemplary embodiment of the present disclosure.
Figure 18:
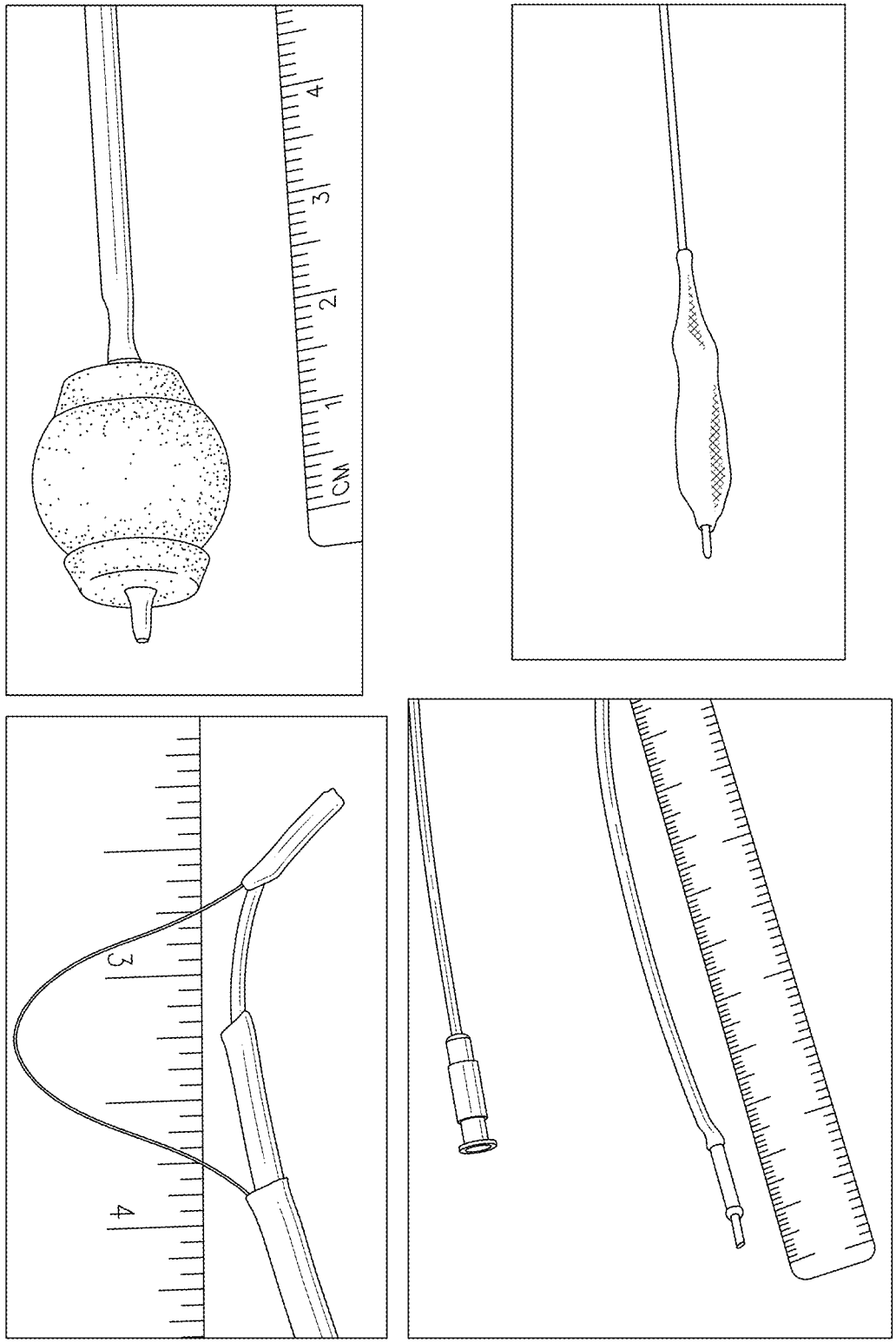
FIG. 18 is a set of exemplary images of exemplary electrodes according to an exemplary embodiment of the present disclosure.

FIG. 16 illustrates an even further electrode configuration where core biopsy needles 1605 can be modified to serve as electrodes for ablation. Ablation with EStress can be performed after biopsy to prevent needle tract seeding. In this exemplary configuration, the biopsy needles can be used for performing an ablation (a), while sparing surrounding healthy non-targeted tissue (b), and subsequently can be used to extract core samples for histological assessment. FIG. 17 illustrates an exemplary delivery of EStress using catheter electrodes where the catheter can function as either a monopolar electrode with a grounding pad 1710 (e.g., element 1705) or in a bipolar configuration (e.g., element 1710). The return element for completing the electric circuit (element 1710) can be placed on the skin surface 1720. Lumen wall 1725 can represent the target location upon which treatment is to be performed. This can include various endoluminal locations in the body (e.g., blood vessel, bile duct, gastrointestinal duct and urinary system). The expected treatment boundary 1735 achieved from application of pulses is illustrated by element 1740.

According to one exemplary embodiment of the present disclosure, catheters or similar flexible devices can be delivered to a target site using either percutaneous access or access established through natural orifices. In case of a natural orifice, the access can be established using a flexible endoscope, or some similar device, which can provide visual guidance to perform the procedure. In such exemplary cases, the electrodes that deliver EStress can be placed at the tip of long flexible devices to deliver the exemplary therapy. The tip can be in the shape of loops, button electrodes or flat surface applicators. Inner portions of large organs like the stomach, uterus and gut, and some other lumen, can potentially be targeted using this exemplary approach. Ablations can typically be directed on the surface of the organ with endoscopic visual guidance. This approach and configuration of electrodes can also be beneficial for use during laparoscopic or minimally invasive robotic surgery, where the probe with the electrode at the tip can be used to clear up margins of tissue surrounding the surgical region. Using EStress to perform this procedure provides the distinct benefits of preserving tissue integrity in the margins, and the ablation of tissue without emission of smoke or similar particulate matter. (See, e.g., FIGS. 19A and 19B). FIGS. 19A and 19B illustrate examples of laparoscopic friendly flexible electrodes. The electrodes (e.g., element 1905) can be mounted on a flexible shaft (e.g., element 1910) that can facilitate transport through a narrow working guide of a endoscopic instrument. The exemplary design can conform to the inner circumference of a lumen (see, e.g., FIG. 19A) to facilitate uniform ablation. The exemplary device can also be designed to deform and place the electrodes flatly against the target surface to direct ablation.

EStress can be applied for cutaneous or subcutaneous targets using various electrode configurations. When targeting skin protrusions, the target can be surrounded or captured using a pair of plate electrodes, or as part of a caliper electrode. This electrode configuration can minimize seepage of therapeutic waveforms or current into surrounding non-targeted tissue. For subcutaneous targets such as sweat glands or adipose tissue, EStress can be applied using fine needle arrays, where individual electrode needles can be of about 25 G or smaller in size. Needles in the array can be paired to provide localized treatment effects, or groups of needles can be assigned polarity to ablate a larger region. Alternately, in this exemplary configuration the needles at the boundary and the center of the array can be of an opposite polarity, facilitating capture of delivered energy within the targeted region. In other exemplary configurations, arrays of button or ring electrodes can also be employed to deliver electrical energy to the target region. (See, e.g., FIG. 20).

Figure 20:
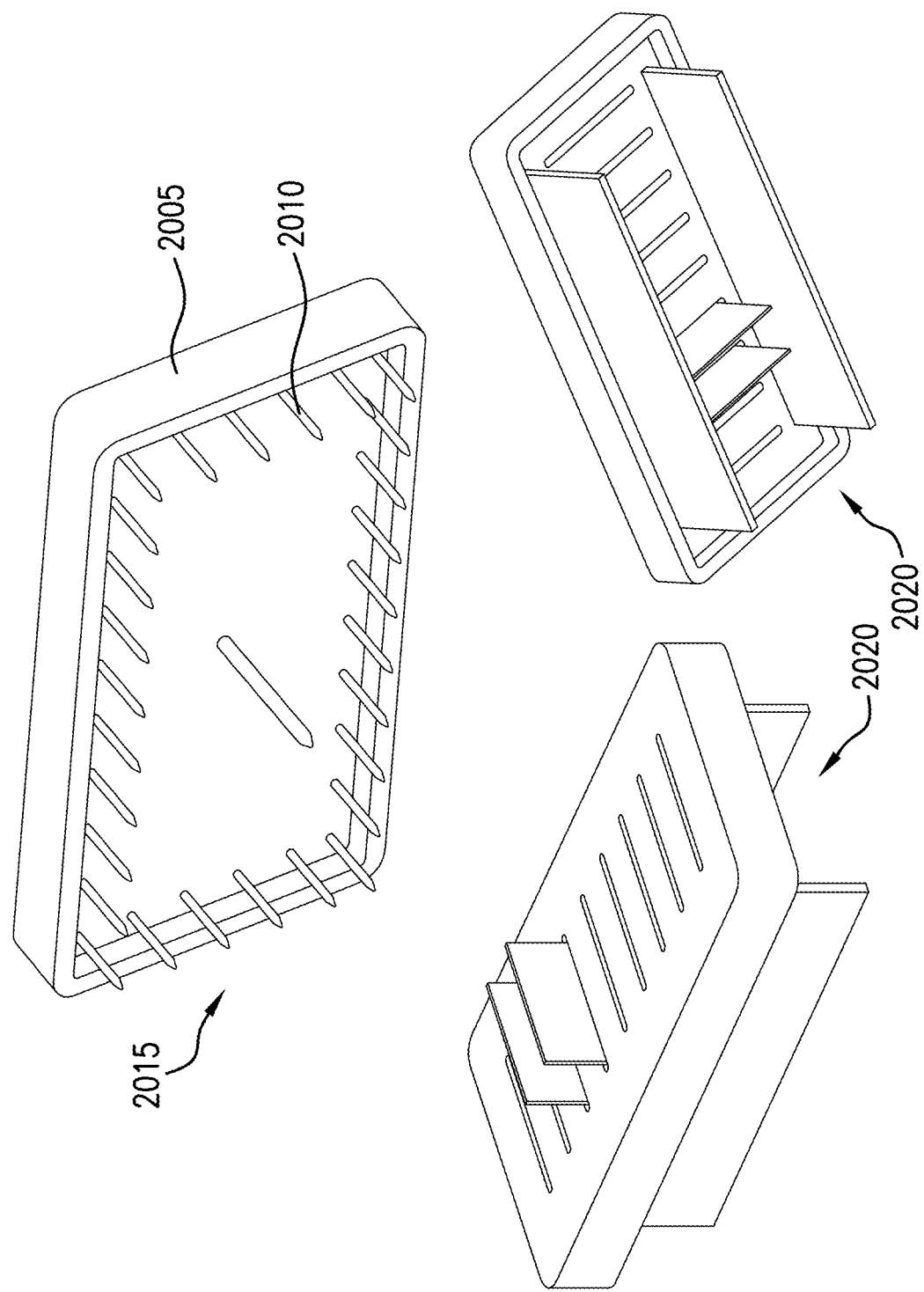
FIG. 20 is a set of exemplary images of still further exemplary electrodes according to another exemplary embodiment of the present disclosure.

FIG. 20 illustrates exemplary devices that can be used for subcutaneous delivery of the exemplary EStress. The body of the exemplary device (e.g., element 2005) can be constructed using an insulating material to support the electrodes (e.g., element 2010). The electrodes can consist of a number of current sinks in the periphery with a single central current source (e.g., element 2015), or the electrodes can be constructed as plate electrodes that can be repositioned to vary the size of the resultant ablation (e.g., element 2020).

Figure 21B:
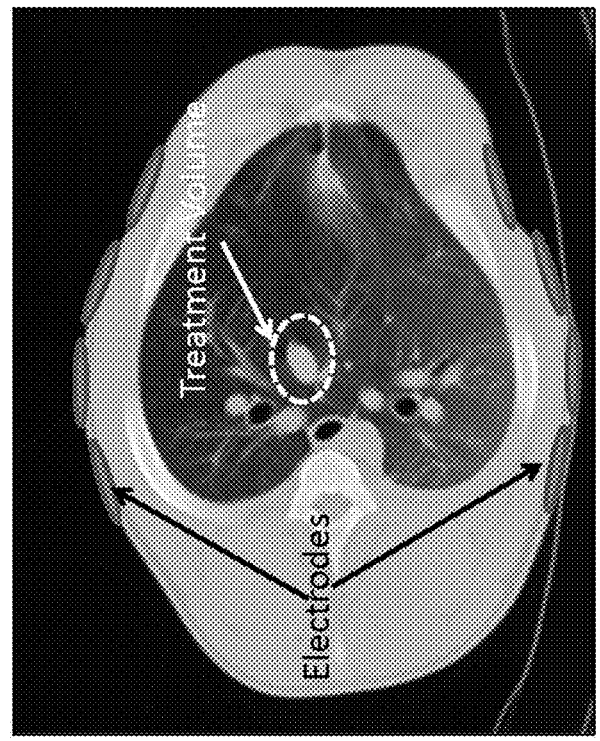
FIG. 21B is an exemplary image of an exemplary treatment area according to an exemplary embodiment of the present disclosure.

As described above, EStress can be amenable to summation of treatment energy in both temporal and spatial fashions. For example, a location deep in the viscera, such as a location within the brain or inside some solid organ such as the lung or the liver, can be targeted using a ring of electrodes placed on the skin surface such that they cumulatively form a perimeter or surround the target location. Ring, plate, gel or other forms of electrodes can be used create this configuration. In this exemplary configuration, EStress can be delivered between pairs or groups of electrodes such that the each group of electrodes can deliver a small portion of the total therapeutic dose of the energy waveform. The delivery could be sequenced such that all electrodes can be used within a finite period of time. Such spatial and temporal distribution of EStress can facilitate delivery of therapeutic energy through non-targeted tissue such that the target can receive the full dose of therapy, but surrounding non-targeted tissue can be completely spared of the effects, or can undergo only transient injury. Similar effects can also be achieved through percutaneous needles or subcutaneous electrode arrays that can be deliberately placed in a manner similar to that described above. (See, e.g., FIGS. 10, 21A and 21B).

Figure 21A:
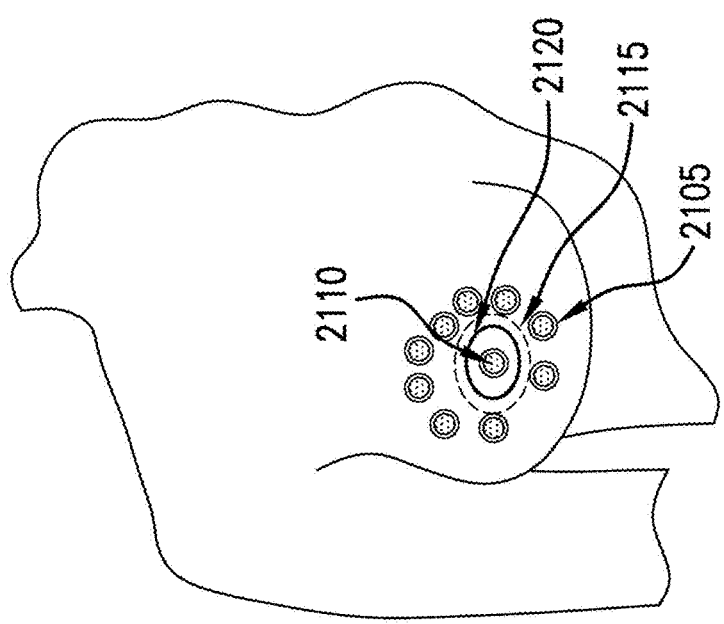
FIG. 21A is an exemplary drawing of an exemplary treatment area according to an exemplary embodiment of the present disclosure.

As illustrated in FIG. 21A, a number of current sinks 2105 (e.g., which can be placed subcutaneously) can be combined with a single current source 2110, to be placed within the target area 2115, can be combined to achieve a targeted ablation while sparing tissue under the current sinks. A tumor 2120 (e.g., a deep seated tumor) can be targeted using a multitude of current sinks 2105 and current sources 2110 placed on the skin surface. Ablation can be achieved by distributing fractions of exposure between different pairs of electrodes.

For a known biological target and tissue type, the exemplary mathematical procedures can be used to precisely plan the dose of EStress to a given target while entirely sparing, or only transiently injuring, surrounding non-targeted tissue.

The effects of EStress can be modulated by agents and chemicals that can be introduced during the therapeutic procedure. These agents can alter the local biology, or influence overall electrical properties in the targeted region to facilitate EStress, or in other exemplary cases, to protect non-targeted tissue. For example, wet electrodes can be created and/or provided by introducing saline of a different tonicity to modulate the delivery of EStress into a large lumen such as colon, esophagus or bronchus. The use of the wet electrode can protect the lumen from thermal effects that can arise due to direct tissue contact with a metal electrode delivering large values of current. Additionally, the fluid used to create the wet electrode can also be used to induce effects such as osmotic shock, or agents in the fluid can be used to protect one region of the tissue while facilitating deeper penetration of the therapeutic energy. In addition, chemical compounds, such as ion channel blockers, or other pharmaceutical agents, can be used as part of the wet electrode to improve targeting of a select set of cells using EStress. Similar wet electrodes in the form of a conductive gel can also be used with subcutaneous electrodes to improve targeted delivery of EStress to targets on the skin. (See, e.g., FIG. 22). FIG. 22 illustrates an exemplary device 2200 (e.g., using a catheter) that can be used to deliver the exemplary EStress to a treatment zone 2205 by using into a bodily lumen 2210 where a permeable balloon 2115 (e.g., a weeping balloon) can be used locally deliver a medium 2120 (e.g., a fluid) that can modulate the EStress treatment zone.

Figure 23:
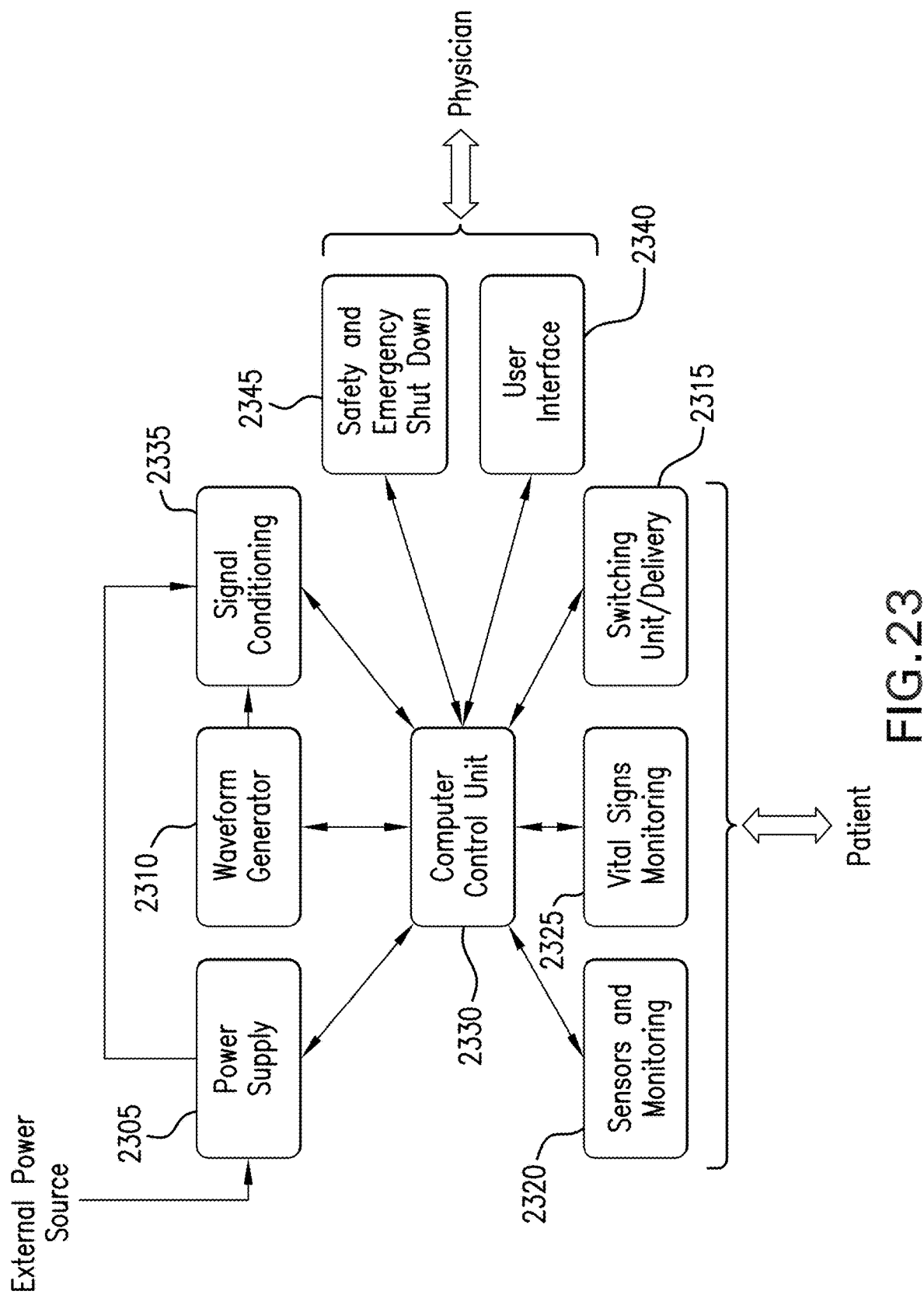
FIG. 23 is an exemplary block diagram of an exemplary ablation device/system according to an exemplary embodiment of the present disclosure.

As illustrated in FIG. 23, exemplary circuitry used for generation of the exemplary EStress waveforms can include electrical equipment capable of generating sustained power high voltage waveforms (e.g., through exemplary power supply 2305). This can be achieved through multiple procedures, including use of a step up transformer coupled with an arbitrary waveform generator 2310 and a rectifier circuit, or a combination of a capacitor bank and fast acting switches 2315. Current and power monitoring circuitry can be built in to the generator 2305 to ensure that the waveform generated can be specific to the desired EStress effect. A number of sensors 2320 and 2325 can be used to monitor and to modulate or control the EStress waveform being delivered using computer control unit 2330 in combination with signal conditioning unit 2335. This can include temperature sensors to regulate or minimize thermal effects on sensitive structures, and electrical impedance or conduction circuitry to track or control the effect of the exemplary waveform from EStress as compared to other effects such as thermal ablation or electroporation. The exemplary Estress can be controlled through an exemplary user interface 2340, and can further include an exemplary safety and emergency shutdown unit 2345 to shut off the exemplary Estress apparatus during an emergency. For example, the electrical impedance measurements can be performed across electrodes deployed in the target region using test pulses delivered prior to therapy. The test pulse can be used to perform a frequency sweep of the target region, and coupled with tissue specific information, can be used to estimate the energy levels at which EStress can be applied to achieve only desired outcomes. During treatment delivery, the same circuitry can be used to track the generation of EStress specific effects. This can manifest as two sets of current measurements, one during the active portion of the waveform and the other during the passive portion of the waveform. The current drawn from the circuit during the active portion of the waveform can be mathematically described as a decreasing exponential curve in shape, and can be analyzed accordingly. The current in the circuit during the passive portion of the waveform can be a non-linear curve that can be based upon the polarity of the active waveform and type of cell being treated. However, the magnitude of the passive portion current recorded can be, for example, 2-3 orders of magnitude smaller than the one measured during the active portion. If sufficient quantity of cells in the target region can be killed, then the current measured during the passive portion of the treatment can decrease significantly. This can be used as an added estimate of tissue ablation progress.

The exemplary equipment used to generate and deliver EStress can also be coupled with a neural and/or cardiac sensor apparatus to enhance safety of delivery. The neural sensors can be coupled to nerves in regions adjacent to EStress delivery to monitor undesired nerve activation, and to regulate the waveform amplitude or frequency to reduce such effects. A cardiac sensor, such as, for example, electrocardiogram ("ECG") systems, can be coupled with the generator to facilitate EStress treatment close to the heart, or other such sensitive tissues without causing atrial fibrillation or otherwise impacting the cardiac rhythm. The delivery system can also incorporate electrical circuitry, such as current measurement systems, to estimate the magnitude of charge delivered to the target tissue, and also to follow the graph of power drawn to determine normal delivery of therapy. (See, e.g., FIG. 24).

Figure 24:
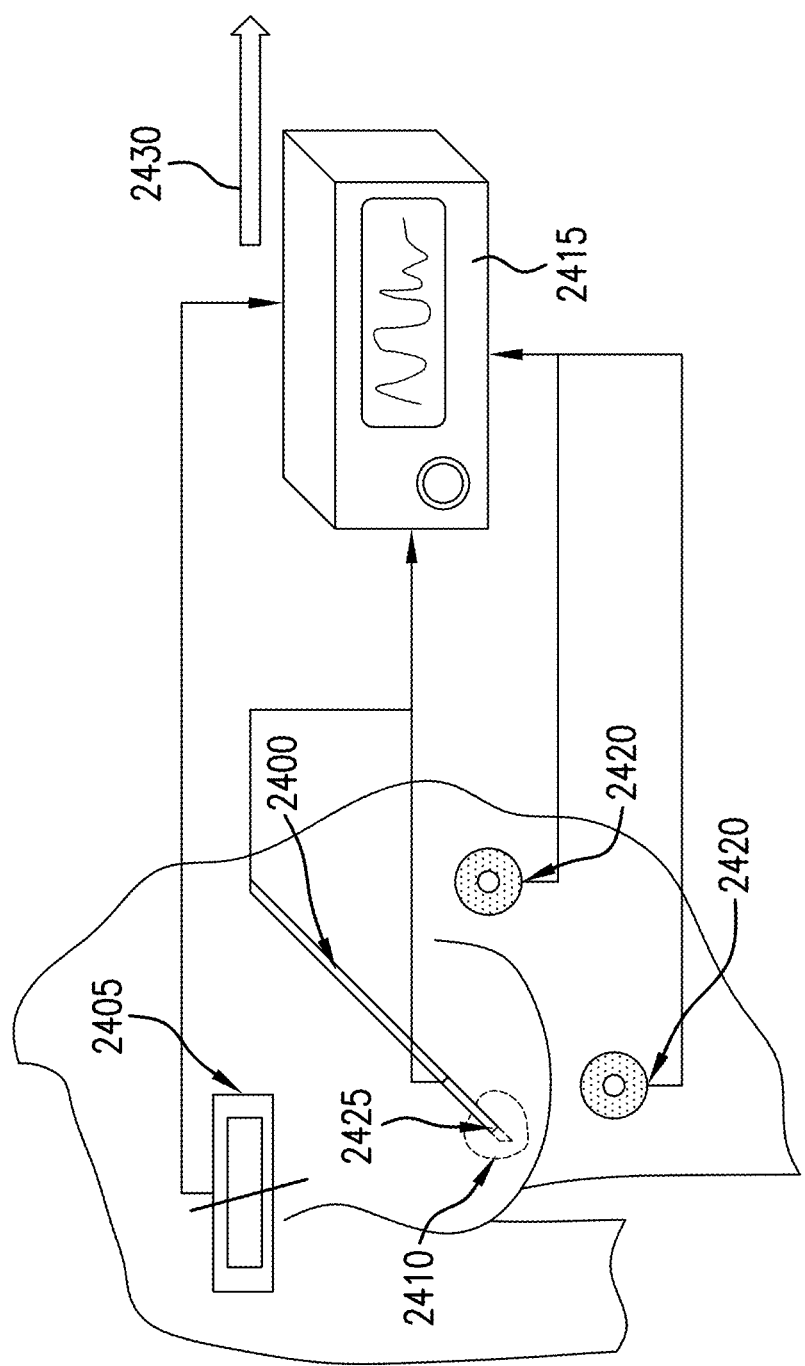
FIG. 24 is an exemplary diagram of an exemplary treatment area and the exemplary ablation device/system according to an exemplary embodiment of the present disclosure.

As shown in FIG. 24, the exemplary EStress ablation delivery (e.g., through needle electrode 2400) can be monitored and synchronized with sensors to achieve optimal treatment outcomes. For example, a nerve monitor 2405 can be used to identify any neuromuscular activation during energy delivery to target tissue 2410 and a sensor gating unit 2415 can adjust energy parameters to minimize such effects. ECG Sensors 2420 can be used to minimize unwanted cardiac effects. The electrode delivery of EStress can include a multitude of sensors 2425, which can include a current monitor (e.g., for tracking ablation progress), temperature probe (e.g., for adjusting treatment in the event of excessive temperature rise) and/or a physiologic function monitor. The above configuration and/or procedure can be controlled through a connection to and/or via a computer/power unit 2430 (or a plurality thereof).

In addition to the generator, the EStress delivery system can include a computer driven graphical or control interface that can facilitate the user to select parameters specific to target tissue biology for specific EStress mediated outcomes. The control interface can also feature switches that can be used to commence and stop delivery of therapy, and a kill switch that can be used to safely shut down of the system in case of adverse events. The system can feature exemplary modules that can facilitate rapid connection and disconnection of wires and electrodes used for treatment delivery. The graphical interface can facilitate treatment planning using one or multiple previously described mathematical models, and facilitates the user to use computed tomography ("CT"), magnetic resonance imaging ("MM"), ultrasound or other imaging modalities to plan relative electrode location. Additionally, the graphical interface can provide the operator with useful feedback regarding the progress of EStress in the target tissue.

Various imaging modalities can be used for the planning, treatment delivery and post-treatment confirmation following EStress in in-vivo tissue. For example, CT, Ultrasound, positron emission tomography ("PET"), MM, optical imaging, endoscopy, fluorescent imaging, fluoroscopic techniques and other modalities can be used for identifying tissue and performing calculations used for the delivery of EStress. Cells that can be lysed by effects of EStress can undergo acute necrosis which can immediately be identified using contrast enhanced CT imaging. Additionally, the loss viability can alter the diffusion and perfusion properties in the treated region, facilitating the use of multi-parametric magnetic resonance ("MR") imaging for confirmation of treatment. Compared to baseline values, EStress can induce brief spikes in the metabolic activity of target cells, and this can be captured using exemplary PET imaging techniques. The volume of current passed through tissue during EStress can be readily monitored using Redox or potentiometric chemical sensors, and can subsequently be imaged using exemplary optical or fluorescent techniques. EStress can cause transient erythmeia and hyperemia when treating luminal targets. Such changes which can typically be indicative of treatment can be monitored using simple endoscopic techniques.

Figure 25:
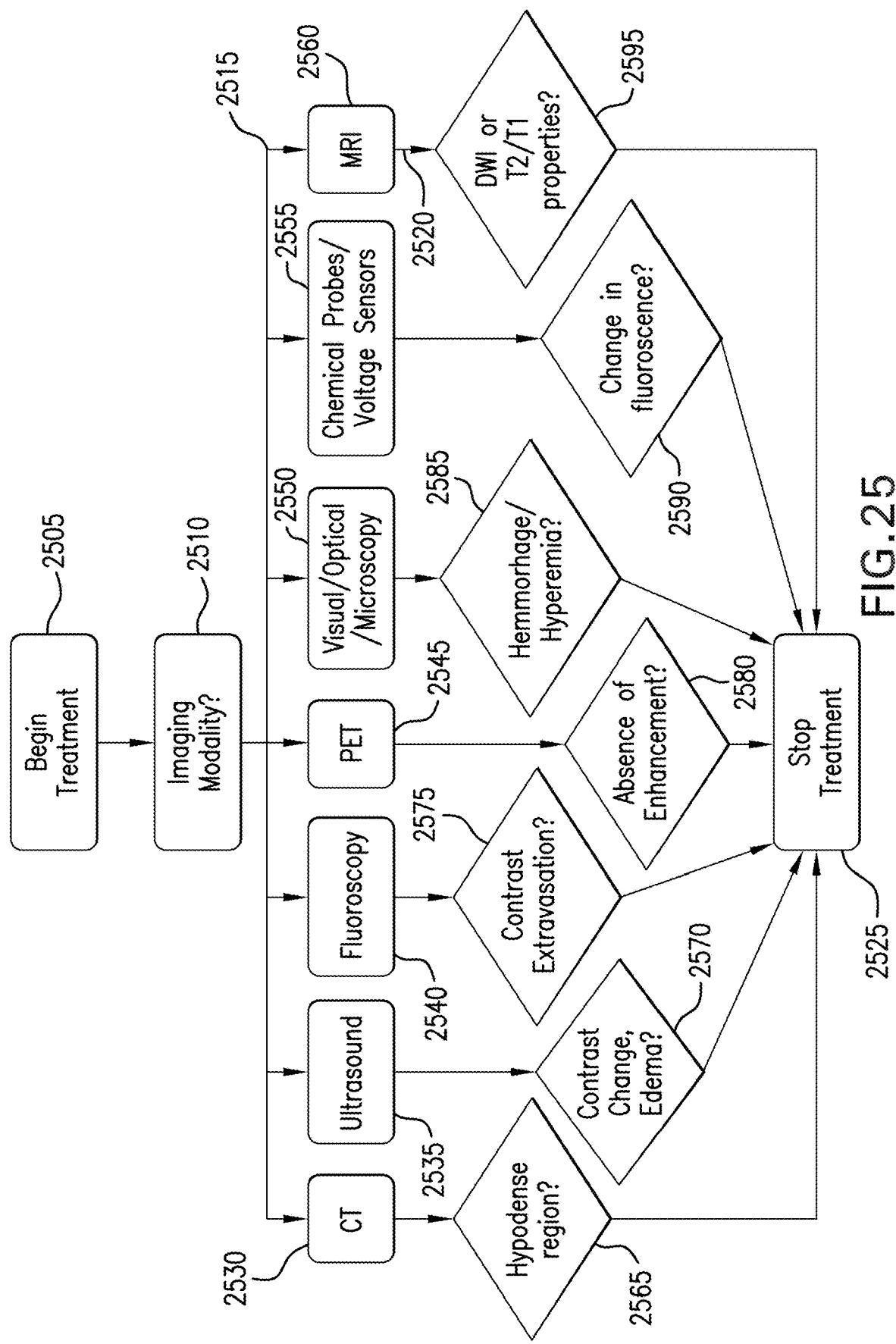
FIG. 25 is a flow diagram of an exemplary procedure for ablating an exemplary treatment area according to an exemplary embodiment of the present disclosure.
Figure 26B:
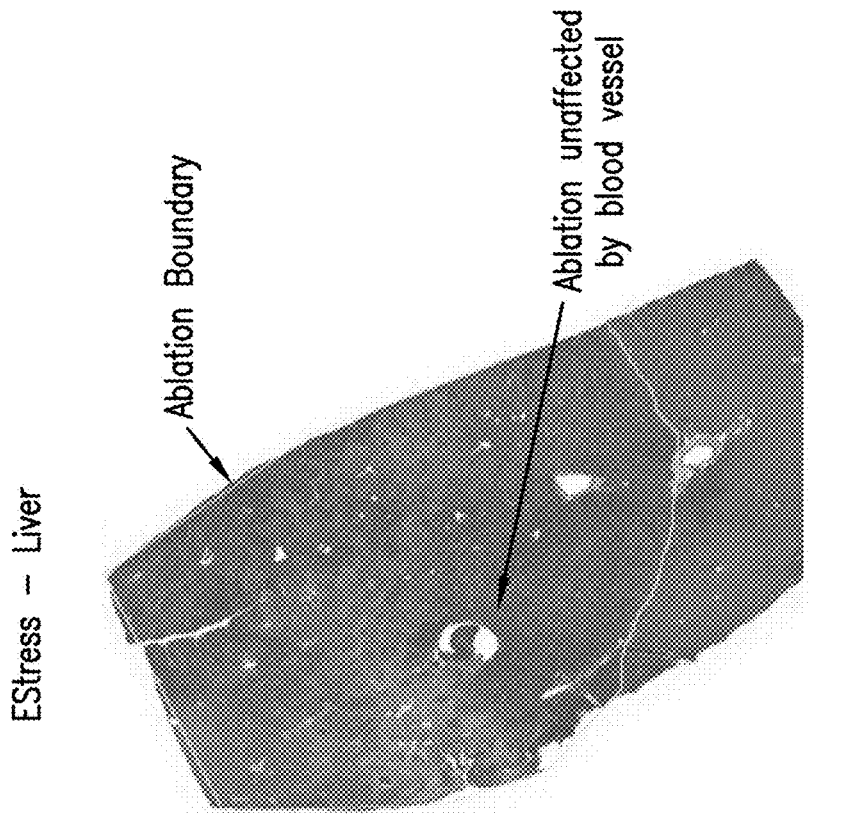
FIG. 26B is an exemplary image of an exemplary EStress treatment area of the liver according to an exemplary embodiment of the present disclosure.
Figure 26A:
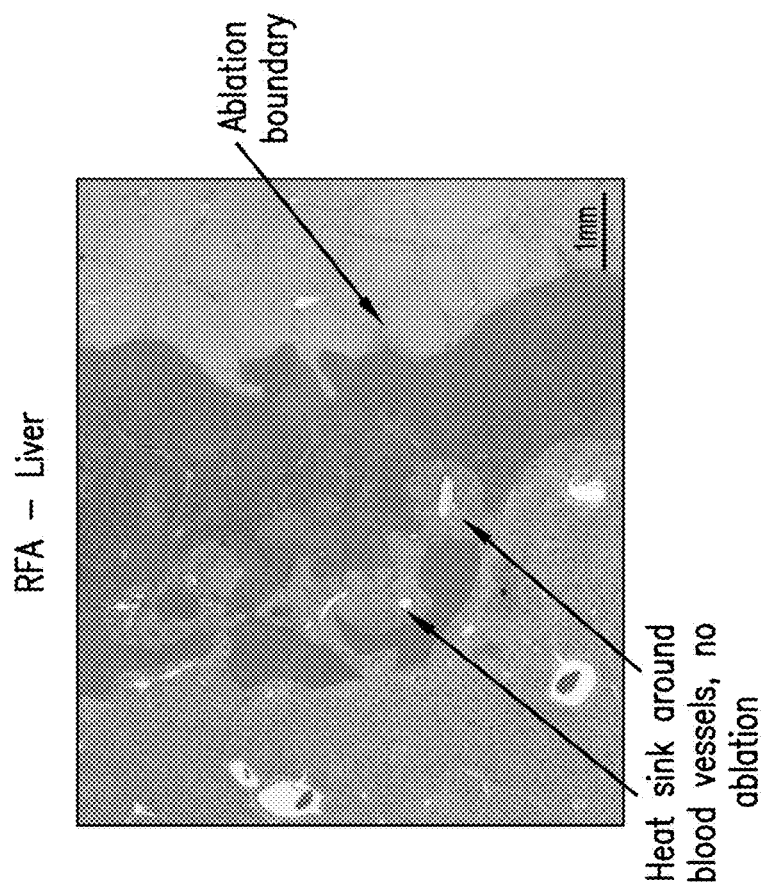
FIG. 26A is an exemplary image of an exemplary radio frequency ablation treatment area of the liver.

FIG. 25 illustrates a flow diagram of an exemplary ablation procedure. For example, at procedure 2505, the exemplary ablation procedure can begin. At procedure 2510, an exemplary imaging modality can be chosen to be used at procedure 2515 (e.g., CT 2530, ultrasound 2535, fluoroscopy 2540, PET 2545, visual/optical/microscopy 2550, chemical probes/voltage sensors 2555 and/or MM 2560). At procedure 2520, a condition can be detected (e.g., hypodense region 2565, contrast change edema 2570, contrast extravation 2375, absence of enhancement 2380, hemorrhage/hyperemia 2385, change in fluorescence 2390 and/or DWI or T1/T2 properties 2395).

Exemplary Benefits of Estress Compared with Existing Cell Ablation Techniques

Disease, malignancy, quality of life or aesthetics can cause removal or destruction of undesired tissue from the body. Two exemplary approaches can be used to achieve this, (e.g., surgical techniques and minimally invasive ablations). A significant difference between the two approaches lies in whether the tissue can be removed in its entirety from the body, as can be done in surgical techniques, or destroyed in-situ as can be done during minimally invasive ablation. The minimally invasive ablation techniques can typically be less invasive than surgical techniques, and can provide increased quality of life benefits to the patients undergoing treatment. As an effect, recovery times can be shorter, and the procedure itself can be better tolerated in a broader spectrum of patients. Commonly, during minimally invasive ablation, some form of energy can be delivered through multiple means to induce physical changes that can in turn cause unrecoverable damage to the target tissue; killing it within the body. Physiological processes, such as immune response or scar formation, can facilitate recovery of the tissue to a more desirable state. EStress offers all the benefits of currently used minimally invasive image guided ablation techniques as compared to surgical therapy, for the removal undesirable tissue.

Figure 27B:
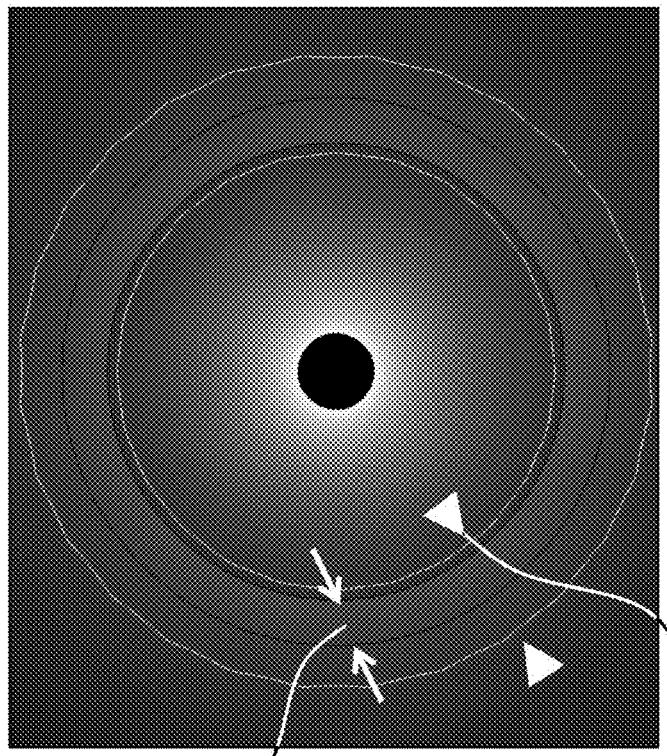
FIG. 27B is an exemplary image of an exemplary EStress treatment zone according to an exemplary embodiment of the present disclosure.
Figure 27A:
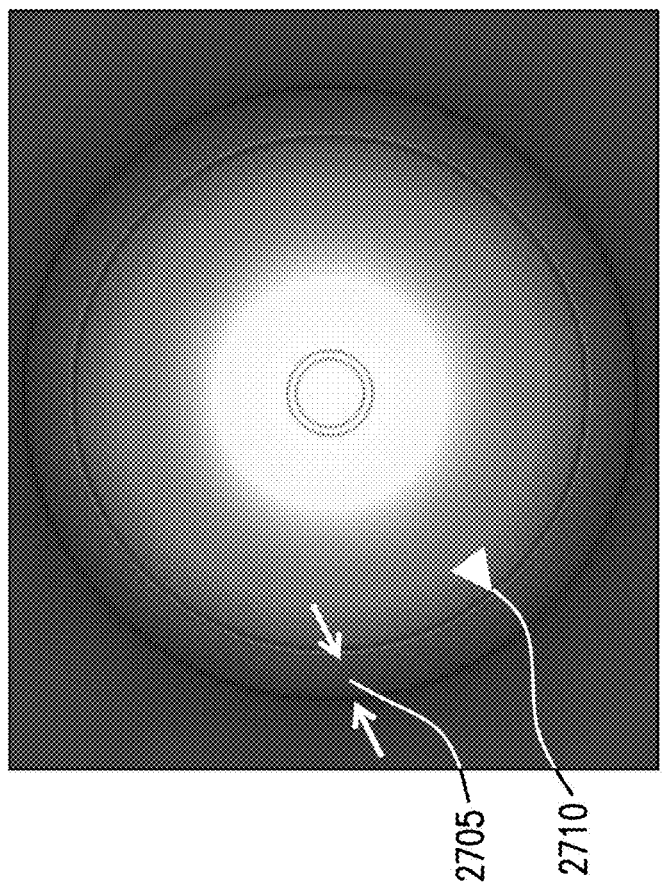
FIG. 27A is an exemplary image of an exemplary lethal temperature zone according to an exemplary embodiment of the present disclosure.

EStress can be or can include a biology mediated ablation technique. For example, EStress can ablate only the tissue or structures that have a transmembrane potential. Therefore, EStress can have no effect on extra cellular matrix, adventitia or other collagenous structures that cannot support, nor have, a transmembrane potential. Therefore, it can be possible to use EStress to selectively destroy cells in a region while leaving the extra cellular matrix largely intact. This can facilitate application of EStress for deep ablations within a lumen or adjacent to such structures. This exemplary feature can also minimize scar formation within the tissue. Additionally, vascular supply and nerves within the target region can be largely preserved thereby promoting rapid recovery following ablation. Another benefit of being a biology mediated technique can be the ability to target or affect one type of cells more than the other within the ablated region. (See, e.g., FIGS. 27A and 27B which illustrates lumen wall 2705, lethal temperature zone 2710 and EStress treatment zone 2715). Different cells within a region, such as smooth muscle and epithelial mucosal tissue, can present different response to EStress that can be contingent on their ability to alter the transmembrane potential, the time taken to recover to baseline values, metabolic rates and the presence or absence of certain ion channels and pumps. EStress can utilize such differences in biology of cells through alterations in the applied waveform as defined by the parameters described above. For example, it can be possible to use EStress to target nerves surrounding the renal artery or bronchus while completely sparing the cells in the lumen itself. Such advantages are unavailable in the known thermal ablation techniques.

EStress can injure or damage one or more cells through a combination of ion and ATP depletion, ROS damage, osmotic imbalance and electromechanical stress. These exemplary processes can rely on the alteration of the transmembrane potential of a cell. While the induction of the transmembrane voltage can be enhanced or made easier through an increase in local tissue temperature, it can be largely unaffected by thermal gradients such as large vessels or perfusion related cooling. Therefore, it can be possible to use EStress to injure or destroy tissue adjacent to large vessels where thermal ablation techniques can be ineffective. The exemplary waveform used to induce EStress can be modified to function equally well in both well perfused tissue such as the kidney and liver, or poorly perfused tissue such as the lung parenchyma and adipose tissue, without affecting the overall quality or volume of the ablation. EStress parameters are currently described for use with physiological temperature values. As noted above, any increase in local temperature can accelerate the process, and therefore, the voltage of the exemplary waveform can be reduced in magnitude to accommodate these variations. Similarly, cooling can also be employed to deliberately reduce the effectiveness or slow down the speed at which the ablation progresses. These exemplary features can increase the indication where EStress can be applied for ablation of tissue beyond the capabilities of known thermal ablation techniques.

Electroporation can be a known phenomenon where high voltage square pulses can be applied to cells to create transient pores in the cell membranes. The creation of pores can facilitate transport of materials, such as small molecules or genes, into the otherwise intact cells. Electroporation can be designed in such a way that the trauma induced to the cell can be minimal, and it can survive following introduction of the foreign bodies. The theory behind electroporation can be that repeated application of high voltage pulses can facilitate induction of transmembrane voltage in the range of about 350 mV or higher. This high transmembrane voltage can cause molecular changes to the bilipid plasma membrane with the creation of transient pores. Upon removal of the external electric field, the cell can repair these pores and reseal its plasma membrane, maintaining the cell's viability. The pores can be a few nanometers in size, and have been demonstrated through computer simulations, in vitro experiments on bilipid layers and in limited but unverified cell culture studies.

Typically, the success of pore creation, and permeation of the cell, can be demonstrated or detected in two ways. First, the creation of the pores can alter the electrical conduction properties of the cell or the tissue being exposed to the electric field. Compared to baseline values, this can be manifested by a transient but significant increase in the current drawn through the tissue or cell as the pulse can be applied. It can also be manifested by an overall increase in current pulled through the tissue. The former increase in current drawn can be attributed to the pores reducing the overall impedance to passage of current through the cell. The latter increase in current can be attributed to leakage of cytoplasm into the surrounding extra cellular region, which can alter the overall electrical conductivity properties of the tissue. Another exemplary method of detecting electropermeabilization can be through the use of tissue vitality stains and fluorescent dyes that cannot permeate an intact cell membrane. For example, propidium iodide stains cannot permeate an intact cell, but can readily permeate an electroporated cell and can stain the DNA. Likewise, fluorescent chemical sensors specific to $Na^+$, $K^+$ or $Ca^{2+}$ ions can be used to monitor change in transport of ions due to the electroporation process. Electroporation by itself can be a largely benign process and may not be intended to injure or kill cells. However, a number of ablation techniques derived from electroporation can be commonly used for injuring or destroying undesirable tissue. (See, e.g., FIGS. 28 and 29).

Figure 28:
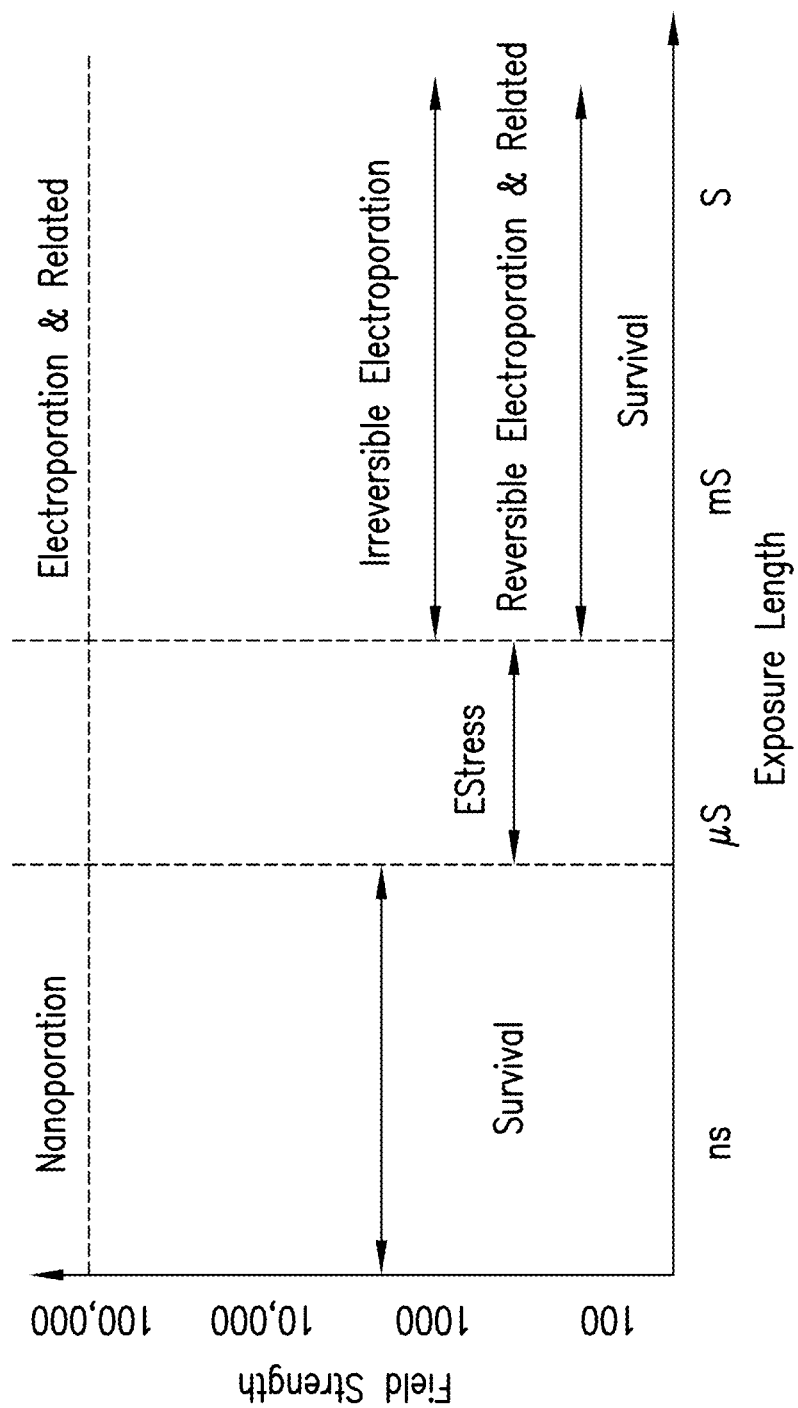
FIG. 28 is an exemplary graph illustrating exemplary strength and exemplary exposure length of time of the exemplary electric field according to an exemplary embodiment of the present disclosure.
Figure 29:
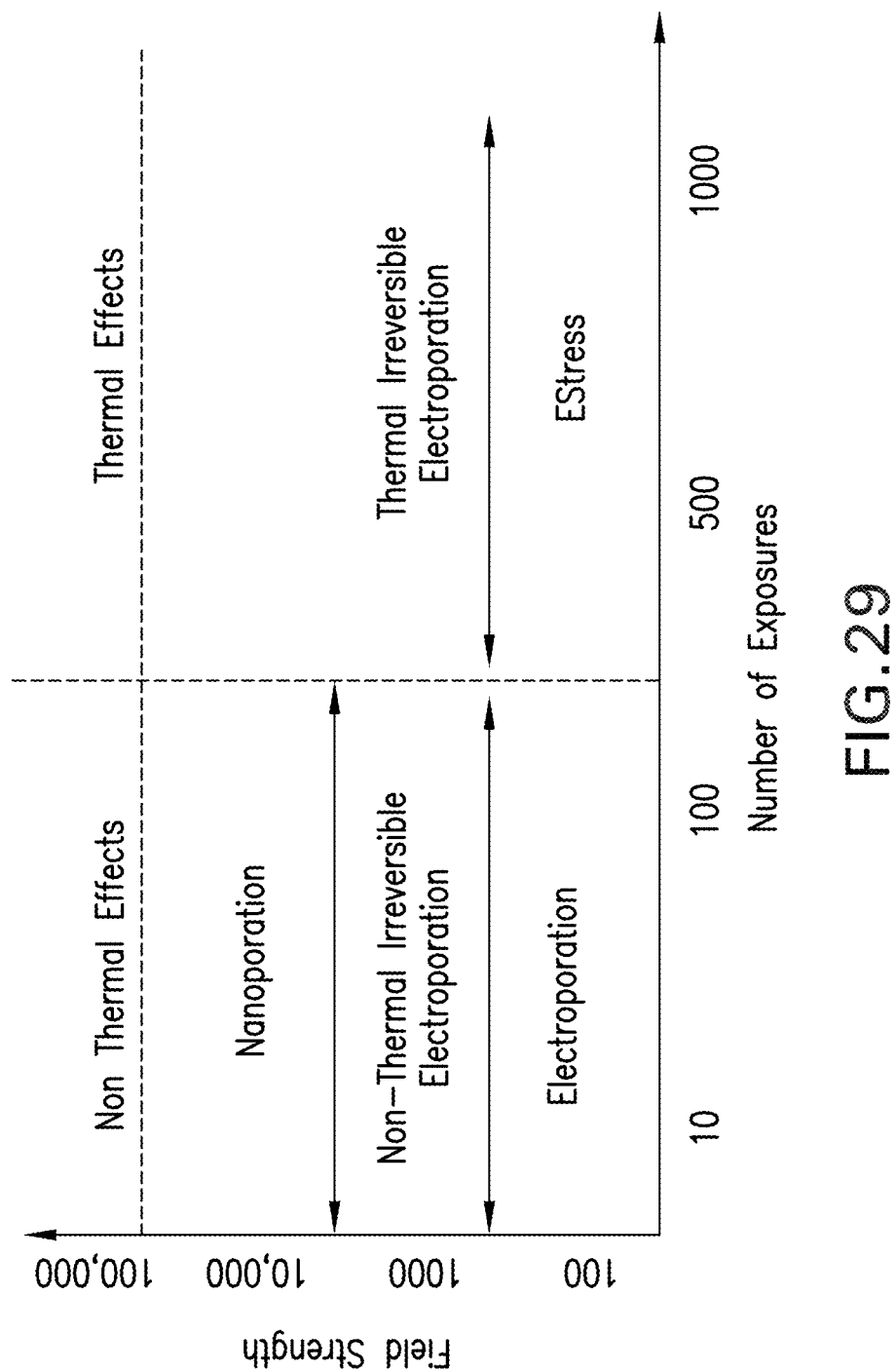
FIG. 29 is an exemplary graph illustrating exemplary field strength and exemplary number exposures of an exemplary electric field according to an exemplary embodiment of the present disclosure.

FIGS. 28 and 29 illustrate the exemplary pulse duration-field strength relation when pulsed electric fields can be used to manipulate or ablate cells. Nanoporation can be characterized by very short pulse length that can be combined with a very high field strength. Electroporation and other related procedures can utilize s longer pulse length (e.g., about 10 microseconds or longer) where cell viability can largely be determined by field strength. Field strength in excess of about 1000 V/cm can cause irreversible cell injury while lower field strengths can facilitate the survival of the cell. Field strength, and the number of exposures, can also be used in combination when using pulsed electric fields. Electroporation can utilize very low energy, and therefore, the associated temperature rise in target tissue can be limited. Cells can typically be exposed to fewer than about 500 pulses (e.g., to maintain non-thermal benefit), and differences in various exemplary procedures can be determined by increasing field strength. Electroporation can use the least field strength, while irreversible electroporation and nanoporation can employ stronger field strengths. A large number of exposures can cause thermal effects similar to what can be reported during thermal irreversible electroporation. The exemplary EStress can cause some temperature change in the tissue and can be characterized by electric fields of low field strength and exposures greater than 250 pulses to achieve ablation.

The pores created during the electropermeabilization or electroporation process can be made to endure using a modified set of exemplary treatment parameters. These enduring pores can cause permanent injury to the cell through loss of homeostasis, which can lead to eventual cell death. Here, this pore creation and cell injury can lead to cell death as compared to electroporation where typically the cell survives and recovers from the permeabilization process. The process of permanent pore creation during IRE can be achieved by using electric field strengths which can be at least two to three times higher than what can be used for electroporation. The higher field strength can be coupled with larger number of square pulse repetition that facilitates creation of transmembrane voltages in the range of about 700 mV-about 1V or higher.

The pores resultant at these very high transmembrane voltages can induce pores of a size and number that can be larger than the typical electroporation process, and as a consequence, the cell can be unable to repair the pores even following the removal of the external electric field. Similar to electroporation, pores created during IRE cannot be detected directly. However, the success of pore creation and IRE can be determined by measuring the electrical conductivity of tissue, and through the use of plasma membrane impermeable vitality stains. The pore creation process during IRE can cause permanent alteration of tissue conductivity, increasing it by a substantial value. In fact, the success of IRE can be directly correlated to the increase in magnitude of conductivity and therefore, the corresponding rise in current driven through the tissue. While there are two studies reporting direct evidence of pore formation through evaluation of treated tissue using electron microscopes, such evidence has been limited and unverifiable. In fact, it may be difficult to clearly distinguish pore formation following IRE from permanent cell permeabilization because of cell death processes, such as necrosis.

EStress can provide certain benefits, and can also differ in comparison to irreversible electroporation and derivative techniques. First, for example, the exemplary working mechanism of EStress can use permeabilization of the target tissue. If EStress can be delivered successfully, the cells can undergo stress, and can typically die due to necrosis, but the plasma membrane can remain intact through the duration of the treatment. Compared to other IRE derived techniques, this can result in limited to no edema of tissue, which can be attributed to confounding results on imaging used for follow up of the ablation. As EStress can operate through charging and discharging of cells, power drawn during treatment can remain largely constant. Due to lack of membrane permeabilization and concomitant electrical conductivity changes, unlike IRE and related techniques, there can be no increase in current drawn during EStress mediated ablation. (See, e.g., FIG. 30).

Figure 30:
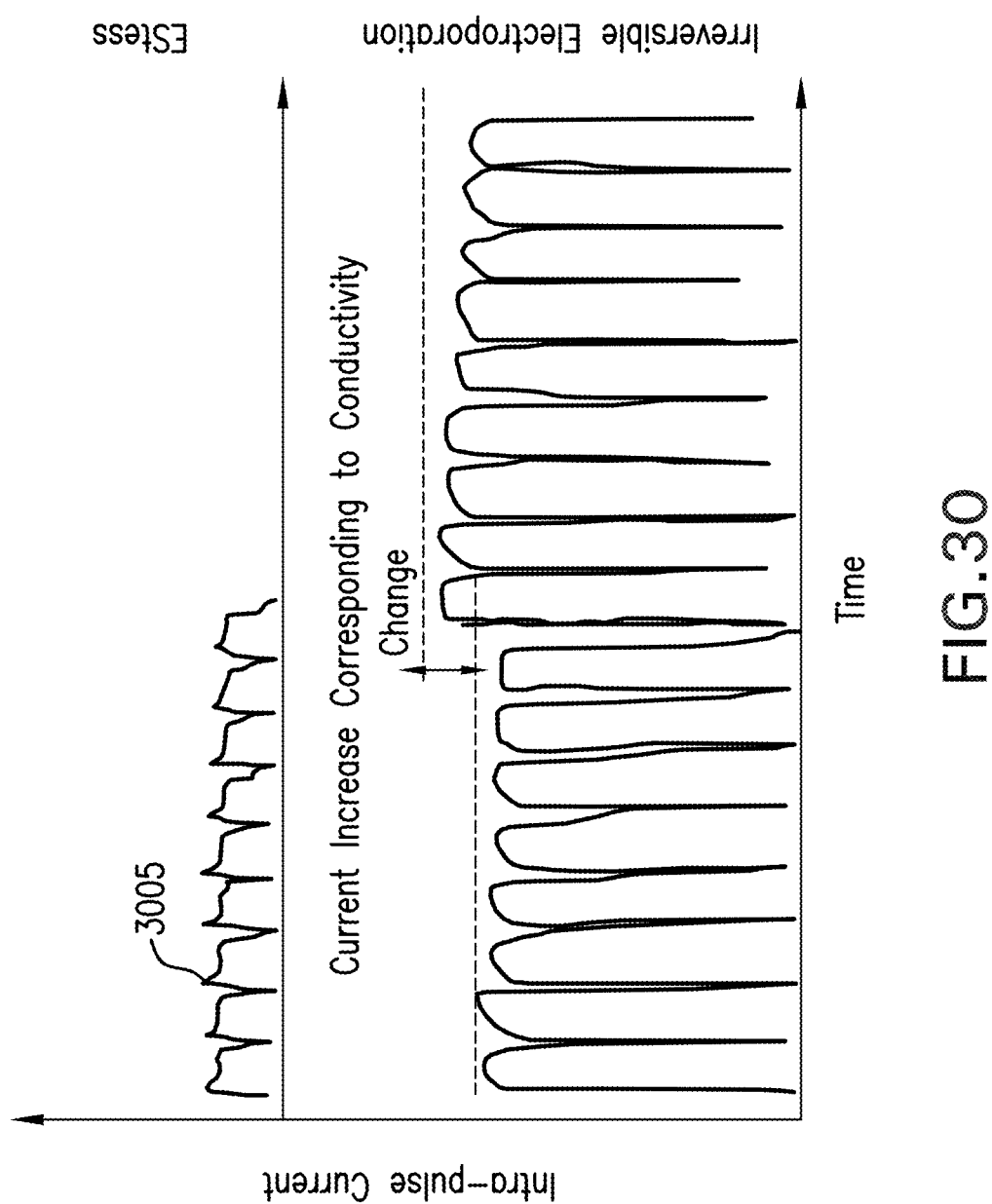
FIG. 30 is an exemplary graph illustrating exemplary current and exemplary time of the exemplary electric field according to an exemplary embodiment of the present disclosure.

FIG. 30 illustrates an exemplary graph that shows differences in current measured during electroporation and EStress. The exemplary current graph of EStress can be characterized by a sharp peak 3005, which can stem from charging of the cell membrane and can be fairly stable current from that point onwards. The impedance of the tissue can be stable or can increase slightly. During irreversible or reversible electroporation, there can be a dramatic increase in intrapulse current due to falling tissue impedance. Additionally, decreasing impedance can lead to higher current drawn as treatment delivery progresses. This can simplify the design of instruments and generators for delivery of EStress. Overall, the energy consumption for EStress can be a few times larger than IRE, but the intensity at which the energy can be consumed can be less. The lower energy density used during delivery of EStress can reduce the inadvertent activation of neuro-muscular tissue, which can be electrically sensitive, and can reduce the chances of sparking between electrode gaps, can avoid formation of gaseous bubble formation common to high current densities impingent on the electrodes and can minimize the risk of current induced cardiac arrhythmia.

EStress can function through cycling a cell through multiple transmembrane charge-discharge cycles. This can be different from IRE and related techniques where the repetition of pulses or exposures can be used to build up a transmembrane charge to a critical value, reported to be between about 0.7-1.0V, which can be the threshold used for unrecoverable disruption of the plasma membrane. During EStress, the transmembrane voltage can exceed a value of about 0.3-0.5V, which can typically be the lower threshold of reversible electroporation. Therefore, when compared to IRE and related techniques, a different set of treatment parameters can be used to achieve EStress of cells. First, the pulse length for EStress can be a few times longer than the charging time of the cell. Compared to IRE derived techniques, the pulse length can be shorter than that of the transmembrane charging time of other techniques. (See, e.g., References 3 and 4). The EStress pulse length can be magnitudes shorter than the length of other techniques for achieving non-thermal IRE. (See, e.g., Reference 1). Second, the inter-pulse spacing reported for all electroporation related techniques can be significantly shorter than that of the discharge time for a given cell. For achieving optimal EStress effects, the passive portion or the inter-pulse timing can be at least as long as the discharge time for a given cell. Finally, the electric field strength used to induce EStress effects can be significantly smaller than typical values reported for non-thermal IRE or temperature enhanced IRE (e.g., about 500-800 V/cm), supraporation (e.g., about 1 kV or higher) or high frequency electroporation (e.g., about 500-2500 V/cm for IRE and about 1 kV or higher for supraporation). The threshold for inducing EStress can have an upper bound where the early effects of electroporation begin manifesting (e.g., about 350-500 V/cm).

IRE can be an electric field strength driven threshold phenomenon, while EStress can be based on the total charge driven through a given tissue. (See, e.g., FIG. 31). This can be a fundamental difference between these two techniques with radically different mechanisms of action, and techniques used to plan, deliver or monitor the treatment. High field strengths can be used for achieving IRE in tissue, where the strong electric fields can facilitate the charging of cell membranes, which can be analogous to capacitors in an electric circuit. IRE, or even electroporation, may not occur unless certain electric field strength values can be achieved; these values have been reported to be in excess of about 500 V/cm. (See, e.g., References 1, 2 and 4). While an electric field can be used to induce a transmembrane charge for performing EStress, the stress on the cell can be induced through repeated charge-discharge cycles. Therefore, effects of EStress can be predicated on the total charge moved through a given cell, which in turn can be directly related to the temporal integration of current density induced in a tissue. Therefore, it can be possible to achieve effects of EStress at external field strengths typically too low to induce any electroporation.

FIGS. 31A and 31B illustrate the contrast evolution of a tissue injury over the course of two treatments. The exemplary EStress is illustrated in FIG. 31A and electroporation based modalities are illustrated in FIG. 31B. The treatment can be centered around a single electrode 3105 and a distal ground pad. Boundary 3110 demonstrates the maximum extent of cell injury at the end of treatment delivery. Shaded region 3115 represents locations of complete cell death (e.g., ablation). The time evolution of treatment occurs from the top to the bottom of FIG. 31A. During the exemplary EStress, a repeated exposure can cause radially increasing volume of cell death with respect to the electrode center. During the electroporation-based therapies, the extent of cell death can be established even with the first pulses, the completeness of cell death can be achieved with an increased number of pulses.

EStress can be and/or include a biologically modulated ablation technique. There can be biological and morphological differences of cells in a region that can be used to target one type of cell while sparing others. Conversely, IRE can be a treatment parameter modulated technique where, if satisfactory thresholds are achieved, most or all cells within a target region can be destroyed. As an added benefit, treatment parameters of EStress can be adjusted to achieve varying degree of cell injury or stress levels. Therefore, using EStress, the molecular transport can be transiently increased, the, metabolic activity can be increased, moderate injury can be caused or cells can be damaged beyond recovery. Such controlled injury of cells cannot be achieved using IRE. IRE can either achieve complete and irreversible damage to cells, or cause reversible electroporation where the cell recovers. Additionally, effects of EStress can be enhanced or blocked completely through use of simple pharmacological agents such as ion channel blockers or inhibitors, or ion channel promoters, to selectively target certain cells while inhibiting effects on other cells within treatment zone. In addition, commonly used non-pharmacological agents such as dextrose, physiological saline etc., can be used to alter loco-regional tissue conductivity properties and ion availability can be used to alter the progress of EStress in a heterogeneous tissue target.

EStress can provide safety benefits when compared with IRE and derivative techniques. EStress can be delivered at field strengths and voltage values that are magnitudes less than what can be commonly used to achieve IRE. This brings increased safety when applying EStress adjacent to electrically sensitive tissue such as the heart, muscle and nerves. As a non-targeted treatment technique, IRE can ablate muscularis layers of lumen structures. This can typically result in stricture formation and affects function of the lumen. EStress can be programmed to target mucosal layers while largely sparing the muscularis layers of a lumen, thus being a better candidate for performing mucosal resections.

There exist few other non-thermal electrically mediated ablation techniques. Electrochemotherapy ("ECT") and electrogenetherapy ("EGT") are examples of electroporation mediated therapies that do not involve IRE, but work through electroporation to introduce chemicals or genes into target cells for purposes that can include ablation. In addition to previously described benefits, EStress does not rely on additional pharmacological agents or genes for performing ablations. Any such agents can be merely adjuncts to the effects achieved by electrochemical therapy derived method for performing ablations are known. (See, e.g., Reference 5). They can be achieved by inducing localized electrolysis through delivery of DC current into target tissue, and the use of electroporation as an adjunct to enhance the cytotoxic effect of the radicals generated during the electrolysis process. Compared to this technique, EStress can cause little to no electrochemical change in the treated tissue. Electrochemical denaturation of tissue can cause unwanted effects including destruction of protein structures, which can be the cause of venous embolism. Additionally, the application of steady DC currents cannot be performed close to cardiac tissue. As EStress does not induce tissue electrolysis, it is beneficial over previously known procedures (see, e.g., References 5, 6, 7) where sinusoidal waves at different frequencies can be applied to limit tumor growth. These techniques are not meant to ablate tissue, but are meant to arrest the continued growth of cells by interfering with the cell division process.

Three examples are presented where EStress can be evaluated, in-vivo, using different application modalities. In the first exemplary case, EStress delivery can be planned in healthy swine liver using pair of needle electrodes. Needle spacing of about 1.5 cm and electrode dimension of about 1.5 cm can be assumed for delivery of treatment. External electric fields of about 500, 700 and 1000 V/cm. For the given needle electrode geometry and configuration, these field strengths can typically be considered insufficient for causing IRE. Current drawn during delivery of EStress can be monitored, and no change in the magnitude of current drawn can be observed, which can indicate a lack of electroporation or related effects. The cells in the treatment region can be charged and discharged about 450 times (e.g., for about 500 V/cm) or about 900 times (e.g., about 700 and 1000 V/cm), with treatment fractionated into groups of about 90 charge-discharge cycles. The anticipated treatment zones can be computed using numerical simulation by solving the Laplace distribution of electric potential and the Peleg-Fermi formulation.

Entire treatments were concluded between about 8-16 minutes based on a number of cycles used. The animals were sacrificed within about 4 hours following delivery of EStress to their liver, and the ablated regions can be extracted for histopathology analysis. Unaffected blood vessels were found well within the region of ablation, and did affect progression of treatment. Gall bladder close to the treatment zone was found to be ablated but be structurally intact without perforation. These can be interpreted as evidence that EStress therapy delivery can cause temperature rises insufficient for protein denaturation. Ablated regions presented as areas where cells underwent a mixture of coagulative necrosis and apoptosis. Histological analysis and measurements can provide evidence that lesion size can be contingent on induced current densities and number of charge-discharge cycles. The ablation can grow with increasing charge-discharge cycles providing evidence for EStress being a function of threshold charge moved through given tissue type. (See, e.g., FIGS. 32A-32C).

Figure 32B:
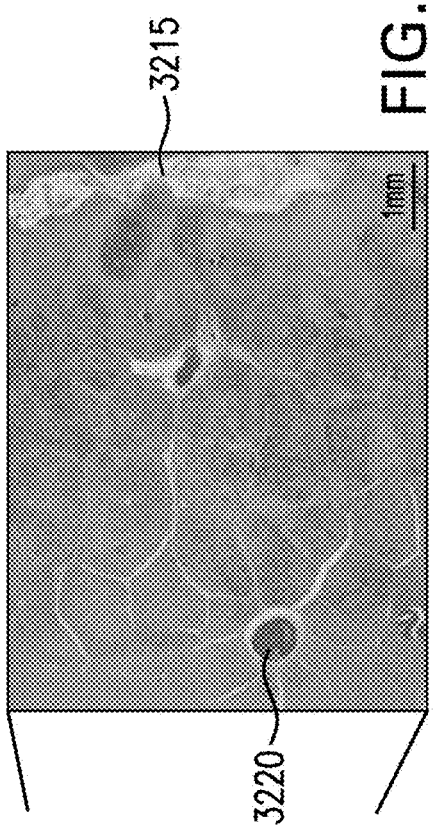
FIGS. 32A-32C are exemplary images illustrating the exemplary treatment area according to an exemplary embodiment of the present disclosure.
Figure 32C:
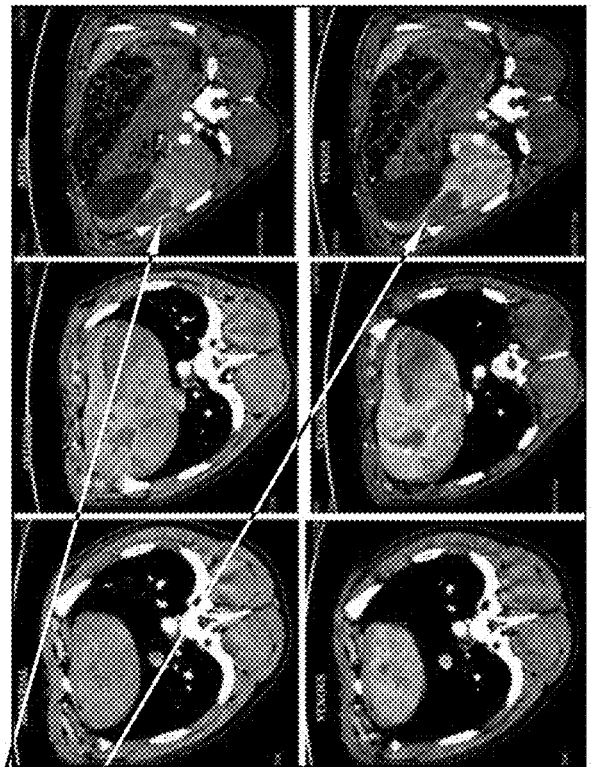
Figure 32A:
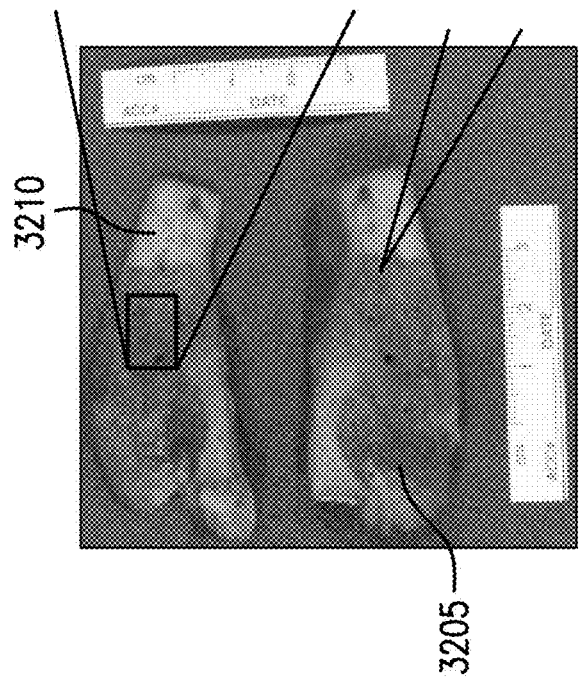
Figure 33B:
FIGS. 33A and 33B are exemplary images of the exemplary treatment area according to an exemplary embodiment of the present disclosure.
Figure 33A:
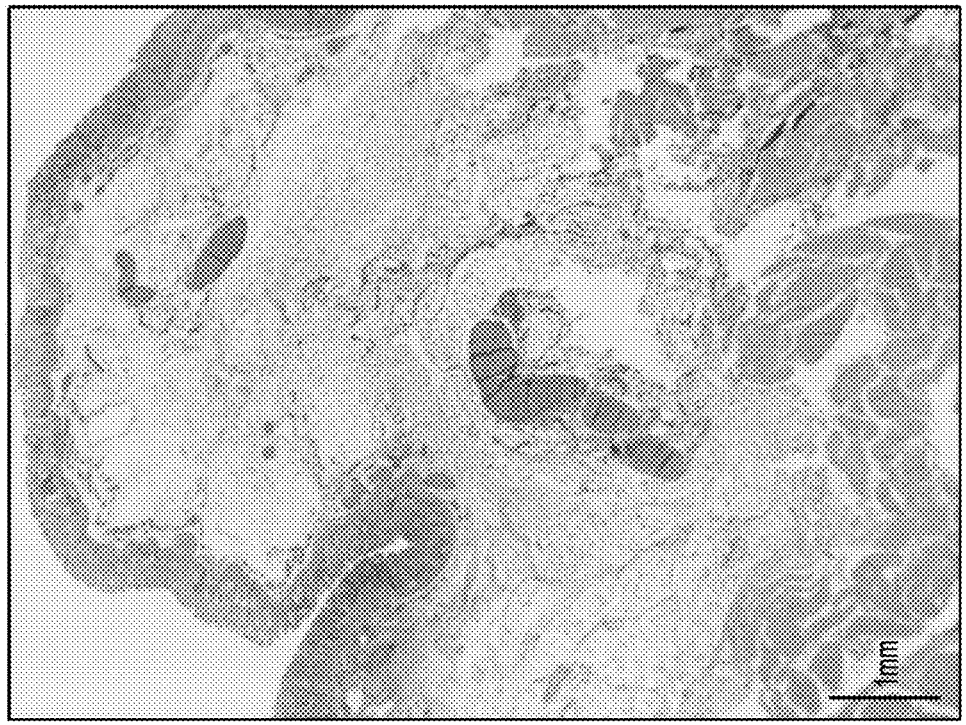

FIG. 32A illustrates a photograph of a gross liver tissue specimen treated with EStress using needle electrodes. The treated regions 3205 appear darker when compared to surrounding normal untreated tissue 3210. FIG. 32B illustrates a low magnification Hematoxylin & Eosin ("H&E") stained tissue slice where the needle tract 3215 can be seen in the corner of the image. The tissue appears hyperemic and darker when compared to surrounding untreated tissue. A blood vessel 3220 can be seen in the vicinity of the ablation zone and has not affected progression of treatment. FIG. 32C illustrates the contrast enhanced CT scans corresponding to the location of treatment from where the gross tissue specimens were recovered.

In a second example of application EStress, this exemplary ablation technique can be used for the focal mucosal resection of the swine rectal wall. A specially constructed endo-rectal probe in monopolar configuration in conjunction with a grounding pad was used for performing EStress directed mucosal ablation using two charge-discharge cycle settings in six animals. The endo-rectal electrode facilitated ablation of about 90° arc of the rectum, with about a 2 cm×1 cm cross section. EStress treatment was delivered at a voltage of about 500V for about 450 or 900 charge-discharge cycles. Current drawn during EStress was monitored to confirm explicit charge-discharge patterns. Compared to a control group of IRE directed ablations performed using the same electrode, EStress samples demonstrated less tissue edema, hemorrhage and were limited to the mucosal tissue. In addition, during IRE, increases in current drawn by the tissue can be observed, a classical indication of electroporation of tissue. Such increases can be absent during delivery of EStress. The animals were sacrificed within about 4 hours following delivery of EStress to their rectum, and the ablated regions was extracted for histopathology analysis. The EStress ablation performed at the lower cycle setting indicated evidence of patchy and incomplete ablation, with some regions of viable tissue interleaved with ablated tissue. The mucosa was largely ablated with little to no penetration to the muscle layers. In the higher cycle setting the mucosal layer was found to be uniformly and completely ablated with minor penetration of ablation into the muscularis layers. However, compared with the IRE ablations performed with similar setting, the lesions was found to be more superficial and controlled with minimal edema. (See, e.g., 34A and 34B).

An exemplary comparison of an irreversible electroporation is illustrated in FIG. 34A, and the exemplary EStress is illustrated in FIG. 34B, for a treated swine rectum. The IRE treated rectum can be characterized by tissue edema (e.g., from the release of cytosol from electroporation), with hemorrhage and collagen separation. Changes in EStress ablated rectum can be milder, with limited tissue edema, and the injury can largely be limited to the mucosa.

Figure 34:
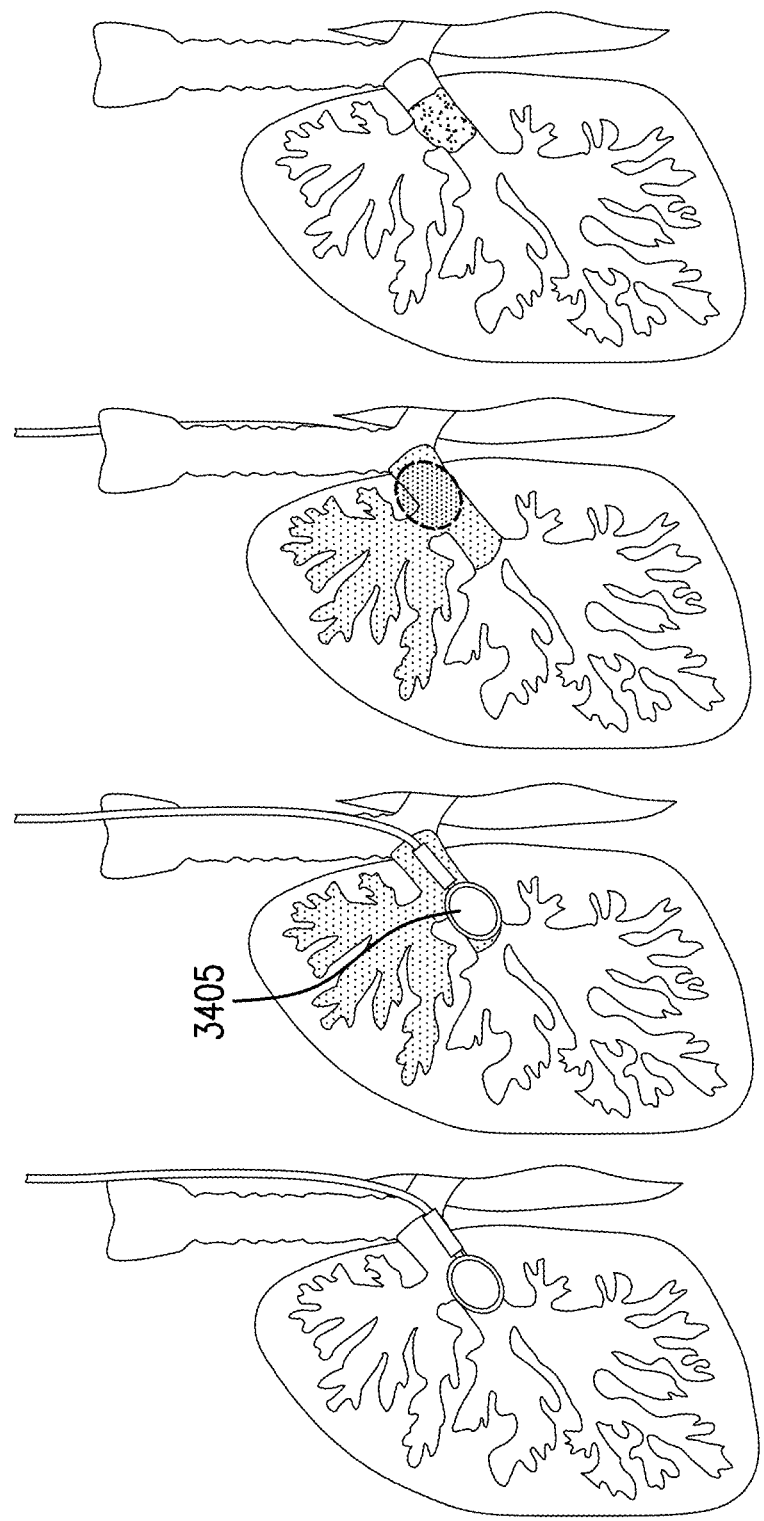
FIG. 34 is a set of exemplary illustrations of the exemplary treatment areas according to an exemplary embodiment of the present disclosure.
Figure 35:
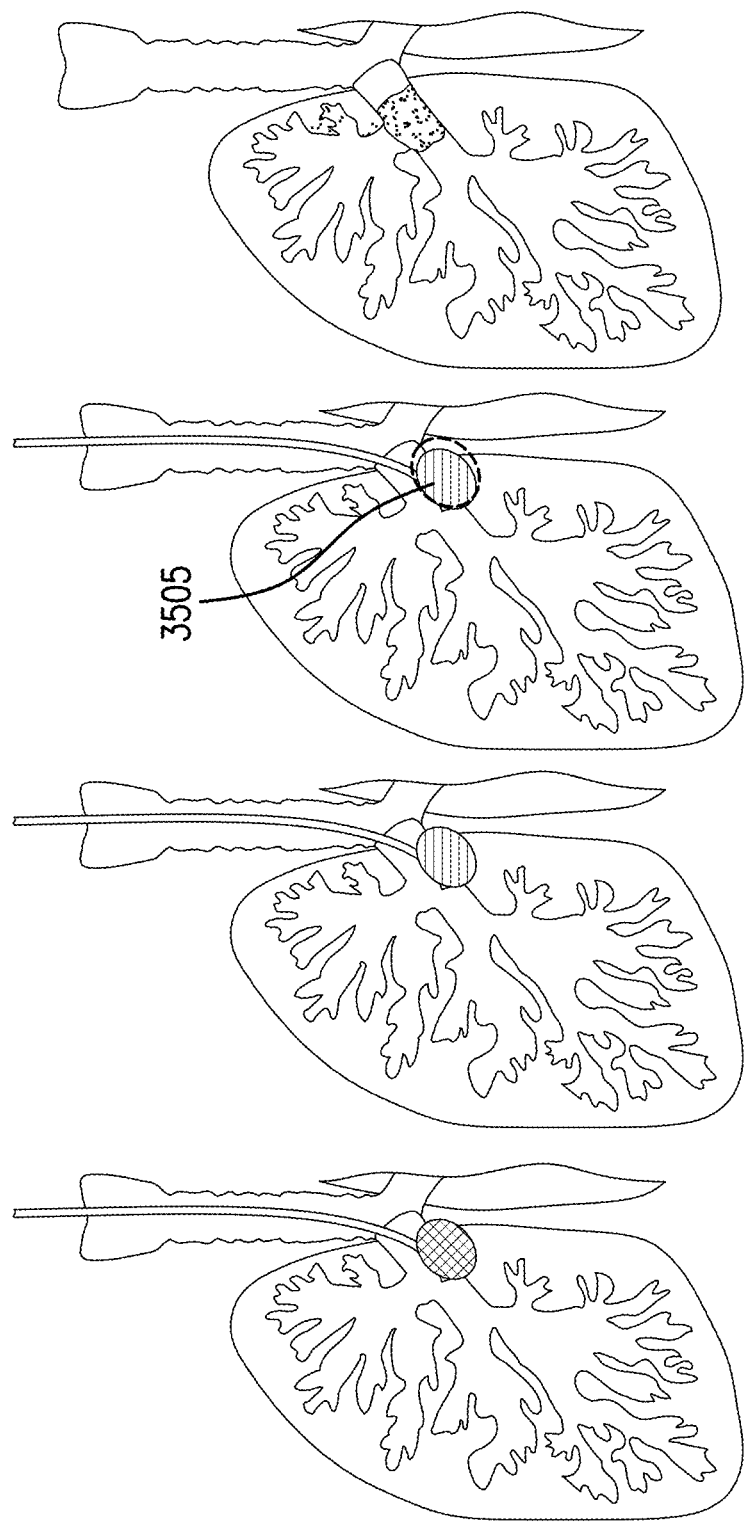
FIG. 35 is a set of exemplary illustrations of the exemplary treatment areas according to an exemplary embodiment of the present disclosure.

In the third exemplary demonstration of EStress, catheter directed ablation of the bronchial mucosa was attempted in a healthy swine model. Two different exemplary approaches were used for the delivery of EStress. In the first exemplary approach the lung was isolated and filled with normal saline, following which EStress was delivered using a catheter with a coil electrode at its tip to achieve circumferential ablation of the bronchial mucosa. In the second approach, a catheter was made with a sponge like material at its tip. (See, e.g., FIGS. 34 and 35). FIG. 34 illustrates an exemplary procedure where a balloon catheter 3405 can be used to occlude a bronchi to fill a segment of the lung with a conductive fluid. The exemplary EStress ablation can then be performed in a target segment. FIG. 35 illustrates an exemplary procedure where the catheter tip is wetted with a conductive fluid 3505 to perform more targeted ablations.

The catheter was introduced into the bronchus, and saline was passed through the distal end to complete the electrical pathway. Current was delivered through this "wet electrode" and a grounding pad to perform ablation of the bronchial mucosa. Previously described treatment parameters were used in both catheter directed treatment experiments, and ablation was achieved successfully. For both cases treatment was completed successfully without incident and desired mucosal ablation can be achieved. (See, e.g., FIGS. 36A-36C). FIGS. 36A and 36B illustrate treated (arrows 3605) and untreated (arrows 3610) segments of swine bronchus. FIG. 36C illustrates low magnification images of H&E stained bronchial tissue. Treated tissue can be characterized by loss of epithelium, and necrosis of glands.

Figure 37:
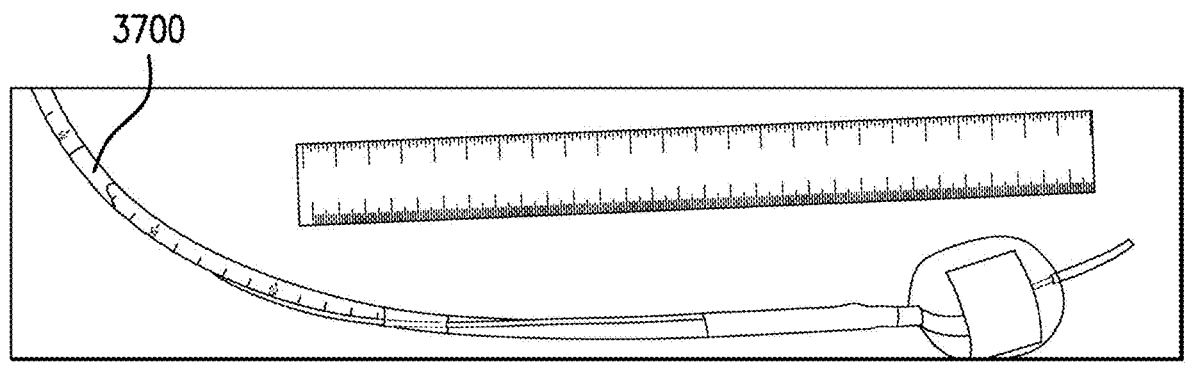
FIG. 37 is an exemplary image of an exemplary catheter according to an exemplary embodiment of the present disclosure.
Figure 38:
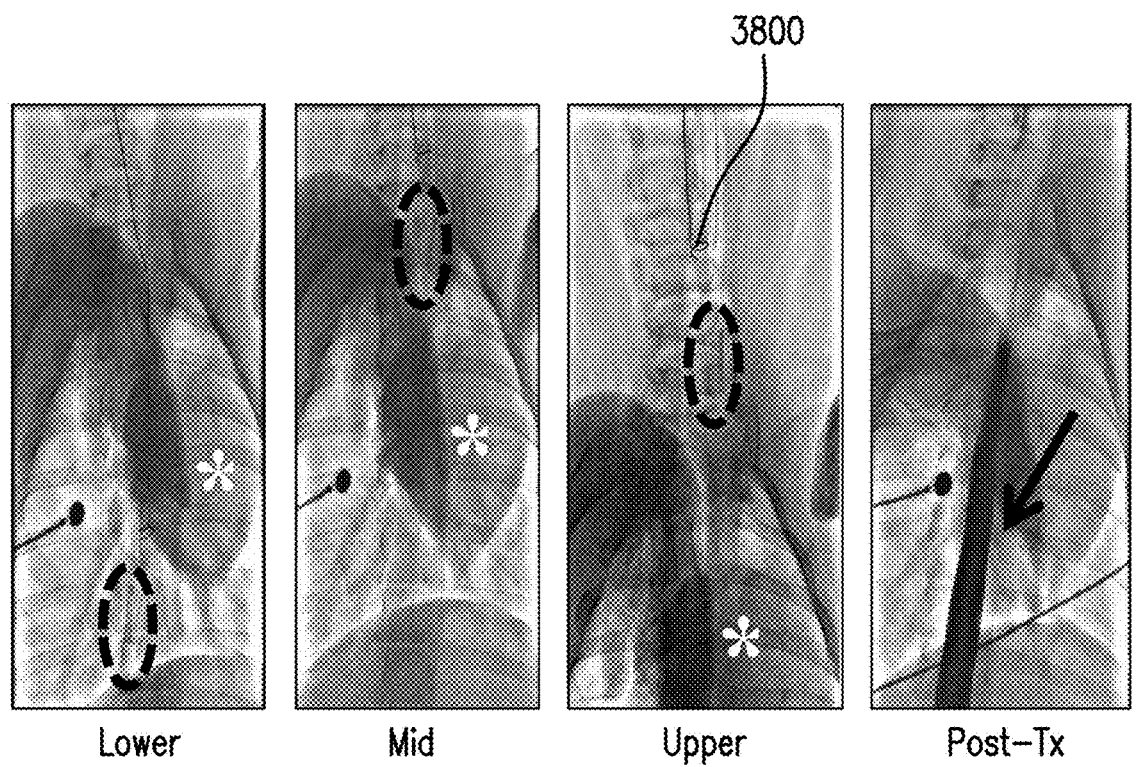
FIG. 38 is a set of exemplary images of an exemplary placement of the exemplary catheter of FIG. 37 according to an exemplary embodiment of the present disclosure.

FIG. 37 illustrates an exemplary image of an exemplary catheter 3700. Such exemplary catheter 3700 can be used to ablate an exemplary tissue (e.g., esophageal mucosa in a normal swine model). FIG. 38 shows a set of exemplary images of an exemplary placement of the exemplary catheter 3700 of FIG. 37. The exemplary images illustrate the placement of catheter electrode 3800 at various exemplary locations within the esophagus (e.g., within the peri-cardiac region). The exemplary catheter 3700 can be used to ablate tissue without significant cardiac adverse events. Post-treatment the patency of the lumen can be demonstrated by the absence of extravasation of the injected contrast.

Figure 39:
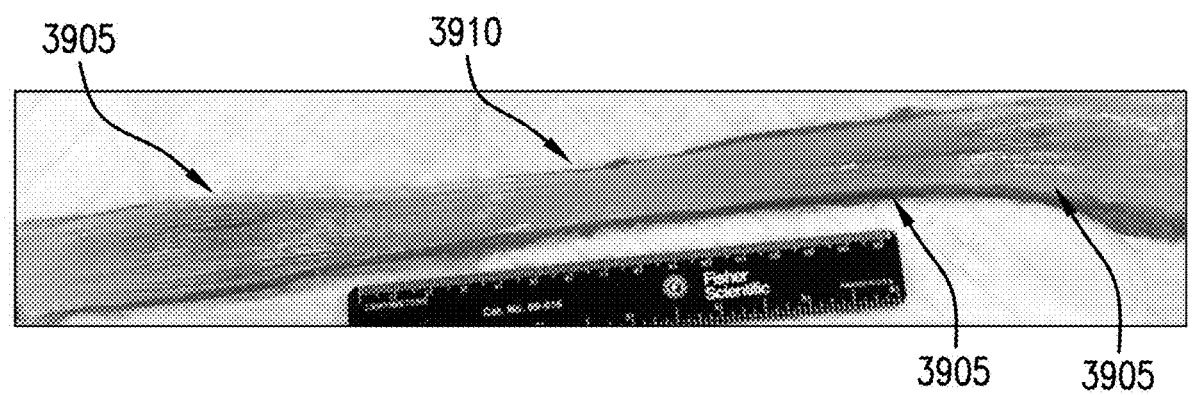
FIG. 39 is an exemplary image of an exemplary swine esophagus according to an exemplary embodiment of the present disclosure.

FIG. 39 illustrates an exemplary image of an exemplary swine esophagus. A gross examination of the swine esophagus illustrates circumferential regions of discoloration and hyperemia consistent with EStress mediated ablation. There can be a small amount, or zero, tissue edema, which can normally be observed during electroporation. Element 3905 provides the locations of exemplary lumen that can receive treatment, Element 3910 provides a location of sham balloon placement without delivery of the exemplary EStress.

Figure 40:
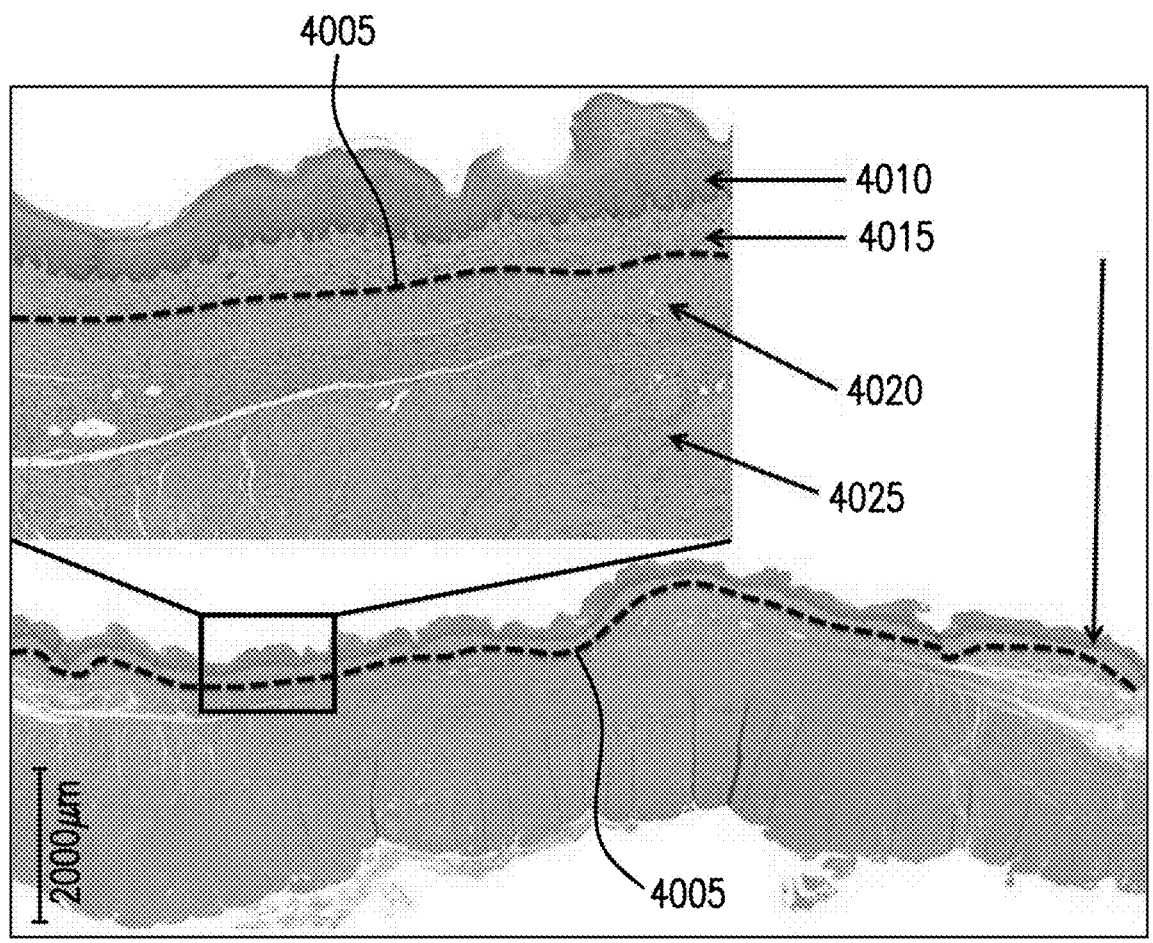
FIG. 40 is a set of exemplary images of a cross-section of stained swine esophagus treated with the exemplary EStress system/apparatus according to an exemplary embodiment of the present disclosure.

FIG. 40 shows a set of exemplary images of an exemplary cross-section of photomicrograph of an H&E stained swine esophagus treated with the exemplary EStress. Various layers of the swine esophagus can be seen including: Mucosa 4010, Depth of Treatment Effect 4015, Submucosa 4020 and Smooth Muscle Layer 4025. Elements 4005 indicate the extent of penetration of the ablation. The exemplary EStress parameters were chosen to target the epithelial type cells in the mucosa while the underlying smooth muscle cells in the muscularis were spared.

Figure 41:
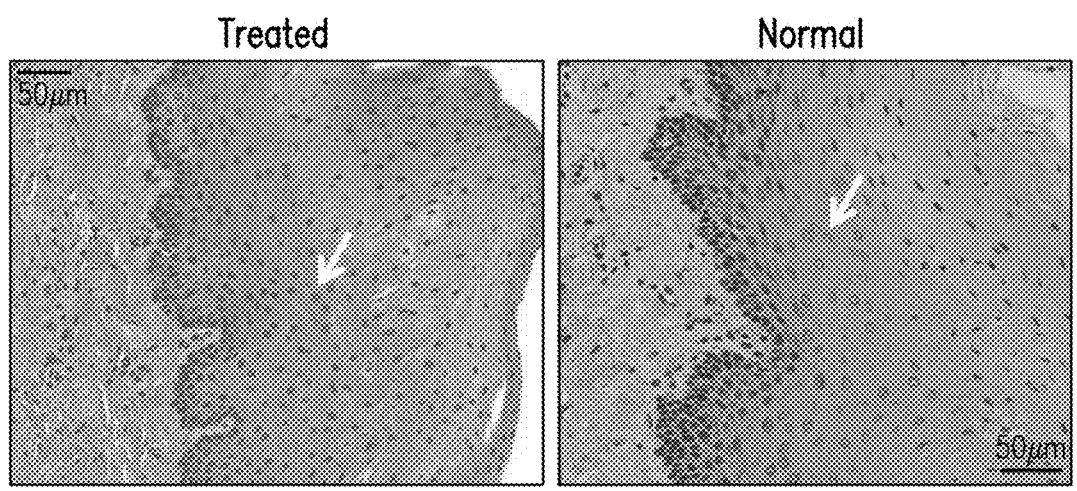
FIG. 41 is a set of exemplary images of normal and treated epithelium according to an exemplary embodiment of the present disclosure.

FIG. 41 shows a set of exemplary images of normal and treated epithelium. High magnification image of the mucosa is illustrated, which shows morphological differences between viable and necrotic epithelial cells in the mucosa.

Figure 42:
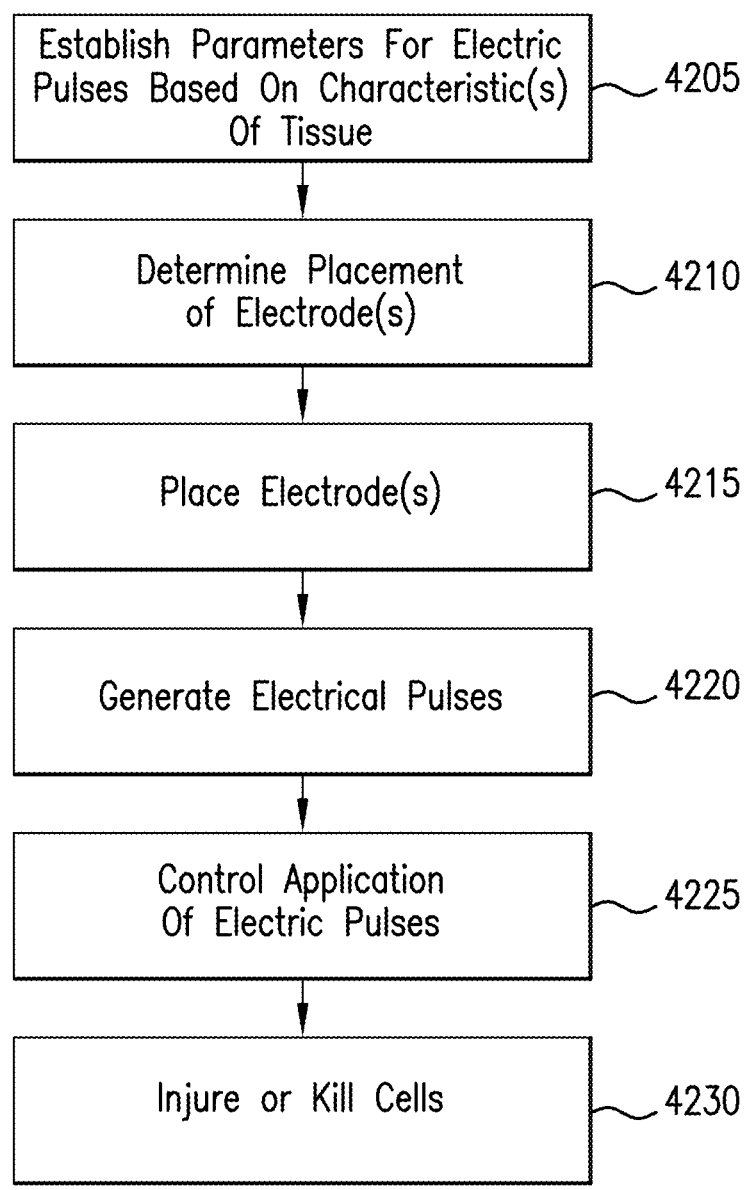
FIG. 42 is an exemplary flow diagram illustrating an exemplary method for injuring or killing tissue and/or cells according to an exemplary embodiment of the present disclosure.

FIG. 42 illustrates an exemplary flow diagram illustrating an exemplary method 4200 for injuring or killing cells and/or tissue. For example, at procedure 4205, parameters for electric pulses can be established or determined based on one or more characteristics on the tissue to be injured or killed. At procedure 4210, the location of the placement of the electrode (e.g., at or near the tissue) can be determined, and the electrode can be placed at or near the tissue in procedure 4215. In procedure 4220, electrical pulses can be generated for which an application of the electrical pulses can be controlled at procedure 4225. At procedure 4230, the cells and/or tissue can be injured or killed.

In a further exemplary embodiment, the exemplary catheter of the exemplary EStress device/apparatus can include at least one fixed electrode (a first electrode), and at least one electrode (a second electrode) that can move relative to the fixed electrode. This facilitates the ability to control for the length of lesions without having to perform multiple repositions between ablations. The second electrode can be made of material that can be impedance matched to the target tissue being ablated, and can be surrounded by a conductive fluid that can also be impedance matched to achieve specific ablation effects. The conductive fluid can serve as a conductor for electrical connectivity, but can also be used as a heat sink to reduce or enhance the thermal effects of ablation, and can serve as a reservoir for delivery of chemicals and therapeutic agents to the target regions. The exemplary device can have both temperature and electrical sensors to monitor the course of the ablation. Ablations that can be performed using this exemplary device can include, but is not limited, to radiofrequency ablation, irreversible electroporation, electroporation, electrochemical therapy, electrochemotherapy, electrogenetherapy, induced endocytosis, high frequency electroporation, nanoporation and finally, EStress. The exemplary device can also perform transmural ablation penetrating into surrounding tissue without causing perforation or heat induced stricture of the lumen.

Figure 43:
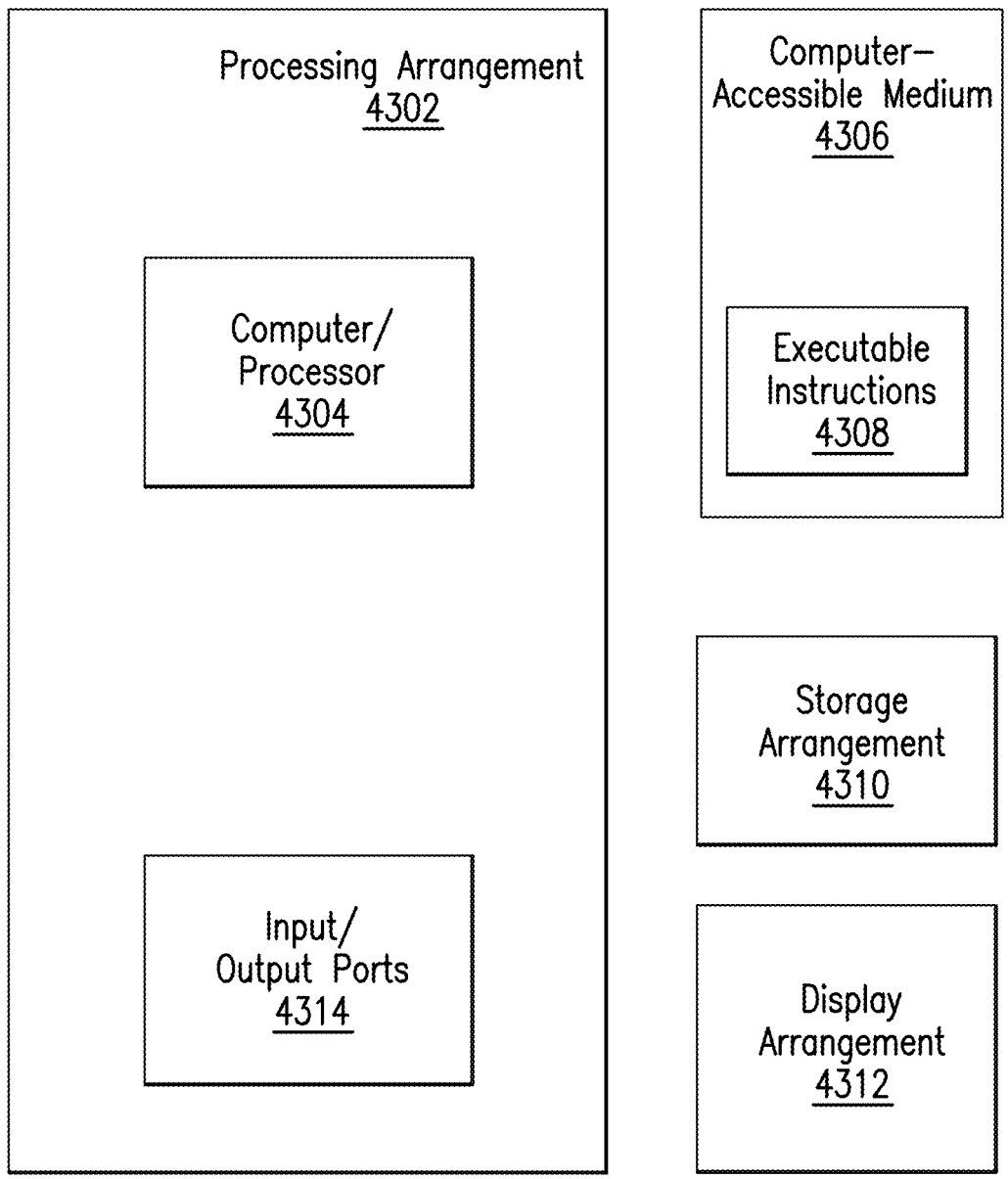
FIG. 43 is an illustration of an exemplary block diagram of an exemplary system in accordance with certain exemplary embodiments of the present disclosure.

FIG. 43 shows a block diagram of an exemplary embodiment of a system according to the present disclosure. For example, exemplary procedures in accordance with the present disclosure described herein can be performed by a processing arrangement and/or a computing arrangement 4302. Such processing/computing arrangement 4302 can be, for example, entirely or a part of, or include, but not limited to, a computer/processor 4304 that can include, e.g., one or more microprocessors, and use instructions stored on a computer-accessible medium (e.g., RAM, ROM, hard drive, or other storage device).

As shown in FIG. 43, e.g., a computer-accessible medium 4306 (e.g., as described herein above, a storage device such as a hard disk, floppy disk, memory stick, CD-ROM, RAM, ROM, etc., or a collection thereof) can be provided (e.g., in communication with the processing arrangement 4302). The computer-accessible medium 4306 can contain executable instructions 4308 thereon. In addition or alternatively, a storage arrangement 4310 can be provided separately from the computer-accessible medium 4306, which can provide the instructions to the processing arrangement 4302 so as to configure the processing arrangement to execute certain exemplary procedures, processes and methods, as described herein above, for example.

Further, the exemplary processing arrangement 4302 can be provided with or include an input/output arrangement 4314, which can include, for example, a wired network, a wireless network, the internet, an intranet, a data collection probe, a sensor, etc. As shown in FIG. 43, the exemplary processing arrangement 4302 can be in communication with an exemplary display arrangement 4312, which, according to certain exemplary embodiments of the present disclosure, can be a touch-screen configured for inputting information to the processing arrangement in addition to outputting information from the processing arrangement, for example. Further, the exemplary display 4312 and/or a storage arrangement 4310 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.
[1] U.S. Patent Publication No. 2006/0293731 Rubinsky et al.
[2] U.S. Patent Publication No. 2008/0015571 Rubinsky et al.
[3] U.S. Patent Publication No. 2011/0118732 Rubinsky et al.
[4] U.S. Patent Publication No. 2012/0277741 to Rubinsky et al.
[5] U.S. Pat. No. 8,114,072 to Long et al.
[6] U.S. Patent Publication No. 2012/0220998 to Long et al.
[7] U.S. Patent Publication No. 2012/0221002 to Long et al.
[8] European Patent No. EP 1207797 to Beebe et al.
[9] U.S. Patent Publication No. 2010/0261994 to Davalos et al.
[10] U.S. Patent Publication No. 2012027741 to Davalos et al.
[11] U.S. Patent Publication No. 2010/0030211 to Davalos et al.
[12] U.S. Pat. No. 8,048,067 to Davalos et al.
[13] U.S. Pat. No. 8,282,631 to Davalos et al.
[14] U.S. Pat. Nos. 7,680,543, 7,722,606; U.S. Patent Publication No. 2009/0076502, 2011/0060393 to Azure et al.

What is claimed is:

1. A non-transitory computer-accessible medium having stored thereon computer-executable instructions for ablating at least one electrically-sensitive tissue, wherein, when a computer hardware arrangement executes the instructions, the computer hardware arrangement is configured to perform procedures comprising:

establishing particular parameters for electric pulses based on at least one characteristic of the at least one electrically-sensitive tissue;

controlling an application of the electric pulses to all of the at least one electrically-sensitive tissue for a plurality of automatically controlled and separated time periods to ablate less than all of the at least one electrically-sensitive tissue such that a substantial electroporation of a majority of the at least one electrically-sensitive tissue is at least one of prevented or reduced; and controlling an impedance level of the at least one electrically-sensitive tissue while the electric pulses are applied.

2. The computer-accessible medium of claim 1, wherein the at least one electrically-sensitive tissue is at least one of (i) cardiac tissue or (ii) at least one nerve.

3. The computer-accessible medium of claim 1, wherein the computer hardware arrangement is further configured to control the application of the electric pulses to at least one of (i) hyperpolarize or (ii) depolarize at least one particular cell of the at least one electrically-sensitive tissue.

4. The computer-accessible medium of claim 1, wherein the computer hardware arrangement is further configured to:
apply the electric pulses using at least one electrode; and
modify at least one waveform of the electric pulses based on a polarity of the at least one electrode.

5. A method for ablating at least one electrically-sensitive tissue, comprising:
using a computer hardware arrangement, establishing particular parameters for electric pulses based on at least one characteristic of the at least one electrically-sensitive tissue;
controlling an application of the electric pulses to all of the at least one electrically-sensitive tissue for a plurality of automatically controlled and separated time periods to ablate less than all of the at least one electrically-sensitive tissue such that an electroporation of a majority of the at least one electrically-sensitive tissue is at least one of prevented or reduced; and
controlling an impedance level of the at least one electrically-sensitive tissue while the electric pulses are applied.

6. The method of claim 5, wherein the electric pulses include at least one waveform.

7. The method of claim 6, wherein the at least one waveform is based on at least one of (i) an applied voltage of the electric pulses, (ii) a sign of the electric pulses, (iii) a length of exposure of the at least one electrically-sensitive tissue to the electric pulses, (iv) a relative field strength of the electric pulses, (v) a current density of the electric pulses, or (vi) a duty cycle of the electric pulses.

8. The method of claim 6, wherein the at least one waveform has a shape of at least one of (i) a square, (ii) a sawtooth, (iii) a triangle, (iv) a trapezoid, or (v) an exponential sinusoidal pulse.

9. The method of claim 6, further comprising applying at least one waveform as at least one of (i) monopolar, (ii) bipolar, or (iii) direct current shifted.

10. The method of claim 5, wherein the at least one electrically-sensitive tissue is at least one of (i) cardiac tissue, or (ii) at least one nerve.

11. The method of claim 5, further comprising controlling the application of the electric pulses to at least one of (i) hyperpolarize or (ii) depolarize at least one particular cell of the at least one electrically-sensitive tissue.

12. The method of claim 5, further comprising at least one of (i) injuring at least one cell of the at least one electrically-sensitive tissue, (ii) killing the at least one cell, (iii) increasing a metabolic rate of the at least one cell, (iv) increasing a vulnerability to immune processes of the at least one cell based on exposure to the electric pulses, (v) causing heating or energy transfer through a cell membrane of the at least one cell, (vi) depleting at least one of an energy or at least one ATP reserve of the at least one cell, (vii) causing at least one of an osmotic imbalance or an ionic imbalance of the at least one cell, (viii) disrupting normal cellular processes dependent on a membrane potential of the at least one cell, (ix) deforming and modifying electrically-sensitive proteins and structures on the cell membrane of the at least one cell, (x) repeatedly altering a polarization of the at least one cell, or (xi) interfering with a transmembrane potential of the at least one cell.

13. The method of claim 5, further comprising disrupting at least one of at least one bioelectric response or at least one cellular process of at least one cell of the at least one electrically-sensitive tissue based on the electric pulses.

14. The method of claim 5, further comprising:
applying the electric pulses using at least one electrode; and
modifying at least one waveform of the electric pulses based on a polarity of the at least one electrode.

15. The method of claim 14, further comprising determining a location where to place the at least one electrode using at least one of (i) computed tomography, (ii) magnetic resonance imaging, (iii) ultrasound, (iv) positron emission tomography, (v) fluorescence imaging, or (vi) direct visual imaging using a camera.

16. The method of claim 14, wherein the at least one electrode includes a plurality of electrodes which are configured to be placed near and away from the at least one electrically-sensitive tissue.

17. The method of claim 5, wherein the electroporation of the majority of the at least one electrically-sensitive tissue is at least one of prevented or reduced due to an effect of the electric pulses which have the particular parameters on the at least one electrically-sensitive tissue.

18. The method of claim 5, wherein the particular parameters are based on at least one of a shape, a size, a biology or a morphology of the at least one electrically-sensitive tissue.

19. The method of claim 5, further comprising ablating the at least one electrically-sensitive tissue through mediation of at least one cell membrane potential of the at least one electrically-sensitive tissue without crossing a threshold that induces electroporation.

20. The method of claim 19, further comprising inducing the mediation of the at least one cell membrane potential using a plurality of charge discharge cycles.

21. The method of claim 5, wherein the at least one electrically-sensitive tissue includes at least one particular type of electrically-sensitive tissue.

22. The method of claim 5, wherein the at least one electrically-sensitive tissue includes at least one particular type of cells.

23. A method for ablating at least one electrically-sensitive tissue, comprising:
using a computer hardware arrangement, establishing particular parameters for electric pulses based on at least one characteristic of the at least one electrically-sensitive tissue;
controlling an application of the electric pulses to all of the at least one electrically-sensitive tissue for a plurality of automatically controlled and separated time periods to ablate less than all of the at least one electrically-sensitive tissue such that an electroporation of a majority of the at least one electrically-sensitive tissue is at least one of prevented or reduced; and
impairing a specific function of at least one cell of the at least one electrically-sensitive tissue based on a sign of at least one of the electric pulses.

24. A method for ablating at least one electrically-sensitive tissue, comprising:

using a computer hardware arrangement, establishing particular parameters for electric pulses based on at least one characteristic of the at least one electrically-sensitive tissue;

controlling an application of the electric pulses to all of the at least one electrically-sensitive tissue for a plurality of automatically controlled and separated time periods to ablate less than all of the at least one electrically-sensitive tissue such that an electroporation of a majority of the at least one electrically-sensitive tissue is at least one of prevented or reduced; and inducing a creation of reactive oxygen species in at least one of intra-cellular or inter-cellular spaces of at least one cell of the at least one electrically-sensitive tissue to degrade a cellular structure of the at least one cell.

25. A system for ablating at least one electrically-sensitive tissue, comprising:
a computer hardware arrangement configured to:
establish particular parameters for electric pulses based on at least one characteristic of the at least one electrically-sensitive tissue;
control an application of the electric pulses to the at least one electrically-sensitive tissue for a plurality of automatically controlled and separated time periods to ablate the at least one electrically-sensitive tissue such that an electroporation of a majority of the at least one electrically-sensitive tissue is at least one of prevented or reduced; and
control an impedance level of the at least one electrically-sensitive tissue while the electric pulses are applied.

26. The system of claim 25, wherein the at least one electrically-sensitive tissue is at least one of (i) cardiac tissue or (ii) at least one nerve.

27. The system of claim 25, wherein the computer hardware arrangement is further configured to control the application of the electric pulses to at least one of (i) hyperpolarize or (ii) depolarize at least one particular cell of the at least one electrically-sensitive tissue.

28. The system of claim 25, wherein the computer hardware arrangement is further configured to:
apply the electric pulses using at least one electrode; and
modify at least one waveform of the electric pulses based on a polarity of the at least one electrode.

29. A non-transitory computer-accessible medium having stored thereon computer-executable instructions for ablating at least one electrically-sensitive tissue, wherein, when a computer hardware arrangement executes the instructions, the computer hardware arrangement is configured to perform procedures comprising:
establishing particular parameters for electric pulses based on at least one characteristic of the at least one electrically-sensitive tissue;
controlling an application of the electric pulses to all of the at least one electrically-sensitive tissue for a plurality of automatically controlled and separated time periods to ablate less than all of the at least one electrically-sensitive tissue such that a substantial electroporation of a majority of the at least one electrically-sensitive tissue is at least one of prevented or reduced; and
performing at least one of:
impairing a specific function of at least one cell of the at least one electrically-sensitive tissue based on a sign of at least one of the electric pulses, or
inducing a creation of reactive oxygen species in at least one of intra-cellular or inter-cellular spaces of the at least one cell of the at least one electrically-sensitive tissue to degrade a cellular structure of the at least one cell.

30. A system for ablating at least one electrically-sensitive tissue, comprising:
a computer hardware arrangement configured to:
establish particular parameters for electric pulses based on at least one characteristic of the at least one electrically-sensitive tissue;
control an application of the electric pulses to the at least one electrically-sensitive tissue for a plurality of automatically controlled and separated time periods to ablate the at least one electrically-sensitive tissue such that an electroporation of a majority of the at least one electrically-sensitive tissue is at least one of prevented or reduced; and
perform at least one of:
impair a specific function of at least one cell of the at least one electrically-sensitive tissue based on a sign of at least one of the electric pulses, or
induce a creation of reactive oxygen species in at least one of intra-cellular or inter-cellular spaces of the at least one cell of the at least one electrically-sensitive tissue to degrade a cellular structure of the at least one cell.

* * * * *